(12) United States Patent
Castado

(10) Patent No.: US 9,644,024 B2
(45) Date of Patent: May 9, 2017

(54) NUCLEOTIDE SEQUENCES, VECTORS AND HOST CELLS

(71) Applicant: GLAXOSMITHKLINE BIOLOGICALS S.A., Rixensart (BE)

(72) Inventor: Cindy Castado, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/041,924

(22) Filed: Feb. 11, 2016

(65) Prior Publication Data

US 2016/0159867 A1 Jun. 9, 2016

Related U.S. Application Data

(63) Continuation of application No. 14/122,690, filed as application No. PCT/EP2012/005793 on May 25, 2012, now Pat. No. 9,290,565.

(60) Provisional application No. 61/490,707, filed on May 27, 2011, provisional application No. 61/490,716, filed on May 27, 2011, provisional application No. 61/490,734, filed on May 27, 2011.

(51) Int. Cl.
| | |
|---|---|
| *C07H 21/04* | (2006.01) |
| *C07K 16/12* | (2006.01) |
| *A61K 39/08* | (2006.01) |
| *C07K 14/33* | (2006.01) |
| *C12N 15/70* | (2006.01) |
| *A61K 39/00* | (2006.01) |

(52) U.S. Cl.
CPC .......... *C07K 16/1282* (2013.01); *A61K 39/08* (2013.01); *C07K 14/33* (2013.01); *C12N 15/70* (2013.01); *A61K 39/00* (2013.01); *C07K 2319/40* (2013.01); *C07K 2319/55* (2013.01)

(58) Field of Classification Search
None
See application file for complete search history.

(56) References Cited

FOREIGN PATENT DOCUMENTS

| WO | 00/61762 | 10/2000 |
|---|---|---|
| WO | 2010/017383 | 2/2010 |

OTHER PUBLICATIONS

Yamamoto, et al., High level expression of *Streptococcus pyogenes* erythrogenic toxin A (SPE A) in *Escherichia coli* and its rapid purification by HPLC, FEMS Microbiology Letters (1995) 132(3):209-213.

Chaussee, et al., Streptococcal erythrogenic toxin B abrogates fibronectin-dependent internalization of *Streptococcus pyogenes* by cultured mammalian cells, Infection and Immunity (2000) 68(6):3226-3232.

Belyi, et al., Construction of a fusion protein carrying antigenic determinants of enteric clostridial toxins, FEMS Microbiology Letters (no longer published by Elsevier)), (2003) 225(2):325-329.

*Primary Examiner* — Jennifer Graser
(74) *Attorney, Agent, or Firm* — Virginia G. Campen

(57) ABSTRACT

Polynucleotides encoding fusion proteins comprising fragments of toxin A and toxin B from *Clostridium difficile* are described, as well as vectors and host cells containing such polynucleotides.

14 Claims, 32 Drawing Sheets

FIG. 1A

SEQ ID NO: 1 – sequence of toxin A

MSLISKEELIKLAYSIRPRENEYKTILTNLDEYNKLTTNNNENKYLQLKKLNESIDVFMN
KYKTSSRNRALSNLKKDILKEVILIKNSNTSPVEKNLHFVWIGGEVSDIALEYIKQWADI
NAEYNIKLWYDSEAFLVNTLKKAIVESSTTEALQLLEEEIQNPQFDNMKFYKKRMEFIYD
RQKRFINYYKSQINKPTVPTIDDIIKSHLVSEYNRDETVLESYRTNSLRKINSNHGIDIR
ANSLFTEQELLNIYSQELLNRGNLAAASDIVRLLALKNFGGVYLDVDMLPGIHSDLFKTI
SRPSSIGLDRWEMIKLEAIMKYKKYINNYTSENFDKLDQQLKDNFKLIIESKSEKSEIFS
KLENLNVSDLEIKIAFALGSVINQALISKQGSYLTNLVIEQVKNRYQFLNQHLNPAIESD
NNFTDTTKIFHDSLFNSATAENSMFLTKIAPYLQVGFMPEARSTISLSGPGAYASAYYDF
INLQENTIEKTLKASDLIEFKFPENNLSQLTEQEINSLWSFDQASAKYQFEKYVRDYTGG
SLSEDNGVDFNKNTALDKNYLLNNKIPSNNVEEAGSKNYVHYIIQLQGDDISYEATCNLF
SKNPKNSIIQRNMNESAKSYFLSDDGESILELNKYRIPERLKNKEKVKVTFIGHGKDEF
NTSEFARLSVDSLSNEISSFLDTIKLDISPKNVEVNLLGCNMFSYDFNVEETYPGKLLLS
IMDKITSTLPDVNKNSITIGANQYEVRINSEGRKELLAHSGKWINKEEAIMSDLSSKEYI
FFDSIDNKLKAKSKNIPGLASISEDIKTLLLDASVSPDTKFILNNLKLNIESSIGDYIYY
EKLEPVKNIIHNSIDDLIDEFNLLENVSDELYELKKLNNLDEKYLISFEDISKNNSTYSV
RFINKSNGESVYVETEKEIFSKYSEHITKEISTIKNSIITDVNGNLLDNIQLDHTSQVNT
LNAAFFIQSLIDYSSNKDVLNDLSTSVKVQLYAQLFSTGLNTIYDSIQLVNLISNAVNDT
INVLPTITEGIPIVSTILDGINLGAAIKELLDEHDPLLKKELEAKVGVLAINMSLSIAAT
VASIVGIGAEVTIFLLPIAGISAGIPSLVNNELILHDKATSVVNYFNHLSESKKYGPLKT
EDDKILVPIDDLVISEIDFNNNSIKLGTCNILAMEGGSGHTVTGNIDHFFSSPSISSHIP
SLSIYSAIGIETENLDFSKKIMMLPNAPSRVFWWETGAVPGLRSLENDGTRLLDSIRDLY
PGKFYWRFYAFFDYAITTLKPVYEDTNIKIKLDKDTRNFIMPTITTNEIRNKLSYSFDGA
GGTYSLLLSSYPISTNINLSKDDLWIFNIDNEVREISIENGTIKKGKLIKDVLSKIDINK
NKLIIGNQTIDFSGDIDNKDRYIFLTCELDDKISLIIEINLVAKSYSLLLSGDKNYLISN
LSNTIEKINTLGLDSKNIAYNYTDESNNKYFGAISKTSQKSIIHYKKDSKNILEFYNDST
LEFNSKDFIAEDINVFMKDDINTITGKYYVDNNTDKSIDFSISLVSKNQVKVNGLYLNES
VYSSYLDFVKNSDGHHNTSNFMNLFLDNISFWKLFGFENINFVIDKYFTLVGKTNLGYVE
FICDNNKNIDIYFGEWKTSSSKSTIFSGNGRNVVVEPIYNPDTGEDISTSLDFSYEPLYG
IDRYINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNFKSF
NSENELDRDHLGFKIIDNKTYYYDEDSKLVKGLININNSLFYFDPIEFNLVTGWQTINGK
KYYFDINTGAALTSYKIINGKHFYFNNDGVMQLGVFKGPDGFEYFAPANTQNNNIEGQAI
VYQSKFLTLNGKKYYFDNNSKAVTGWRIINNEKYYFNPNNAIAAVGLQVIDNNKYFNPD
TAIISKGWQTVNGSRYYFDTDTAIAFNGYKTIDGKHFYFDSDCVVKIGVFSTSNGFEYFA
PANTYNNNIEGQAIVYQSKFLTLNGKKYYFDNNSKAVTGLQTIDSKKYYFNTNTAEAATG
WQTIDGKKYYFNTNTAEAATGWQTIDGKKYYFNTNTAIASTGYTIINGKHFYFNTDGIMQ
IGVFKGPNGFEYFAPANTDANNIEGQAILYQNEFLTLNGKKYYFGSDSKAVTGWRIINNK
KYYFNPNNAIAAIHLCTINNDKYYFSYDGILQNGYITIERNNFYFDANNESKMVTGVFKG
PNGFEYFAPANTHNNNIEGQAIVYQNKFLTLNGKKYYFDNDSKAVTGWQTIDGKKYYFNL
NTAEAATGWQTIDGKKYYFNLNTAEAATGWQTIDGKKYYFNTNTFIASTGYTSINGKHFY
FNTDGIMQIGVFKGPNGFEYFAPANTDANNIEGQAILYQNKFLTLNGKKYYFGSDSKAVT
GLRTIDGKKYYFNTNTAVAVTGWQTINGKKYYFNTNTSIASTGYTIISGKHFYFNTDGIM
QIGVFKGPDGFEYFAPANTDANNIEGQAIRYQNRFLYLHDNIYYFGNNSKAATGWVTIDG
NRYYFEPNTAMGANGYKTIDNKNFYFRNGLPQIGVFKGSNGFEYFAPANTDANNIEGQAI
RYQNRFLHLLGKIYYFGNNSKAVTGWQTINGKVYYFMPDTAMAAAGGLFEIDGVIYFFGV
DGVKAPGIYG

FIG. 1 B

SEQ ID NO:2 – sequence of toxin B

MSLVNRKQLEKMANVRFRTQEDEYVAILDALEEYHNMSENTVVEKYLKLEDINSLTDIYI
DTYKKSGRNKALKKFKEYLVTEVLELKNNNLTPVEKNLHFVWIGGQINDTAINYINQWKD
VNSDYNVNVFYDSNAFLINTLKKTVVESAINDTLESFRENLNDPRFDYNKFFRKRMEIIY
DKQKNFINYYKAQREENPELIIDDIVKTYLSNEYSKEIDELNTYIEESLNKITQNSGNDV
RNFEEFKNGESFNLYEQELVERWNLAAASDILRISALKEIGGMYLDVDMLPGIQPDLFES
IEKPSSVTVDFWEMTKLEAIMKYKEYIPEYTSEHFDMLDEEVQSSFESVLASKSDKSEIF
SSLGDMEASPLEVKIAFNSKGIINQGLISVKDSYCSNLIVEQIENRYKILNNSLNPAISE
DNDFNTTTNTFIDSIMAEANADNGRFMMELGKYLRVGFFPDVKTTINLSGPEAYAAAYQD
LLMFKEGSMNIHLIEADLRNFEISKTNISQSTEQEMASLWSFDDARAKAQFEEYKRNYFE
GSLGEDDNLDFSQNIVVDKEYLLEKISSLARSSERGYIHYIVQLQGDKISYEAACNLFAK
TPYDSVLFQKNIEDSEIAYYYNPGDGEIQEIDKYKIPSIISDRPKIKLTFIGHGKDEFNT
DIFAGFDVDSLSTEIEAAIDLAKEDISPKSIEINLLGCNMFSYSINVEETYPGKLLLKVK
DKISELMPSISQDSIIVSANQYEVRINSEGRRELLDHSGEWINKEESIIFDISSKEYISF
NPKENKITVKSKNLPELSTLLQEIRNNSNSSDIELEEKVMLTECEINVISNIDTQIVEER
IEEAKNLTSDSINYIKDEFKLIESISDALCDLKQQNELEDSHFISFEDISETDEGFSIRF
INKETGESIFVETEKTIFSEYANHITEEISKIKGTIFDTVNGKLVEKVNLDTTHEVNTLN
AAFFIQSLIEYNSSKESLSNLSVAMKVQVYAQLFSTGLNTITDAAKVVELVSTALDETID
LLPTLSEGLPIIATIIDGVSLGAAIKELSETSDPLLRQEIEAKIGIMAVNLTTATTAIIT
SSLGIASGFSILLVPLAGISAGIPSLVNNELVLRDKATKVVDYFKHVSLVETEGVFTLLD
DKIMMPQDDLVISEIDFNNNSIVLGKCEIWRMEGGSGHTVTDDIDHFFSAPSITYREPHL
SIYDVLEVQKEELDLSKDLMVLFNAPNRVFAWETGWTPGLRSLENDGTKLLDRIRDNYEG
EFYWRYFAFIADALITTLKPRYEDTNIRINLDSNTRSFIVPIITTEYIREKLSYSFYGSG
GTYALSLSQYNMGINIELSESDVWIIDVDNVVRDVTIESDKIKKGDLIEGILSTLSIEEN
KIILNSHEINFSGEVNGSNGFVSLTFSILEGINAIIEVDLLSKSYKLLISGELKILMLNS
NHIQQKIDYIGFNSELQKNIPYSFVDSEGKENGFINGSTKEGLFVSELPDVVLISKVYMD
DSKPSFGYYSNNLKDVKVITKDNVNILTGYYLKDDIKISLSLTLQDEKTIKLNSVHLDES
GVAEILKFMNRKGNTNTSDSLMSFLESMNIKSIFVNFLQSNIKFILDANPIISGTTSIGQ
FEFICDENDNIQPYFIKFNTLETNYTLYVGNRQNMIVEPNYDLDDSGDISSTVINFSQKY
LYGIDSCVNKVVISPNIYTDEINITPVYETNNTYPEVIVLDANYINEKINVNINDLSIRY
VWSNDGNDFILMSTSEENKVSQVKIRFVNVFKDETLANKLSFNFSDKQDVPVSEIILSFT
PSYYEDGLIGYDLGLVSLYNEKFYINNFGMMVSGLIYINDSLYYFKPFVNNLITGFVTVG
DDKYYFNPINGGAASIGETIIDDKNYYFNQSGVLQTGVFSTEDGFKYFAPANTLDENLEG
EAIDFTGKLIIDENIYYFDDNYRGAVEWKELDGEMHYFSPETGKAFKGLNQIGDYKYYFN
SDGVMQKGFVSINDNKHYFDDSGVMKVGYTEIDGKHFYFAENGEMQIGVFNTEDGFKYFA
HHNEDLGNEEGEEISYSGILNFNNKIYYFDDSFTAVVGWKDLEDGSKYYFDEDTAEAYIG
LSLINDGQYYFNDDGIMQVGFVTINDKVFYFSDSGIIESGVQNIDDNYFYIDDNGIVQIG
VFDTSDGYKYFAPANTVNDNIYGQAVEYSGLVRVGEDVYYFGETYTIETGWIYDMENESD
KYYFNPETKKACKGINLIDDIKYYFDEKGIMRTGLISFENNNYYFNENGEMQFGYINTED
RMFYFGEDGVMQIGVFNTPDGFKYFAHQNTLDENFEGESINYTGWLDLDEKRYYFTDEYI
AATGSVIIDGEEYYFDPDTAQLVISE

FIG. 1 C

SEQ ID NO:3 – sequence of Fusion 1
MGWQTIDGKKYYFNTNTAIASTGYTIINGKHFYFNTDGIMQIGVFKGPNGFEYFAPANTDANNIEGQAILYQNEF
LTLNGKKYYFGSDSKAVTGWRIINNKKYYFNPNNAIAAIHLCTINNDKYYFSYDGILQNGYITIERNNFYFDANN
ESKMVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFE
YFAPANTDANNIEGQAILYQNKFLTLNGKKYYFGSDSKAVTGLRTIDGKKYYFNTNTAVAVTGWQTINGKKYYFN
TNTSIASTGYTIISGKHFYFNTDGIMQIGVFKGPDGFEYFAPANTDANNIEGQAIRYQNRFLYLHDNIYYFGNNS
KAATGWVTIDGNRYYFEPNTAMGANGYKTIDNKNFYFRNGLPQIGVFKGSNGFEYFAPANTDANNIEGQAIRYQN
RFLHLLGKIYYFGNNSKAVTGWQTINGKVYYFMPDTAMAAAGGLFEIDGVIYFFGVDGVKAPGFVSINDNKHYFD
DSGVMKVGYTEIDGKHFYFAENGEMQIGVFNTEDGFKYFAHHNEDLGNEEGEEISYSGILNFNNKIYYFDDSFTA
VVGWKDLEDGSKYYFDEDTAEAYIGLSLINDGQYYFNDDGIMQVGFVTINDKVFYFSDSGIIESGVQNIDDNYFY
IDDNGIVQIGVFDTSDGYKYFAPANTVNDNIYGQAVEYSGLVRVGEDVYYFGETYTIETGWIYDMENESDKYYFN
PETKKACKGINLIDDIKYYFDEKGIMRTGLISFENNNYYFNENGEMQFGYINIEDKMFYFGEDGVMQIGVFNTPD
GFKYFAHQNTLDENFEGESINYTGWLDLDEKRYYFTDEYIAATGSVIIDGEEYYFDPDTAQLVISE

FIG. 1 D

SEQ ID NO:4 – sequence of Fusion 2
MGWQTIDGKKYYFNTNTAIASTGYTIINGKHFYFNTDGIMQIGVFKGPNGFEYFAPANTDANNIEGQAILYQNEF
LTLNGKKYYFGSDSKAVTGWRIINNKKYYFNPNNAIAAIHLCTINNDKYYFSYDGILQNGYITIERNNFYFDANN
ESKMVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFE
YFAPANTDANNIEGQAILYQNKFLTLNGKKYYFGSDSKAVTGLRTIDGKKYYFNTNTAVAVTGWQTINGKKYYFN
TNTSIASTGYTIISGKHFYFNTDGIMQIGVFKGPDGFEYFAPANTDANNIEGQAIRYQNRFLYLHDNIYYFGNNS
KAATGWVTIDGNRYYFEPNTAMGANGYKTIDNKNFYFRNGLPQIGVFKGSNGFEYFAPANTDANNIEGQAIRYQN
RFLHLLGKIYYFGNNSKAVTGWQTINGKVYYFMPDTAMAAAGGLNQIGDYKYYFNSDGVMQKGFVSINDNKHYFD
DSGVMKVGYTEIDGKHFYFAENGEMQIGVFNTEDGFKYFAHHNEDLGNEEGEEISYSGILNFNNKIYYFDDSFTA
VVGWKDLEDGSKYYFDEDTAEAYIGLSLINDGQYYFNDDGIMQVGFVTINDKVFYFSDSGIIESGVQNIDDNYFY
IDDNGIVQIGVFDTSDGYKYFAPANTVNDNIYGQAVEYSGLVRVGEDVYYFGETYTIETGWIYDMENESDKYYFN
PETKKACKGINLIDDIKYYFDEKGIMRTGLISFENNNYYFNENGEMQFGYINIEDKMFYFGEDGVMQIGVFNTPD
GFKYFAHQNTLDENFEGESINYTGWLDLDEKRYYFTDEYIAATGSVIIDGEEYYFDPDTAQLVISE

FIG. 1 E

SEQ ID NO:5 – sequence of Fusion 3
MGWQTIDGKKYYFNTNTAIASTGYTIINGKHFYFNTDGIMQIGVFKGPNGFEYFAPANTDANNIEGQAILYQNEF
LTLNGKKYYFGSDSKAVTGWRIINNKKYYFNPNNAIAAIHLCTINNDKYYFSYDGILQNGYITIERNNFYFDANN
ESKMVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFE
YFAPANTDANNIEGQAILYQNKFLTLNGKKYYFGSDSKAVTGLRTIDGKKYYFNTNTAVAVTGWQTINGKKYYFN
TNTSIASTGYTIISGKHFYFNTDGIMQIGVFKGPDGFEYFAPANTDANNIEGQAIRYQNRFLYLHDNIYYFGNNS
KAATGWVTIDGNRYYFEPNTAMGANGYKTIDNKNFYFRNGLPQIGVFKGSNGFEYFAHHNEDLGNEEGEEISYSG
ILNFNNKIYYFDDSFTAVVGWKDLEDGSKYYFDEDTAEAYIGLSLINDGQYYFNDDGIMQVGFVTINDKVFYFSD
SGIIESGVQNIDDNYFYIDDNGIVQIGVFDTSDGYKYFAPANTVNDNIYGQAVEYSGLVRVGEDVYYFGETYTIE
TGWIYDMENESDKYYFNPETKKACKGINLIDDIKYYFDEKGIMRTGLISFENNNYYFNENGEMQFGYINIEDKMF
YFGEDGVMQIGVFNTPDGFKYFAHQNTLDENFEGESINYTGWLDLDEKRYYFTDEYIAATGSVIIDGEEYYFDPD
TAQLVISE

FIG. 1 F

SEQ ID NO:6 – sequence of Fusion 4

MGWQTIDGKKYYFNTNTAIASTGYTIINGKHFYFNTDGIMQIGVFKGPNGFEYFAPANTDANNIEGQAILYQNEF
LTLNGKKYYFGSDSKAVTGWRIINNKKYYFNPNNAIAAIHLCTINNDKYYFSYDGILQNGYITIERNNFYFDANN
ESKMVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFE
YFAPANTDANNIEGQAILYQNKFLTLNGKKYYFGSDSKAVTGLRTIDGKKYYFNTNTAVAVTGWQTINGKKYYFN
TNTSIASTGYTIISGKHFYFNTDGIMQIGVFKGPDGFEYFAPANTDANNIEGQAIRYQNRFLYLHDNIYYFGNNS
KAATGWVTIDGNRYYFEPNTAMGANGYKTIDNKNFYFRNGLPQIGVFKGSNGFEYFAPANTDANNIEGQAIRYQN
RFLHLLGKIYYFGNNSKAVTGWQTINGKVYYFMPDTAMAAAGGETIIDDKNYYFNQSGVLQTGVFSTEDGFKYFA
PANTLDENLEGEAIDFTGKLIIDENIYYFDDNYRGAVEWKELDGEMHYFSPETGKAFKGLNQIGDYKYYFNSDGV
MQKGFVSINDNKHYFDDSGVMKVGYTEIDGKHFYFAENGEMQIGVFNTEDGFKYFAHHNEDLGNEEGEEISYSGI
LNFNNKIYYFDDSFTAVVGWKDLEDGSKYYFDEDTAEAYIGLSLINDGQYYFNDDGIMQVGFVTINDKVFYFSDS
GIIESGVQNIDDNYFYIDDNGIVQIGVFDTSDGYKYFAPANTVNDNIYGQAVEYSGLVRVGEDVYYFGETYTIET
GWIYDMENESDKYYFNPETKKACKGINLIDDIKYYFDEKGIMRTGLISFENNNYYFNENGEMQFGYINIEDKMFY
FGEDGVMQIGVFNTPDGFKYFAHQNTLDENFEGESINYTGWLDLDEKRYYFTDEYIAATGSVIIDGEEYYFDPDT
AQLVISE

FIG. 1 G

SEQ ID NO:7 – sequence of Fusion 5

MGWQTIDGKKYYFNTNTAIASTGYTIINGKHFYFNTDGIMQIGVFKGPNGFEYFAPANTDANNIEGQAILYQNEF
LTLNGKKYYFGSDSKAVTGWRIINNKKYYFNPNNAIAAIHLCTINNDKYYFSYDGILQNGYITIERNNFYFDANN
ESKMVTGVFKGPNGFEYFAPANTHNNNIEGQAIVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFE
YFAPANTDANNIEGQAILYQNKFLTLNGKKYYFGSDSKAVTGLRTIDGKKYYFNTNTAVAVTGWQTINGKKYYFN
TNTSIASTGYTIISGKHFYFNTDGIMQIGVFKGPDGFEYFAPANTDANNIEGQAIRYQNRFLYLHDNIYYFGNNS
KAATGWVTIDGNRYYFEPNTAMGANGYKTIDNKNFYFRNGLPQIGVFKGSNGFEYFAPANTDANNIEGQAIRYQN
RFLHLLGKIYYFGNNSKAVTGWQTINGKVYYFMPDTAMAAAGGLFEIDGVIYFFGVDGVKAPGIYGGGFVSINDN
KHYFDDSGVMKVGYTEIDGKHFYFAENGEMQIGVFNTEDGFKYFAHHNEDLGNEEGEEISYSGILNFNNKIYYFD
DSFTAVVGWKDLEDGSKYYFDEDTAEAYIGLSLINDGQYYFNDDGIMQVGFVTINDKVFYFSDSGIIESGVQNID
DNYFYIDDNGIVQIGVFDTSDGYKYFAPANTVNDNIYGQAVEYSGLVRVGEDVYYFGETYTIETGWIYDMENESD
KYYFNPETKKACKGINLIDDIKYYFDEKGIMRTGLISFENNNYYFNENGEMQFGYINIEDKMFYFGEDGVMQIGV
FNTPDGFKYFAHQNTLDENFEGESINYTGWLDLDEKRYYFTDEYIAATGSVIIDGEEYYFDPDTAQLVISE

FIG. 1 H

SEQ ID NO:8 sequence of individual toxin A fragment

MASTGYTSINGKHFYFNTDGIMQIGVFKGPNGFEYFAPANTDANNIEGQAILYQNKFLTLNGKKYYFGSDSKAVT
GLRTIDGKKYYFNTNTAVAVTGWQTINGKKYYFNTNTSIASTGYTIISGKHFYFNTDGIMQIGVFKGPDGFEYFA
PANTDANNIEGQAIRYQNRFLYLHDNIYYFGNNSKAATGWVTIDGNRYYFEPNTAMGANGYKTIDNKNFYFRNGL
PQIGVFKGSNGFEYFAPANTDANNIEGQAIRYQNRFLHLLGKIYYFGNNSKAVTGWQTINGKVYYFMPDTAMAAA
GGLFEIDGVIYFFGVDGVKAP

FIG. 1 I

SEQ ID NO:9 – sequence of individual toxin B fragment

MILMSTSEENKVSQVKIRFVNVFKDKTLANKLSFNFSDKQDVPVSEIILSFTPSYYEDGLIGYDLGLVSLYNEKF
YINNFGMMVSGLIYINDSLYYFKPPVNNLITGFVTVGDDKYYFNPINGGAASIGETIIDDKNYYFNQSGVLQTGV
FSTEDGFKYFAPANTLDENLEGEAIDFTGKLIIDENIYYFDDNYRGAVEWKELDGEMHYFSPETGKAFKGLNQIG
DYKYYFNSDGVMQKGFVSINDNKHYFDDSGVMKVGYTEIDGKHFYFAENGEMQIGVFNTEDGFKYFAHHNEDLGN
EEGEEISYSGILNFNNKIYYFDDSFTAVVGWKDLEDGSKYYFDEDTAEAYIGLSLINDGQYYFNDDGIMQVGFVT
INDKVFYFSDSGIIESGVQNIDDNYFYIDDNGIVQIGVFDTSDGYKYFAPANTVNDNIYGQAVEYSGLVRVGEDV
YYFGETYTIETGWIYDMENESDKYYFNPETKKACKGINLIDDIKYYFDEKGIMRTGLISFENNNYYFNENGEMQF
GYINIEDKMFYFGEDGVMQIGVFNTPDGFKYFAHQNTLDENFEGESINYTGWLDLDEKRYYFTDEYIAATGSVII
DGEEYYFDPDTA

FIG. 1J

SEQ ID NO:10 – nucleotide sequence of F54 Gly

ATGGCAACCGGTTGGCAGACCATCGATGGCAAAAAATATTATTTTAATACCAACACCGCAATTGCAAGCACCGGC
TATACCATTATCAACGGCAAACACTTTTATTTTAACACCGACGGCATTATGCAGATTGGTGTGTTTAAAGGTCCG
AACGGCTTTGAATACTTTGCACCGGCAAATACCGATGCCAATAATATTGAAGGCCAGGCCATTCTGTATCAGAAT
GAATTTCTGACCCTGAACGGCAAAAAATACTACTTTGGCAGCGATAGCAAAGCAGTTACCGGTTGGCGCATCATC
AACAATAAGAAATATTACTTCAACCCGATAATGCAATTGCAGCAATTCATCTGTGCACCATTAACAACGACAAA
TATTATTTCAGCTATGACGGTATTCTGCAGAATGGCTACATTACCATCGAACGCAACAACTTTTATTTCGATGCC
AACAACGAAAGCAAAATGGTGACCGGTGTTTTCAAAGGCCCTAATGGTTTTGAGTATTTCGCTCCGGCAAACACC
CATAATAACAACATTGAAGGTCAGGCGATCGTTTATCAGAACAAATTCCTGACGCTGAATGGTAAGAAATACTAT
TTCGATAATGACAGCAAAGCCGTGACCGGCTGGCAGACAATTGACGGGAAGAAATATTACTTTAATCTGAATACC
GCAGAAGCAGCAACCGGTTGGCAAACGATCGACGGTAAAAAGTACTACTTCAACCTGAACACAGCCGAAGCAGCC
ACAGGATGGCAGACTATTGATGGAAAAAAATACTATTTCAACACCAACACCTTTATTGCATCTACCGGTTATACC
AGCATTAACGGTAAACATTTCTACTTCAACACCGATGGTATCATGCAGATCGGCGTTTTCAAAGGTCCAAATGGT
TTCGAATACTTTGCCCCTGCCAATACAGATGCAAATAACATCGAGGGTCAGGCAATCCTGTACCAAAACAAATTT
CTGACCCTGAATGGGAAAAAATATTACTTTGGTAGCGATTCTAAAGCCGTTACCGGTCTGCGTACCATTGATGGT
AAAAAATACTACTTTAATACGAATACAGCCGTTGCGGTTACAGGCTGGCAGACCATTAACGGGAAAAAATACTAT
TTTAACACAAATACCAGCATTGCCTCAACGGGTTATACCATTATTTCGGGTAAACACTTCTACTTTAATACCGAT
GGTATTATGCAAATCGGAGTCTTTAAAGGACCTGATGGGTTCGAATATTTTGCGCCTGCGAACACTGATGCGAAC
AATATCGAAGGACAGGCAATCCGCTATCAGAATCGCTTTCTGTATCTGCACGACAACATCTATTATTTTGGCAAC
AATTCAAAAGCAGCCACCGGCTGGGTTACAATTGATGGCAACCGCTACTATTTCGAACCGAATACCGCAATGGGT
GCAAATGGCTACAAAACCATCGATAATAAAAATTTCTATTTTCGCAACGGTCTGCCGCAGATCGGGGTATTTAAA
GGTAGCAACGGCTTCGAATACTTCGCTCCAGCGAATACGGACGCGAACAATATTGAGGGTCAAGCGATTCGTTAT
CAAAACCGTTTTCTGCATCTGCTGGGCAAAATCTACTACTTTGGCAATAACAGTAAAGCAGTTACTGGATGGCAG
ACAATCAATGGTAAAGTGTACTATTTTATGCCGGATACCGCCATGGCAGCAGCCGGTGGTCTGTTTGAAATTGAT
GGCGTGATCTATTTTTTTGGTGTGGATGGTGTTAAAGCACCGGGAATATACGGTGGTACCGGCTTTGTGACCGTG
GGTGATGATAAATACTATTTCAATCCGATTAACGGTGGTGCAGCGAGCATTGGCGAAACCATCATCGATGACAAA
AACTATTATTTCAACCAGAGCGGTGTGCTGCAGACCGGTGTGTTTAGCACCGAAGATGGCTTTAAATATTTTGCG
CCAGCGAACACCCTGGATGAAAACCTGGAAGGCGAAGCGATTGATTTTACCGGCAAACTGATCATCGATGAAAAC
ATCTATTACTTCGATGATAACTATCGTGGTGCGGTGGAATGGAAAGAACTGGATGGCGAAATGCATTATTTTTCT
CCGGAAACCGGTAAAGCGTTTAAAGGCCTGAACCAGATCGGCGATTACAAATACTACTTCAACAGCGATGGCGTG
ATGCAGAAAGGCTTTGTGAGCATCAACGATAACAAACACTATTTCGATGATAGCGGTGTGATGAAAGTGGGCTAT
ACCGAAATTGATGGCAAACATTTCTACTTCGCGGAAAACGGCGAAATGCAGATTGGCGTGTTCAATACCGAAGAT
GGTTTCAAATACTTCGCGCACCATAACGAAGATCTGGGTAACGAAGAAGGCGAAGAAATTAGCTATAGCGGCATC
CTGAACTTCAACAACAAAATCTACTACTTTGATGATAGCTTTACCGCGGTGGTGGGCTGGAAAGATCTGGAAGAT
GGCAGCAAATATTATTTCGATGAAGATACCGCGGAAGCGTATATTGGCCTGAGCCTGATTAACGATGGCCAGTAC
TATTTTAACGATGATGGCATTATGCAGGTGGGTTTCGTGACCATTAATGATAAAGTGTTCTATTTCAGCGATAGC
GGCATTATTGAAAGCGGCGTGCAGAACATTGATGATAACTACTTCTACATCGATGATAACGGCATTGTGCAGATC
GGCGTTTTTGATACCAGCGATGGCTACAAATATTTCGCACCGGCCAATACCGTGAACGATAACATTTATGGCCAG
GCGGTGGAATATAGCGGTCTGGTGCGTGTGGGCGAAGATGTGTATTATTTCGGCGAAACCTATACCATCGAAACC
GGCTGGATTTATGATATGGAAAACGAAAGCGATAAATATTACTTTAATCCGGAAACGAAAAAAGCGTGCAAAGGC
ATTAACCTGATCGATGATATCAAATACTATTTTGATGAAAAAGGCATTATGCGTACCGGTCTGATTAGCTTCGAA
AACAACAACTATTACTTCAACGAAAACGGTGAAATGCAGTTCGGCTACATCAACATCGAAGATAAAATGTTCTAC
TTCGGCGAAGATGGTGTTATGCAGATTGGTGTTTTTAACACCCCGGATGGCTTCAAATACTTTGCCCATCAGAAT
ACCCTGGATGAAAATTTCGAAGGTGAAAGCATTAACTATACCGGCTGGCTGGATCTGGATGAAAAACGCTACTAC
TTCACCGATGAATACATTGCGGCGACCGGCAGCGTGATTATTGATGGCGAAGAATACTACTTCGATCCGGATACC
GCGCAGCTGGTGATTAGCGAACATCATCATCATCACCAT

FIG. 1 K

SEQ ID NO :11 – amino acid of F54Gly

MATGWQTIDGKKYYFNTNTAIASTGYTIINGKHFYFNTDGIMQIGVFKGPNGFEYFAPANTDANNIEGQAILYQN
EFLTLNGKKYYFGSDSKAVTGWRIINNKKYYFNPNNAIAAIHLCTINNDKYYFSYDGILQNGYITIERNNFYFDA
NNESKMVTGVFKGPNGFEYFAPANTHNNNIEGQAIVYQNKFLTLNGKKYYFDNDSKAVTGWQTIDGKKYYFNLNT
AEAATGWQTIDGKKYYFNLNTAEAATGWQTIDGKKYYFNTNTFIASTGYTSINGKHFYFNTDGIMQIGVFKGPNG
FEYFAPANTDANNIEGQAILYQNKFLTLNGKKYYFGSDSKAVTGLRTIDGKKYYFNTNTAVAVTGWQTINGKKYY
FNTNTSIASTGYTIISGKHFYFNTDGIMQIGVFKGPDGFEYFAPANTDANNIEGQAIRYQNRFLYLHDNIYYFGN
NSKAATGWVTIDGNRYYFEPNTAMGANGYKTIDNKNFYFRNGLPQIGVFKGSNGFEYFAPANTDANNIEGQAIRY
QNRFLHLLGKIYYFGNNSKAVTGWQTINGKVYYFMPDTAMAAAGGLFEIDGVIYFFGVDGVKAPGIYGGTGFVTV
GDDKYYFNPINGGAASIGETIIDDKNYYFNQSGVLQTGVFSTEDGFKYFAPANTLDENLEGEAIDFTGKLIIDEN
IYYFDDNYRGAVEWKELDGEMHYFSPETGKAFKGLNQIGDYKYYFNSDGVMQKGFVSINDNKHYFDDSGVMKVGY
TEIDGKHFYFAENGEMQIGVFNTEDGFKYFAHHNEDLGNEEGEEISYSGILNFNNKIYYFDDSFTAVVGWKDLED
GSKYYFDEDTAEAYIGLSLINDGQYYFNDDGIMQVGFVTINDKVFYFSDSGIIESGVQNIDDNYFYIDDNGIVQI
GVFDTSDGYKYFAPANTVNDNIYGQAVEYSGLVRVGEDVYYFGETYTIETGWIYDMENESDKYYFNPETKKACKG
INLIDDIKYYFDEKGIMRTGLISFENNNYYFNENGEMQFGYINIEDKMFYFGEDGVMQIGVFNTPDGFKYFAHQN
TLDENFEGESINYTGWLDLDEKRYYFTDEYIAATGSVIIDGEEYYFDPDTAQLVISEHHHHHH

FIG. 1 L

SEQ ID NO :12 – nucleotide sequence of F54 New

ATGGCAACCGGTTGGCAGACCATCGATGGCAAAAAATATTATTTTAATACCAACACCGCAATTGCAAGCACCGGC
TATACCATTATCAACGGCAAACACTTTTATTTTAACACCGACGGCATTATGCAGATTGGTGTGTTTAAAGGTCCG
AACGGCTTTGAATACTTTGCACCGGCAAATACCGATGCCAATAATATTGAAGGCCAGGCCATTCTGTATCAGAAT
GAATTTCTGACCCTGAACGGCAAAAAATACTACTTTGGCAGCGATAGCAAAGCAGTTACCGGTTGGCGCATCATC
AACAATAAGAAATATTACTTCAACCCGAATAATGCAATTGCAGCAATTCATCTGTGCACCATTAACAACGACAAA
TATTATTTCAGCTATGACGGTATTCTGCAGAATGGCTACATTACCATCGAACGCAACAACTTTTATTTCGATGCC
AACAACGAAAGCAAATGGTGACCGGTGTTTTCAAAGGCCCTAATGGTTTTGAGTATTTCGCTCCGGCAAACACC
CATAATAACAACATTGAAGGTCAGGCGATCGTTTATCAGAACAAATTCCTGACGCTGAATGGTAAGAAATACTAT
TTCGATAATGACAGCAAAGCCGTGACCGGCTGGCAGACAATTGACGGGAAGAAATATTACTTTAATCTGAATACC
GCAGAAGCAGCAACCGGTTGGCAAACGATCGACGGTAAAAAGTACTACTTCAACCTGAACACAGCCGAAGCAGCC
ACAGGATGGCAGACTATTGATGGAAAAAAATACTATTTCAACACCAACACCTTTATTGCATCTACCGGTTATACC
AGCATTAACGGTAAACATTTCTACTTCAACACCGATGGTATCATGCAGATCGGCGTTTTCAAAGGTCCAAATGGT
TTCGAATACTTTGCCCCTGCCAATACAGATGCAAATAACATCGAGGGTCAGGCAATCCTGTACCAAAACAAATTT
CTGACCCTGAATGGGAAAAAATATTACTTTGGTAGCGATTCTAAAGCCGTTACCGGTCTGCGTACCATTGATGGT
AAAAAATACTACTTTAATACGAATACAGCCGTTGCGGTTACAGGCTGGCAGACCATTAACGGGAAAAAATACTAT
TTTAACACAAATACCAGCATTGCCTCAACGGGTTATACCATTATTTCGGGTAAACACTTCTACTTTAATACCGAT
GGTATTATGCAAATCGGAGTCTTTAAAGGACCTGATGGGTTCGAATATTTTGCGCCTGCGAACACTGATGCGAAC
AATATCGAAGGACAGGCAATCCGCTATCAGAATCGCTTTCTGTATCTGCACGACAACATCTATTATTTTGGCAAC
AATTCAAAAGCAGCCACCGGCTGGGTTACAATTGATGGCAACCGCTACTATTTCGAACCGAATACCGCAATGGGT
GCAAATGGCTACAAAACCATCGATAATAAAAATTTCTATTTTCGCAACGGTCTGCCGCAGATCGGGGTATTTAAA
GGTAGCAACGGCTTCGAATACTTCGCTCCAGCGAATACGGACGCGAACAATATTGAGGGTCAAGCGATTCGTTAT
CAAAACCGTTTTCTGCATCTGCTGGGCAAAATCTACTACTTTGGCAATAACAGTAAAGCAGTTACTGGATGGCAG
ACAATCAATGGTAAAGTGTACTATTTTATGCCGGATACCGCCATGGCAGCAGCCGGTGGTCTGTTTGAAATTGAT
GGCGTGATCTATTTTTTTGGTGTGGATGGTGTTAAAGCAGTTACCGGCTTTGTGACCGTGGGTGATGATAAATAC
TATTTCAATCCGATTAACGGTGGTGCAGCGAGCATTGGCGAAACCATCATCGATGACAAAAACTATTATTTCAAC
CAGAGCGGTGTGCTGCAGACCGGTGTGTTTAGCACCGAAGATGGCTTTAAATATTTTGCGCCAGCGAACACCCTG
GATGAAAACCTGGAAGGCGAAGCGATTGATTTTACCGGCAAACTGATCATCGATGAAAACATCTATTACTTCGAT
GATAACTATCGTGGTGCGGTGGAATGGAAAGAACTGGATGGCGAAATGCATTATTTTTCTCCGGAAACCGGTAAA
GCGTTTAAAGGCCTGAACCAGATCGGCGATTACAAATACTACTTCAACAGCGATGGCGTGATGCAGAAAGGCTTT
GTGAGCATCAACGATAACAAACACTATTTCGATGATAGCGGTGTGATGAAAGTGGGCTATACCGAAATTGATGGC
AAACATTTCTACTTCGCGGAAAACGGCGAAATGCAGATTGGCGTGTTCAATACCGAAGATGGTTTCAAATACTTC
GCGCACCATAACGAAGATCTGGGTAACGAAGAAGGCGAAGAAATTAGCTATAGCGGCATCCTGAACTTCAACAAC
AAAATCTACTACTTTGATGATAGCTTTACCGCGGTGGTGGGCTGGAAAGATCTGGAAGATGGCAGCAAATATTAT
TTCGATGAAGATACCGCGGAAGCGTATATTGGCCTGAGCCTGATTAACGATGGCCAGTACTATTTTAACGATGAT
GGCATTATGCAGGTGGGTTTCGTGACCATTAATGATAAAGTGTTCTATTTCAGCGATAGCGGCATTATTGAAAGC
GGCGTGCAGAACATTGATGATAACTACTTCTACATCGATGATAACGGCATTGTGCAGATCGGCGTTTTTGATACC
AGCGATGGCTACAAATATTTCGCACCGGCCAATACCGTGAACGATAACATTTATGCCAGGCGGTGGAATATAGC
GGTCTGGTGCGTGTGGGCGAAGATGTGTATTATTTCGGCGAAACCTATACCATCGAAACCGGCTGGATTTATGAT
ATGGAAAACGAAAGCGATAAATATTACTTTAATCCGGAAACGAAAAAAGCGTGCAAAGGCATTAACCTGATCGAT
GATATCAAATACTATTTTGATGAAAAGGCATTATGCGTACCGGTCTGATTAGCTTCGAAAACAACAACTATTAC
TTCAACGAAAACGGTGAAATGCAGTTCGGCTACATCAACATCGAAGATAAAATGTTCTACTTCGGCGAAGATGGT
GTTATGCAGATTGGTGTTTTAACACCCCGGATGGCTTCAAATACTTTGCCCATCAGAATACCCTGGATGAAAAT
TTCGAAGGTGAAAGCATTAACTATACCGGCTGGCTGGATCTGATGAAAAACGCTACTACTTCACCGATGAATAC
ATTGCGGCGACCGGCAGCGTGATTATTGATGGCGAAGAATACTACTTCGATCCGGATACCGCGCAGCTGGTGATT
AGCGAACATCATCATCATCACCAT

FIG. 1 M

SEQ ID NO :13 amino acid sequence of F54 New

MATGWQTIDGKKYYFNTNTAIASTGYTIINGKHFYFNTDGIMQIGVFKGPNGFEYFAPANTDANNIEGQAILYQN
EFLTLNGKKYYFGSDSKAVTGWRIINNKKYYFNPNNAIAAIHLCTINNDKYYFSYDGILQNGYITIERNNFYFDA
NNESKMVTGVFKGPNGFEYFAPANTHNNNIEGQAIVYQNKFLTLNGKKYYFDNDSKAVTGWQTIDGKKYYFNLNT
AEAATGWQTIDGKKYYFNLNTAEAATGWQTIDGKKYYFNTNTFIASTGYTSINGKHFYFNTDGIMQIGVFKGPNG
FEYFAPANTDANNIEGQAILYQNKFLTLNGKKYYFGSDSKAVTGLRTIDGKKYYFNTNTAVAVTGWQTINGKKYY
FNTNTSIASTGYTIISGKHFYFNTDGIMQIGVFKGPDGFEYFAPANTDANNIEGQAIRYQNRFLYLHDNIYYFGN
NSKAATGWVTIDGNRYYFEPNTAMGANGYKTIDNKNFYFRNGLPQIGVFKGSNGFEYFAPANTDANNIEGQAIRY
QNRFLHLLGKIYYFGNNSKAVTGWQTINGKVYYFMPDTAMAAAGGLFEIDGVIYFFGVDGVKAVTGFVTVGDDKY
YFNPINGGAASIGETIIDDKNYYFNQSGVLQTGVFSTEDGFKYFAPANTLDENLEGEAIDFTGKLIIDENIYYFD
DNYRGAVEWKELDGEMHYFSPETGKAFKGLNQIGDYKYYFNSDGVMQKGFVSINDNKHYFDDSGVMKVGYTEIDG
KHFYFAENGEMQIGVFNTEDGFKYFAHENEDLGNEEGEEISYSGILNFNNKIYYFDDSFTAVVGWKDLEDGSKYY
FDEDTAEAYIGLSLINDGQYYFNDDGIMQVGFVTINDKVFYFSDSGIIESGVQNIDDNYFYIDDNGIVQIGVFDT
SDGYKYFAPANTVNDNIYGQAVEYSGLVRVGEDVYYFGETYTIETGWIYDMENESDKYYFNPETKKACKGINLID
DIKYYFDEKGIMRTGLISFENNNYYFNENGEMQFGYINIEDKMFYFGEDGVMQIGVFNTPDGFKYFAHQNTLDEN
FEGESINYTGWLDLDEKRYYFTDEYIAATGSVIIDGEEYYFDPDTAQLVISEHHHHHH

FIG. 1 N

SEQ ID NO :14 nucleotide sequence of F5 ToxB

ATGGCAACCGGTTGGCAGACCATCGATGGCAAAAAATATTATTTTAATACCAACACCGCAATTGCAAGCACCGGC
TATACCATTATCAACGGCAAACACTTTTATTTTAACACCGACGGCATTATGCAGATTGGTGTGTTTAAAGGTCCG
AACGGCTTTGAATACTTTGCACCGGCAAATACCGATGCCAATAATATTGAAGGCCAGGCCATTCTGTATCAGAAT
GAATTTCTGACCCTGAACGGCAAAAAATACTACTTTGGCAGCGATAGCAAAGCAGTTACCGGTTGGCGCATCATC
AACAATAAGAAATATTACTTCAACCCGAATAATGCAATTGCAGCAATTCATCTGTGCACCATTAACAACGACAAA
TATTATTTCAGCTATGACGGTATTCTGCAGAATGGCTACATTACCATCGAACGCAACAACTTTTATTTCGATGCC
AACAACGAAAGCAAAATGGTGACCGGTGTTTTCAAAGGCCCTAATGGTTTTGAGTATTTCGCTCCGGCAAACACC
CATAATAACAACATTGAAGGTCAGGCGATCGTTTATCAGAACAAATTCCTGACGCTGAATGGTAAGAAATACTAT
TTCGATAATGACAGCAAAGCCGTGACCGGCTGGCAGACAATTGACGGGAAGAAATATTACTTTAATCTGAATACC
GCAGAAGCAGCAACCGGTTGGCAAACGATCGACGGTAAAAAGTACTACTTCAACCTGAACACAGCCGAAGCAGCC
ACAGGATGGCAGACTATTGATGGAAAAAAATACTATTTCAACACCAACACCTTTATTGCATCTACCGGTTATACC
AGCATTAACGGTAAACATTTCTACTTCAACACCGATGGTATCATGCAGATCGGCGTTTTCAAAGGTCCAAATGGT
TTCGAATACTTTGCCCCTGCCAATACAGATGCAAATAACATCGAGGGTCAGGCAATCCTGTACCAAAACAAATTT
CTGACCCTGAATGGGAAAAAATATTACTTTGGTAGCGATTCTAAAGCCGTTACCGGTCTGCGTACCATTGATGGT
AAAAAATACTACTTTAATACGAATACAGCCGTTGCGGTTACAGGCTGGCAGACCATTAACGGGAAAAAATACTAT
TTTAACACAAATACCAGCATTGCCTCAACGGGTTATACCATTATTTCGGGTAAACACTTCTACTTTAATACCGAT
GGTATTATGCAAATCGGAGTCTTTAAAGGACCTGATGGGTTCGAATATTTTGCGCCTGCGAACACTGATGCGAAC
AATATCGAAGGACAGGCAATCCGCTATCAGAATCGCTTTCTGTATCTGCACGACAACATCTATTATTTTGGCAAC
AATTCAAAAGCAGCCACCGGCTGGGTTACAATTGATGGCAACCGCTACTATTTCGAACCGAATACCGCAATGGGT
GCAAATGGCTACAAAACCATCGATAATAAAAATTTCTATTTTCGCAACGGTCTGCCGCAGATCGGGGTATTTAAA
GGTAGCAACGGCTTCGAATACTTCGCTCCAGCGAATACGGACGCGAACAATATTGAGGGTCAAGCGATTCGTTAT
CAAAACCGTTTTCTGCATCTGCTGGGCAAAATCTACTACTTTGGCAATAACAGTAAAGCAGTTACTGGATGGCAG
ACAATCAATGGTAAAGTGTACTATTTTATGCCGGATACCGCCATGGCAGCAGCCGGTGGTCTGTTTGAAATTGAT
GGCGTGATCTATTTTTTTGGTGTGGATGGTGTTAAAGCAGTGAGCGGTCTGATTTATATTAACGATAGCCTGTAT
TACTTTAAACCACCGGTGAATAACCTGATTACCGGCTTTGTGACCGTGGGTGATGATAAATACTATTTCAATCCG
ATTAACGGTGGTGCAGCGAGCATTGGCGAAACCATCATCGATGACAAAAACTATTATTTCAACCAGAGCGGTGTG
CTGCAGACCGGTGTGTTTAGCACCGAAGATGGCTTTAAATATTTTGCGCCAGCGAACACCCTGGATGAAACCTG
GAAGGCGAAGCGATTGATTTTACCGGCAAACTGATCATCGATGAAAACATCTATTACTTCGATGATAACTATCGT
GGTGCGGTGGAATGGAAAGAACTGGATGGCGAAATGCATTATTTTCTCCGGAAACCGGTAAAGCGTTTAAAGGC
CTGAACCAGATCGGCGATTACAAATACTACTTCAACAGCGATGGCGTGATGCAGAAAGGCTTTGTGAGCATCAAC
GATAACAAACACTATTTCGATGATAGCGGTGTGATGAAAGTGGGCTATACCGAAATTGATGGCAAACATTTCTAC
TTCGCGGAAAACGGCGAAATGCAGATTGGCGTGTTCAATACCGAAGATGGTTTCAAATACTTCGCGCACCATAAC
GAAGATCTGGGTAACGAAGAAGGCGAAGAAATTAGCTATAGCGGCATCCTGAACTTCAACAACAAAATCTACTAC
TTTGATGATAGCTTTACCGCGGTGGTGGGCTGGAAAGATCTGGAAGATGGCAGCAAATATTATTTCGATGAAGAT
ACCGCGGAAGCGTATATTGGCCTGAGCCTGATTAACGATGGCCAGTACTATTTTAACGATGATGGCATTATGCAG
GTGGGTTTCGTGACCATTAATGATAAAGTGTTCTATTTCAGCGATAGCGGCATTATTGAAAGCGGCGTGCAGAAC
ATTGATGATAACTACTTCTACATCGATGATAACGGCATTGTGCAGATCGGCGTTTTTGATACCAGCGATGGCTAC
AAATATTTCGCACCGGCCAATACCGTGAACGATAACATTTATGGCCAGGCGGTGGAATATAGCGGTCTGGTGCGT
GTGGGCGAAGATGTGTATTATTTCGGCGAAACCTATACCATCGAAACCGGCTGGATTTATGATATGGAAAACGAA
AGCGATAAATATTACTTTAATCCGGAAACGAAAAAGCGTGCAAAGGCATTAACCTGATCGATGATATCAAATAC
TATTTTGATGAAAAAGGCATTATGCGTACCGGTCTGATTAGCTTCGAAAACAACAACTATTACTTCAACGAAAAC
GGTGAAATGCAGTTCGGCTACATCAACATCGAAGATAAAATGTTCTACTTCGGCGAAGATGGTGTTATGCAGATT
GGTGTTTTTAACACCCCGGATGGCTTCAAATACTTTGCCCATCAGAATACCCTGGATGAAAATTTCGAAGGTGAA
AGCATTAACTATACCGGCTGGCTGGATCTGGATGAAAAACGCTACTACTTCACCGATGAATACATTGCGGCGACC
GGCAGCGTGATTATTGATGGCGAAGAATACTACTTCGATCCGGATACCGCGCAGCTGGTGATTAGCGAACATCAT
CATCATCACCAT

FIG. 10

SEQ ID NO :15 amino acid sequence of F5 ToxB

MATGWQTIDGKKYYFNTNTAIASTGYTIINGKHFYFNTDGIMQIGVFKGPNGFEYFAPANTDANNIEGQAILYQN
EFLTLNGKKYYFGSDSKAVTGWRIINNKKYYFNPNNAIAAIHLCTINNDKYYFSYDGILQNGYITIERNNFYFDA
NNESKMVTGVFKGPNGFEYFAPANTHNNNIEGQAIVYQNKFLTLNGKKYYFDNDSKAVTGWQTIDGKKYYFNLNT
AEAATGWQTIDGKKYYFNLNTAEAATGWQTIDGKKYYFNTNTFIASTGYTSINGKHFYFNTDGIMQIGVFKGPNG
FEYFAPANTDANNIEGQAILYQNKFLTLNGKKYYFGSDSKAVTGLRTIDGKKYYFNTNTAVAVTGWQTINGKKYY
FNTNTSIASTGYTIISGKHFYFNTDGIMQIGVFKGPDGFEYFAPANTDANNIEGQAIRYQNRFLYLHDNIYYFGN
NSKAATGWVTIDGNRYYFEPNTAMGANGYKTIDNKNFYFRNGLPQIGVFKGSNGFEYFAPANTDANNIEGQAIRY
QNRFLHLLGKIYYFGNNSKAVTGWQTINGKVYYFMPDTAMAAAGGLFEIDGVIYFFGVDGVKAVSGLIYINDSLY
YFKPPVNNLITGFVTVGDDKYYFNPINGGAASIGETIIDDKNYYFNQSGVLQTGVFSTEDGFKYFAPANTLDENL
EGEAIDFTGKLIIDENIYYFDDNYRGAVEWKELDGEMHYFSPETGKAFKGLNQIGDYKYYFNSDGVMQKGFVSIN
DNKHYFDDSGVMKVGYTEIDGKHFYFAENGEMQIGVFNTEDGFKYFAHHNEDLGNEEGEEISYSGILNFNNKIYY
FDDSFTAVVGWKDLEDGSKYYFDEDTAEAYIGLSLINDGQYYFNDDGIMQVGFVTINDKVFYFSDSGIIESGVQN
IDDNYFYIDDNGIVQIGVFDTSDGYKYFAPANTVNDNIYGQAVEYSGLVRVGEDVYYFGETYTIETGWIYDMENE
SDKYYFNPETKKACKGINLIDDIKYYFDEKGIMRTGLISFENNNYYFNENGEMQFGYINIEDKMFYFGEDGVMQI
GVFNTPDGFKYFAHQNTLDENFEGESINYTGWLDLDEKRYYFTDEYIAATGSVIIDGEEYYFDPDTAQLVISEHH
HHHH

FIG. 1 P

SEQ ID NO :16 - nucleotide sequence of F52 new

```
ATGGCAACCGGTTGGCAGACCATCGATGGCAAAAAATATTATTTTAATACCAACACCGCAATTGCAAGCACCGGC
TATACCATTATCAACGGCAAACACTTTTATTTTAACACCGACGGCATTATGCAGATTGGTGTGTTTAAAGGTCCG
AACGGCTTTGAATACTTTGCACCGGCAAATACCGATGCCAATAATATTGAAGGCCAGGCCATTCTGTATCAGAAT
GAATTTCTGACCCTGAACGGCAAAAAATACTACTTTGGCAGCGATAGCAAAGCAGTTACCGGTTGGCGCATCATC
AACAATAAGAAATATTACTTCAACCCGAATAATGCAATTGCAGCAATTCATCTGTGCACCATTAACAACGACAAA
TATTATTTCAGCTATGACGGTATTCTGCAGAATGGCTACATTACCATCGAACGCAACAACTTTTATTTCGATGCC
AACAACGAAAGCAAAATGGTGACCGGTGTTTTCAAAGGCCCTAATGGTTTTGAGTATTTCGCTCCGGCAAACACC
CATAATAACAACATTGAAGGTCAGGCGATCGTTTATCAGAACAAATTCCTGACGCTGAATGGTAAGAAATACTAT
TTCGATAATGACAGCAAAGCCGTGACCGGCTGGCAGACAATTGACGGGAAGAAATATTACTTTAATCTGAATACC
GCAGAAGCAGCAACCGGTTGGCAAACGATCGACGGTAAAAAGTACTACTTCAACCTGAACACAGCCGAAGCAGCC
ACAGGATGGCAGACTATTGATGGAAAAAAATACTATTTCAACACCAACACCTTTATTGCATCTACCGGTTATACC
AGCATTAACGGTAAACATTTCTACTTCAACACCGATGGTATCATGCAGATCGGCGTTTTCAAAGGTCCAAATGGT
TTCGAATACTTTGCCCCTGCCAATACAGATGCAAATAACATCGAGGGTCAGGCAATCCTGTACCAAAACAAATTT
CTGACCCTGAATGGGAAAAAATATTACTTTGGTAGCGATTCTAAAGCCGTTACCGGTCTGCGTACCATTGATGGT
AAAAAATACTACTTTAATACGAATACAGCCGTTGCGGTTACAGGCTGGCAGACCATTAACGGGAAAAAATACTAT
TTTAACACAAATACCAGCATTGCCTCAACGGGTATACCATTATTTCGGGTAAACACTTCTACTTTAATACCGAT
GGTATTATGCAAATCGGAGTCTTTAAAGGACCTGATGGGTTCGAATATTTTGCGCCTGCGAACACTGATGCGAAC
AATATCGAAGGACAGGCAATCCGCTATCAGAATCGCTTTCTGTATCTGCACGACAACATCTATTATTTTGGCAAC
AATTCAAAAGCAGCCACCGGCTGGGTTACAATTGATGGCAACCGCTACTATTTCGAACCGAATACCGCAATGGGT
GCAAATGGCTACAAAACCATCGATAATAAAAATTTCTATTTTCGCAACGGTCTGCCGCAGATCGGGGTATTTAAA
GGTAGCAACGGCTTCGAATACTTCGCTCCAGCGAATACGACGCGAACAATATTGAGGGTCAAGCGATTCGTTAT
CAAAACCGTTTTCTGCATCTGCTGGGCAAAATCTACTACTTTGGCAATAACAGTAAAGCAGTTACTGGATGGCAG
ACAATCAATGGTAAAGTGTACTATTTTATGCCGGATACCGCCATGGCAGCAGCCGGTGGTCTGTTTGAAATTGAT
GGCGTGATCTATTTTTTGGTGTGGATGGTGTTAAAGCAGTGAAAGGCCTGAACCAGATCGGCGATTACAAATAC
TACTTCAACAGCGATGGCGTGATGCAGAAGGCTTTGTGAGCATCAACGATAACAAACACTATTTCGATGATAGC
GGTGTGATGAAAGTGGGCTATACCGAAATTGATGGCAAACATTTCTACTTCGCGGAAAACGGCGAAATGCAGATT
GGCGTGTTCAATACCGAAGATGGTTTCAAATACTTCGCGCACCATAACGAAGATCTGGGTAACGAAGAAGGCGAA
GAAATTAGCTATAGCGGCATCCTGAACTTCAACAACAAAATCTACTACTTTGATGATAGCTTTACCGCGGTGGTG
GGCTGGAAAGATCTGGAAGATGGCAGCAAATATTATTTCGATGAAGATACCGCGGAAGCGTATATTGGCCTGAGC
CTGATTAACGATGGCCAGTACTATTTTAACGATGATGGCATTATGCAGGTGGGTTTCGTGACCATTAATGATAAA
GTGTTCTATTTCAGCGATAGCGGCATTATTGAAAGCGGCGTGCAGAACATTGATGATAACTACTTCTACATCGAT
GATAACGGCATTGTGCAGATCGGCGTTTTTGATACCAGCGATGGCTACAAATATTTCGCACCGGCCAATACCGTG
AACGATAACATTTATGGCCAGGCGGTGGAATATAGCGGTCTGGTGCGTGTGGGCGAAGATGTGTATTATTTCGGC
GAAACCTATACCATCGAAACCGGCTGGATTTATGATATGGAAAACGAAAGCGATAAATATTACTTTAATCCGGAA
ACGAAAAAAGCGTGCAAAGGCATTAACCTGATCGATGATATCAAATACTATTTTGATGAAAAAGGCATTATGCGT
ACCGGTCTGATTAGCTTCGAAAACAACAACTATTACTTCAACGAAAACGGTGAAATGCAGTTCGGCTACATCAAC
ATCGAAGATAAAATGTTCTACTTCGGCGAAGATGGTGTTATGCAGATTGGTGTTTTAACACCCCGGATGGCTTC
AAATACTTTGCCCATCAGAATACCCTGGATGAAAATTTCGAAGGTGAAAGCATTAACTATACCGGCTGGCTGGAT
CTGGATGAAAAACGCTACTACTTCACCGATGAATACATTGCGGCGACCGGCAGCGTGATTAGCGAACATCATCATCATCACCAT
```

FIG. 1 Q

SEQ ID NO :17 – amino acid sequence of F52 New

MATGWQTIDGKKYYFNTNTAIASTGYTIINGKHFYFNTDGIMQIGVFKGPNGFEYFAPANTDANNIEGQAILYQN
EFLTLNGKKYYFGSDSKAVTGWRIINNKKYYFNPNNAIAAIHLCTINNDKYYFSYDGILQNGYITIERNNFYFDA
NNESKMVTGVFKGPNGFEYFAPANTHNNNIEGQAIVYQNKFLTLNGKKYYFDNDSKAVTGWQTIDGKKYYFNLNT
AEAATGWQTIDGKKYYFNLNTAEAATGWQTIDGKKYYFNTNTFIASTGYTSINGKHFYFNTDGIMQIGVFKGPNG
FEYFAPANTDANNIEGQAILYQNKFLTLNGKKYYFGSDSKAVTGLRTIDGKKYYFNTNTAVAVTGWQTINGKKYY
FNTNTSIASTGYTIISGKHFYFNTDGIMQIGVFKGPDGFEYFAPANTDANNIEGQAIRYQNRFLYLHDNIYYFGN
NSKAATGWVTIDGNRYYFEPNTAMGANGYKTIDNKNFYFRNGLPQIGVFKGSNGFEYFAPANTDANNIEGQAIRY
QNRFLHLLGKIYYFGNNSKAVTGWQTINGKVYYFMPDTAMAAAGGLFEIDGVIYFFGVDGVKAVKGLNQIGDYKY
YFNSDGVMQKGFVSINDNKHYFDDSGVMKVGYTEIDGKHFYFAENGEMQIGVFNTEDGFKYFAHHNEDLGNEEGE
EISYSGILNFNNKIYYFDDSFTAVVGWKDLEDGSKYYFDEDTAEAYIGLSLINDGQYYFNDDGIMQVGFVTINDK
VFYFSDSGIIESGVQNIDDNYFYIDDNGIVQIGVFDTSDGYKYFAPANTVNDNIYGQAVEYSGLVRVGEDVYYFG
ETYTIETGWIYDMENESDKYYFNPETKKACKGINLIDDIKYYFDEKGIMRTGLISFENNNYYFNENGEMQFGYIN
IEDKMFYFGEDGVMQIGVFNTPDGFKYFAHQNTLDENFEGESINYTGWLDLDEKRYYFTDEYIAATGSVIIDGEE
YYFDPDTAQLVISEHHHHHH

FIG. 6

C-terminal domain of ToxA

I  II  III  IV  V  VI  VII VIII

F4

C-terminal domain of ToxB

I  II  III  IV  V

FIG. 7

C-terminal domain of ToxA

I  II  III  IV  V  VI  VII VIII

+Gly : F5

C-terminal domain of ToxB

I  II  III  IV  V

FIG. 10

Near-UV CD of ToxA-ToxB fusions

- f2v2n
- f3n
- f4n
- f5n x-axis: Wavelength (nm)
y-axis: CD

FIG. 11

20100673 : Mice immunization with C. difficile ToxA-Cter, ToxB-Cter and fusion proteins 2d generation formulated in AS03B
ELISA a-ToxA : concentrations (µg/ml) on Post III sera

| Group | Value |
|---|---|
| 10µg Ag/ml ToxA (aa 2387-2706) | 1215 |
| 10µg Ag/ml ToxB (aa 1750-2360) | 4.1 |
| 10µg Ag/dose F1 | 1073 |
| 10µg Ag/dose F2 | 937 |
| 10µg Ag/dose F3 | 839 |
| 10µg Ag/dose F4 | 771 |
| 10µg Ag/dose F5 | 1475 |
| 3µg Ag/dose ToxA (aa 2387-2706) | 1160 |
| 3µg Ag/dose ToxB (aa 1750-2360) | 4.3 |
| 3µg Ag/dose F1 | 929 |
| 3µg Ag/dose F2 | 1061 |
| 3µg Ag/dose F3 | 871 |
| 3µg Ag/dose F4 | 629 |
| 3µg Ag/dose F5 | 1277 |
| AS03B adjuvant only | 2.5 |

FIG. 17

Near UV CD of new constructs

- F54 new
- F54 gly
- F5 ToxB
- F52 new

FIG. 18

Mice immunization with C. difficile fusion proteins formulated in AS03B Anti-ToxA ELISA: ELISA titers (μg/ml) on individual Post III sera

| | F2 | F52new | F54Gly | F54new | F5 ToxB |
|---|---|---|---|---|---|
| Geomean | 764 | 937 | 841 | 704 | 761 |

FIG. 19

Mice immunization with C. difficile fusion proteins formulated in AS03B Anti-ToxB ELISA: ELISA titers (µg/ml) on Post III individual sera

| | F2 2nd generation | F52new 3d generation | F54Gly 3d generation | F54new 3d generation | F5 ToxB 3d generation |
|---|---|---|---|---|---|
| Geomean | 765 | 688 | 581 | 611 | 653 |

FIG. 20

Mice immunization with C. difficile fusion proteins formulated in AS03B Hemagglutination inhibition assay: inhibition titers on Post III pooled sera

| | F2 2nd generation | F52new 3d generation | F54Gly 3d generation | F54new 3d generation | F5 ToxB 3d generation |
|---|---|---|---|---|---|
| Pools | 1280 | 1280 | 2560 | 1280 | 1280 |

```
                        SEQUENCE LISTING

<160> NUMBER OF SEQ ID NOS: 17

<210> SEQ ID NO 1
<211> LENGTH: 2710
<212> TYPE: PRT
<213> ORGANISM: Clostridium Difficile

<400> SEQUENCE: 1

Met Ser Leu Ile Ser Lys Glu Glu Leu Ile Lys Leu Ala Tyr Ser Ile
 1               5                  10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Glu Asn Lys Tyr Leu Gln Leu
        35                  40                  45

Lys Lys Leu Asn Glu Ser Ile Asp Val Phe Met Asn Lys Tyr Lys Thr
 50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335
```

```
Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
            355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Pro Lys Asn Ser Ile
            595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Gly Phe Ala Arg Leu Ser Val Asp Ser
            660                 665                 670

Leu Ser Asn Glu Ile Ser Ser Phe Leu Asp Thr Ile Lys Leu Asp Ile
            675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750
```

-continued

```
Arg Lys Glu Leu Leu Ala His Ser Gly Lys Trp Ile Asn Lys Glu Glu
            755                 760                 765
Ala Ile Met Ser Asp Leu Ser Ser Lys Glu Tyr Ile Phe Phe Asp Ser
        770                 775                 780
Ile Asp Asn Lys Leu Lys Ala Lys Ser Lys Asn Ile Pro Gly Leu Ala
785                 790                 795                 800
Ser Ile Ser Glu Asp Ile Lys Thr Leu Leu Leu Asp Ala Ser Val Ser
                805                 810                 815
Pro Asp Thr Lys Phe Ile Leu Asn Asn Leu Lys Leu Asn Ile Glu Ser
            820                 825                 830
Ser Ile Gly Asp Tyr Ile Tyr Tyr Glu Lys Leu Glu Pro Val Lys Asn
        835                 840                 845
Ile Ile His Asn Ser Ile Asp Asp Leu Ile Asp Glu Phe Asn Leu Leu
    850                 855                 860
Glu Asn Val Ser Asp Glu Leu Tyr Glu Leu Lys Lys Leu Asn Asn Leu
865                 870                 875                 880
Asp Glu Lys Tyr Leu Ile Ser Phe Glu Asp Ile Ser Asn Asn Ser
                885                 890                 895
Thr Tyr Ser Val Arg Phe Ile Asn Lys Ser Asn Gly Glu Ser Val Tyr
            900                 905                 910
Val Glu Thr Glu Lys Glu Ile Phe Ser Lys Tyr Ser Glu His Ile Thr
        915                 920                 925
Lys Glu Ile Ser Thr Ile Lys Asn Ser Ile Ile Thr Asp Val Asn Gly
    930                 935                 940
Asn Leu Leu Asp Asn Ile Gln Leu Asp His Thr Ser Gln Val Asn Thr
945                 950                 955                 960
Leu Asn Ala Ala Phe Phe Ile Gln Ser Leu Ile Asp Tyr Ser Ser Asn
                965                 970                 975
Lys Asp Val Leu Asn Asp Leu Ser Thr Ser Val Lys Val Gln Leu Tyr
            980                 985                 990
Ala Gln Leu Phe Ser Thr Gly Leu Asn Thr Ile Tyr Asp Ser Ile Gln
        995                1000                1005
Leu Val Asn Leu Ile Ser Asn Ala Val Asn Asp Thr Ile Asn Val Leu
    1010                1015                1020
Pro Thr Ile Thr Glu Gly Ile Pro Ile Val Ser Thr Ile Leu Asp Gly
1025                1030                1035                1040
Ile Asn Leu Gly Ala Ala Ile Lys Glu Leu Leu Asp Glu His Asp Pro
                1045                1050                1055
Leu Leu Lys Lys Glu Leu Glu Ala Lys Val Gly Val Leu Ala Ile Asn
            1060                1065                1070
Met Ser Leu Ser Ile Ala Ala Thr Val Ala Ser Ile Val Gly Ile Gly
        1075                1080                1085
Ala Glu Val Thr Ile Phe Leu Leu Pro Ile Ala Gly Ile Ser Ala Gly
    1090                1095                1100
Ile Pro Ser Leu Val Asn Asn Glu Leu Ile Leu His Asp Lys Ala Thr
1105                1110                1115                1120
Ser Val Val Asn Tyr Phe Asn His Leu Ser Glu Ser Lys Lys Tyr Gly
                1125                1130                1135
Pro Leu Lys Thr Glu Asp Asp Lys Ile Leu Val Pro Ile Asp Asp Leu
            1140                1145                1150
Val Ile Ser Glu Ile Asp Phe Asn Asn Asn Ser Ile Lys Leu Gly Thr
        1155                1160                1165
Cys Asn Ile Leu Ala Met Glu Gly Gly Ser Gly His Thr Val Thr Gly
```

-continued

```
                1170                1175                1180

Asn Ile Asp His Phe Phe Ser Ser Pro Ser Ile Ser Ser His Ile Pro
1185                1190                1195                1200

Ser Leu Ser Ile Tyr Ser Ala Ile Gly Ile Glu Thr Glu Asn Leu Asp
                1205                1210                1215

Phe Ser Lys Lys Ile Met Met Leu Pro Asn Ala Pro Ser Arg Val Phe
                1220                1225                1230

Trp Trp Glu Thr Gly Ala Val Pro Gly Leu Arg Ser Leu Glu Asn Asp
                1235                1240                1245

Gly Thr Arg Leu Leu Asp Ser Ile Arg Asp Leu Tyr Pro Gly Lys Phe
                1250                1255                1260

Tyr Trp Arg Phe Tyr Ala Phe Phe Asp Tyr Ala Ile Thr Thr Leu Lys
1265                1270                1275                1280

Pro Val Tyr Glu Asp Thr Asn Ile Lys Ile Lys Leu Asp Lys Asp Thr
                1285                1290                1295

Arg Asn Phe Ile Met Pro Thr Ile Thr Thr Asn Glu Ile Arg Asn Lys
                1300                1305                1310

Leu Ser Tyr Ser Phe Asp Gly Ala Gly Gly Thr Tyr Ser Leu Leu Leu
                1315                1320                1325

Ser Ser Tyr Pro Ile Ser Thr Asn Ile Asn Leu Ser Lys Asp Asp Leu
                1330                1335                1340

Trp Ile Phe Asn Ile Asp Asn Glu Val Arg Glu Ile Ser Ile Glu Asn
1345                1350                1355                1360

Gly Thr Ile Lys Lys Gly Lys Leu Ile Lys Asp Val Leu Ser Lys Ile
                1365                1370                1375

Asp Ile Asn Lys Asn Lys Leu Ile Ile Gly Asn Gln Thr Ile Asp Phe
                1380                1385                1390

Ser Gly Asp Ile Asp Asn Lys Asp Arg Tyr Ile Phe Leu Thr Cys Glu
                1395                1400                1405

Leu Asp Asp Lys Ile Ser Leu Ile Ile Glu Ile Asn Leu Val Ala Lys
                1410                1415                1420

Ser Tyr Ser Leu Leu Leu Ser Gly Asp Lys Asn Tyr Leu Ile Ser Asn
1425                1430                1435                1440

Leu Ser Asn Thr Ile Glu Lys Ile Asn Thr Leu Gly Leu Asp Ser Lys
                1445                1450                1455

Asn Ile Ala Tyr Asn Tyr Thr Asp Glu Ser Asn Asn Lys Tyr Phe Gly
                1460                1465                1470

Ala Ile Ser Lys Thr Ser Gln Lys Ser Ile Ile His Tyr Lys Lys Asp
                1475                1480                1485

Ser Lys Asn Ile Leu Glu Phe Tyr Asn Asp Ser Thr Leu Glu Phe Asn
                1490                1495                1500

Ser Lys Asp Phe Ile Ala Glu Asp Ile Asn Val Phe Met Lys Asp Asp
1505                1510                1515                1520

Ile Asn Thr Ile Thr Gly Lys Tyr Tyr Val Asp Asn Asn Thr Asp Lys
                1525                1530                1535

Ser Ile Asp Phe Ser Ile Ser Leu Val Ser Lys Asn Gln Val Lys Val
                1540                1545                1550

Asn Gly Leu Tyr Leu Asn Glu Ser Val Tyr Ser Ser Tyr Leu Asp Phe
                1555                1560                1565

Val Lys Asn Ser Asp Gly His His Asn Thr Ser Asn Phe Met Asn Leu
                1570                1575                1580

Phe Leu Asp Asn Ile Ser Phe Trp Lys Leu Phe Gly Phe Glu Asn Ile
1585                1590                1595                1600
```

-continued

Asn Phe Val Ile Asp Lys Tyr Phe Thr Leu Val Gly Lys Thr Asn Leu
            1605                1610                1615

Gly Tyr Val Glu Phe Ile Cys Asp Asn Asn Lys Asn Ile Asp Ile Tyr
            1620                1625                1630

Phe Gly Glu Trp Lys Thr Ser Ser Lys Ser Thr Ile Phe Ser Gly
            1635                1640            1645

Asn Gly Arg Asn Val Val Glu Pro Ile Tyr Asn Pro Asp Thr Gly
1650                1655                1660

Glu Asp Ile Ser Thr Ser Leu Asp Phe Ser Tyr Glu Pro Leu Tyr Gly
1665                1670                1675                1680

Ile Asp Arg Tyr Ile Asn Lys Val Leu Ile Ala Pro Asp Leu Tyr Thr
            1685                1690                1695

Ser Leu Ile Asn Ile Asn Thr Asn Tyr Tyr Ser Asn Glu Tyr Tyr Pro
            1700                1705                1710

Glu Ile Ile Val Leu Asn Pro Asn Thr Phe His Lys Lys Val Asn Ile
            1715                1720                1725

Asn Leu Asp Ser Ser Ser Phe Glu Tyr Lys Trp Ser Thr Glu Gly Ser
            1730                1735                1740

Asp Phe Ile Leu Val Arg Tyr Leu Glu Glu Ser Asn Lys Lys Ile Leu
1745                1750                1755                1760

Gln Lys Ile Arg Ile Lys Gly Ile Leu Ser Asn Thr Gln Ser Phe Asn
            1765                1770                1775

Lys Met Ser Ile Asp Phe Lys Asp Ile Lys Lys Leu Ser Leu Gly Tyr
            1780                1785                1790

Ile Met Ser Asn Phe Lys Ser Phe Asn Ser Glu Asn Glu Leu Asp Arg
            1795                1800                1805

Asp His Leu Gly Phe Lys Ile Ile Asp Asn Lys Thr Tyr Tyr Tyr Asp
            1810                1815                1820

Glu Asp Ser Lys Leu Val Lys Gly Leu Ile Asn Ile Asn Asn Ser Leu
1825                1830                1835                1840

Phe Tyr Phe Asp Pro Ile Glu Phe Asn Leu Val Thr Gly Trp Gln Thr
            1845                1850                1855

Ile Asn Gly Lys Lys Tyr Tyr Phe Asp Ile Asn Thr Gly Ala Ala Leu
            1860                1865                1870

Thr Ser Tyr Lys Ile Ile Asn Gly Lys His Phe Tyr Phe Asn Asn Asp
            1875                1880                1885

Gly Val Met Gln Leu Gly Val Phe Lys Gly Pro Asp Gly Phe Glu Tyr
            1890                1895                1900

Phe Ala Pro Ala Asn Thr Gln Asn Asn Asn Ile Glu Gly Gln Ala Ile
1905                1910                1915                1920

Val Tyr Gln Ser Lys Phe Leu Thr Leu Asn Gly Lys Lys Tyr Tyr Phe
            1925                1930                1935

Asp Asn Asn Ser Lys Ala Val Thr Gly Trp Arg Ile Ile Asn Asn Glu
            1940                1945                1950

Lys Tyr Tyr Phe Asn Pro Asn Asn Ala Ile Ala Ala Val Gly Leu Gln
            1955                1960                1965

Val Ile Asp Asn Asn Lys Tyr Tyr Phe Asn Pro Asp Thr Ala Ile Ile
            1970                1975                1980

Ser Lys Gly Trp Gln Thr Val Asn Gly Ser Arg Tyr Tyr Phe Asp Thr
1985                1990                1995                2000

Asp Thr Ala Ile Ala Phe Asn Gly Tyr Lys Thr Ile Asp Gly Lys His
            2005                2010                2015

-continued

Phe Tyr Phe Asp Ser Asp Cys Val Val Lys Ile Gly Val Phe Ser Thr
            2020                2025                2030

Ser Asn Gly Phe Glu Tyr Phe Ala Pro Ala Asn Thr Tyr Asn Asn
    2035                2040                2045

Ile Glu Gly Gln Ala Ile Val Tyr Gln Ser Lys Phe Leu Thr Leu Asn
            2050                2055                2060

Gly Lys Lys Tyr Tyr Phe Asp Asn Asn Ser Lys Ala Val Thr Gly Leu
2065                2070                2075                2080

Gln Thr Ile Asp Ser Lys Lys Tyr Tyr Phe Asn Thr Asn Thr Ala Glu
            2085                2090                2095

Ala Ala Thr Gly Trp Gln Thr Ile Asp Gly Lys Lys Tyr Tyr Phe Asn
            2100                2105                2110

Thr Asn Thr Ala Glu Ala Ala Thr Gly Trp Gln Thr Ile Asp Gly Lys
            2115                2120                2125

Lys Tyr Tyr Phe Asn Thr Asn Thr Ala Ile Ala Ser Thr Gly Tyr Thr
    2130                2135                2140

Ile Ile Asn Gly Lys His Phe Tyr Phe Asn Thr Asp Gly Ile Met Gln
2145                2150                2155                2160

Ile Gly Val Phe Lys Gly Pro Asn Gly Phe Glu Tyr Phe Ala Pro Ala
            2165                2170                2175

Asn Thr Asp Ala Asn Asn Ile Glu Gly Gln Ala Ile Leu Tyr Gln Asn
            2180                2185                2190

Glu Phe Leu Thr Leu Asn Gly Lys Lys Tyr Tyr Phe Gly Ser Asp Ser
            2195                2200                2205

Lys Ala Val Thr Gly Trp Arg Ile Ile Asn Asn Lys Lys Tyr Tyr Phe
    2210                2215                2220

Asn Pro Asn Asn Ala Ile Ala Ala Ile His Leu Cys Thr Ile Asn Asn
2225                2230                2235                2240

Asp Lys Tyr Tyr Phe Ser Tyr Asp Gly Ile Leu Gln Asn Gly Tyr Ile
            2245                2250                2255

Thr Ile Glu Arg Asn Asn Phe Tyr Phe Asp Ala Asn Asn Glu Ser Lys
            2260                2265                2270

Met Val Thr Gly Val Phe Lys Gly Pro Asn Gly Phe Glu Tyr Phe Ala
    2275                2280                2285

Pro Ala Asn Thr His Asn Asn Asn Ile Glu Gly Gln Ala Ile Val Tyr
            2290                2295                2300

Gln Asn Lys Phe Leu Thr Leu Asn Gly Lys Lys Tyr Tyr Phe Asp Asn
2305                2310                2315                2320

Asp Ser Lys Ala Val Thr Gly Trp Gln Thr Ile Asp Gly Lys Lys Tyr
            2325                2330                2335

Tyr Phe Asn Leu Asn Thr Ala Glu Ala Ala Thr Gly Trp Gln Thr Ile
            2340                2345                2350

Asp Gly Lys Lys Tyr Tyr Phe Asn Leu Asn Thr Ala Glu Ala Ala Thr
    2355                2360                2365

Gly Trp Gln Thr Ile Asp Gly Lys Lys Tyr Tyr Phe Asn Thr Asn Thr
    2370                2375                2380

Phe Ile Ala Ser Thr Gly Tyr Thr Ser Ile Asn Gly Lys His Phe Tyr
2385                2390                2395                2400

Phe Asn Thr Asp Gly Ile Met Gln Ile Gly Val Phe Lys Gly Pro Asn
            2405                2410                2415

Gly Phe Glu Tyr Phe Ala Pro Ala Asn Thr Asp Ala Asn Asn Ile Glu
            2420                2425                2430

Gly Gln Ala Ile Leu Tyr Gln Asn Lys Phe Leu Thr Leu Asn Gly Lys

```
                    2435                2440                2445
Lys Tyr Tyr Phe Gly Ser Asp Ser Lys Ala Val Thr Gly Leu Arg Thr
                2450                2455                2460
Ile Asp Gly Lys Lys Tyr Tyr Phe Asn Thr Asn Thr Ala Val Ala Val
2465                2470                2475                2480
Thr Gly Trp Gln Thr Ile Asn Gly Lys Lys Tyr Tyr Phe Asn Thr Asn
                    2485                2490                2495
Thr Ser Ile Ala Ser Thr Gly Tyr Thr Ile Ile Ser Gly Lys His Phe
                2500                2505                2510
Tyr Phe Asn Thr Asp Gly Ile Met Gln Ile Gly Val Phe Lys Gly Pro
                2515                2520                2525
Asp Gly Phe Glu Tyr Phe Ala Pro Ala Asn Thr Asp Ala Asn Asn Ile
                2530                2535                2540
Glu Gly Gln Ala Ile Arg Tyr Gln Asn Arg Phe Leu Tyr Leu His Asp
2545                2550                2555                2560
Asn Ile Tyr Tyr Phe Gly Asn Asn Ser Lys Ala Ala Thr Gly Trp Val
                2565                2570                2575
Thr Ile Asp Gly Asn Arg Tyr Tyr Phe Glu Pro Asn Thr Ala Met Gly
                2580                2585                2590
Ala Asn Gly Tyr Lys Thr Ile Asp Asn Lys Asn Phe Tyr Phe Arg Asn
                2595                2600                2605
Gly Leu Pro Gln Ile Gly Val Phe Lys Gly Ser Asn Gly Phe Glu Tyr
                2610                2615                2620
Phe Ala Pro Ala Asn Thr Asp Ala Asn Asn Ile Glu Gly Gln Ala Ile
2625                2630                2635                2640
Arg Tyr Gln Asn Arg Phe Leu His Leu Leu Gly Lys Ile Tyr Tyr Phe
                    2645                2650                2655
Gly Asn Asn Ser Lys Ala Val Thr Gly Trp Gln Thr Ile Asn Gly Lys
                2660                2665                2670
Val Tyr Tyr Phe Met Pro Asp Thr Ala Met Ala Ala Ala Gly Gly Leu
                2675                2680                2685
Phe Glu Ile Asp Gly Val Ile Tyr Phe Phe Gly Val Asp Gly Val Lys
                2690                2695                2700
Ala Pro Gly Ile Tyr Gly
2705                2710

<210> SEQ ID NO 2
<211> LENGTH: 2366
<212> TYPE: PRT
<213> ORGANISM: Clostridium Difficile

<400> SEQUENCE: 2

Met Ser Leu Val Asn Arg Lys Gln Leu Glu Lys Met Ala Asn Val Arg
1               5                   10                  15
Phe Arg Thr Gln Glu Asp Glu Tyr Val Ala Ile Leu Asp Ala Leu Glu
                20                  25                  30
Glu Tyr His Asn Met Ser Glu Asn Thr Val Val Glu Lys Tyr Leu Lys
                35                  40                  45
Leu Lys Asp Ile Asn Ser Leu Thr Asp Ile Tyr Ile Asp Thr Tyr Lys
            50                  55                  60
Lys Ser Gly Arg Asn Lys Ala Leu Lys Lys Phe Lys Glu Tyr Leu Val
65                  70                  75                  80
Thr Glu Val Leu Glu Leu Lys Asn Asn Asn Leu Thr Pro Val Glu Lys
                85                  90                  95
```

```
Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
```

-continued

```
            515                 520                 525
Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Asn Pro Gly
    610                 615                 620

Asp Gly Glu Ile Gln Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940
```

-continued

```
Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
                995                1000                1005

Glu Leu Val Ser Thr Ala Leu Asp Glu Thr Ile Asp Leu Leu Pro Thr
       1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Ser Asp Pro Leu Leu
                1045                1050                1055

Arg Gln Glu Ile Glu Ala Lys Ile Gly Ile Met Ala Val Asn Leu Thr
            1060                1065                1070

Thr Ala Thr Thr Ala Ile Ile Thr Ser Ser Leu Gly Ile Ala Ser Gly
                1075                1080                1085

Phe Ser Ile Leu Leu Val Pro Leu Ala Gly Ile Ser Ala Gly Ile Pro
    1090                1095                1100

Ser Leu Val Asn Asn Glu Leu Val Leu Arg Asp Lys Ala Thr Lys Val
1105                1110                1115                1120

Val Asp Tyr Phe Lys His Val Ser Leu Val Glu Thr Glu Gly Val Phe
                1125                1130                1135

Thr Leu Leu Asp Asp Lys Ile Met Met Pro Gln Asp Asp Leu Val Ile
                1140                1145                1150

Ser Glu Ile Asp Phe Asn Asn Asn Ser Ile Val Leu Gly Lys Cys Glu
            1155                1160                1165

Ile Trp Arg Met Glu Gly Gly Ser Gly His Thr Val Thr Asp Asp Ile
1170                1175                1180

Asp His Phe Phe Ser Ala Pro Ser Ile Thr Tyr Arg Glu Pro His Leu
1185                1190                1195                1200

Ser Ile Tyr Asp Val Leu Glu Val Gln Lys Glu Glu Leu Asp Leu Ser
            1205                1210                1215

Lys Asp Leu Met Val Leu Pro Asn Ala Pro Asn Arg Val Phe Ala Trp
       1220                1225                1230

Glu Thr Gly Trp Thr Pro Gly Leu Arg Ser Leu Glu Asn Asp Gly Thr
            1235                1240                1245

Lys Leu Leu Asp Arg Ile Arg Asp Asn Tyr Glu Gly Glu Phe Tyr Trp
       1250                1255                1260

Arg Tyr Phe Ala Phe Ile Ala Asp Ala Leu Ile Thr Thr Leu Lys Pro
1265                1270                1275                1280

Arg Tyr Glu Asp Thr Asn Ile Arg Ile Asn Leu Asp Ser Asn Thr Arg
            1285                1290                1295

Ser Phe Ile Val Pro Ile Ile Thr Thr Glu Tyr Ile Arg Glu Lys Leu
       1300                1305                1310

Ser Tyr Ser Phe Tyr Gly Ser Gly Gly Thr Tyr Ala Leu Ser Leu Ser
       1315                1320                1325

Gln Tyr Asn Met Gly Ile Asn Ile Glu Leu Ser Glu Ser Asp Val Trp
       1330                1335                1340

Ile Ile Asp Val Asp Asn Val Val Arg Asp Val Thr Ile Glu Ser Asp
1345                1350                1355                1360
```

```
Lys Ile Lys Lys Gly Asp Leu Ile Glu Gly Ile Leu Ser Thr Leu Ser
            1365                1370                1375
Ile Glu Glu Asn Lys Ile Ile Leu Asn Ser His Glu Ile Asn Phe Ser
        1380                1385                1390
Gly Glu Val Asn Gly Ser Asn Gly Phe Val Ser Leu Thr Phe Ser Ile
    1395                1400                1405
Leu Glu Gly Ile Asn Ala Ile Ile Glu Val Asp Leu Leu Ser Lys Ser
1410                1415                1420
Tyr Lys Leu Leu Ile Ser Gly Glu Leu Lys Ile Leu Met Leu Asn Ser
1425                1430                1435                1440
Asn His Ile Gln Gln Lys Ile Asp Tyr Ile Gly Phe Asn Ser Glu Leu
            1445                1450                1455
Gln Lys Asn Ile Pro Tyr Ser Phe Val Asp Ser Glu Gly Lys Glu Asn
        1460                1465                1470
Gly Phe Ile Asn Gly Ser Thr Lys Glu Gly Leu Phe Val Ser Glu Leu
    1475                1480                1485
Pro Asp Val Val Leu Ile Ser Lys Val Tyr Met Asp Asp Ser Lys Pro
    1490                1495                1500
Ser Phe Gly Tyr Tyr Ser Asn Asn Leu Lys Asp Val Lys Val Ile Thr
1505                1510                1515                1520
Lys Asp Asn Val Asn Ile Leu Thr Gly Tyr Tyr Leu Lys Asp Ile
        1525                1530                1535
Lys Ile Ser Leu Ser Leu Thr Leu Gln Asp Glu Lys Thr Ile Lys Leu
        1540                1545                1550
Asn Ser Val His Leu Asp Glu Ser Gly Val Ala Glu Ile Leu Lys Phe
    1555                1560                1565
Met Asn Arg Lys Gly Asn Thr Asn Thr Ser Asp Ser Leu Met Ser Phe
    1570                1575                1580
Leu Glu Ser Met Asn Ile Lys Ser Ile Phe Val Asn Phe Leu Gln Ser
1585                1590                1595                1600
Asn Ile Lys Phe Ile Leu Asp Ala Asn Phe Ile Ile Ser Gly Thr Thr
            1605                1610                1615
Ser Ile Gly Gln Phe Glu Phe Ile Cys Asp Glu Asn Asp Asn Ile Gln
        1620                1625                1630
Pro Tyr Phe Ile Lys Phe Asn Thr Leu Glu Thr Asn Tyr Thr Leu Tyr
    1635                1640                1645
Val Gly Asn Arg Gln Asn Met Ile Val Glu Pro Asn Tyr Asp Leu Asp
    1650                1655                1660
Asp Ser Gly Asp Ile Ser Ser Thr Val Ile Asn Phe Ser Gln Lys Tyr
1665                1670                1675                1680
Leu Tyr Gly Ile Asp Ser Cys Val Asn Lys Val Val Ile Ser Pro Asn
            1685                1690                1695
Ile Tyr Thr Asp Glu Ile Asn Ile Thr Pro Val Tyr Glu Thr Asn Asn
        1700                1705                1710
Thr Tyr Pro Glu Val Ile Val Leu Asp Ala Asn Tyr Ile Asn Glu Lys
    1715                1720                1725
Ile Asn Val Asn Ile Asn Asp Leu Ser Ile Arg Tyr Val Trp Ser Asn
    1730                1735                1740
Asp Gly Asn Asp Phe Ile Leu Met Ser Thr Ser Glu Glu Asn Lys Val
1745                1750                1755                1760
Ser Gln Val Lys Ile Arg Phe Val Asn Val Phe Lys Asp Lys Thr Leu
        1765                1770                1775
Ala Asn Lys Leu Ser Phe Asn Phe Ser Asp Lys Gln Asp Val Pro Val
```

1780            1785            1790
Ser Glu Ile Ile Leu Ser Phe Thr Pro Ser Tyr Tyr Glu Asp Gly Leu
    1795            1800            1805

Ile Gly Tyr Asp Leu Gly Leu Val Ser Leu Tyr Asn Glu Lys Phe Tyr
1810            1815            1820

Ile Asn Asn Phe Gly Met Met Val Ser Gly Leu Ile Tyr Ile Asn Asp
1825            1830            1835            1840

Ser Leu Tyr Tyr Phe Lys Pro Pro Val Asn Asn Leu Ile Thr Gly Phe
            1845            1850            1855

Val Thr Val Gly Asp Asp Lys Tyr Tyr Phe Asn Pro Ile Asn Gly Gly
            1860            1865            1870

Ala Ala Ser Ile Gly Glu Thr Ile Ile Asp Asp Lys Asn Tyr Tyr Phe
            1875            1880            1885

Asn Gln Ser Gly Val Leu Gln Thr Gly Val Phe Ser Thr Glu Asp Gly
            1890            1895            1900

Phe Lys Tyr Phe Ala Pro Ala Asn Thr Leu Asp Glu Asn Leu Glu Gly
1905            1910            1915            1920

Glu Ala Ile Asp Phe Thr Gly Lys Leu Ile Ile Asp Glu Asn Ile Tyr
            1925            1930            1935

Tyr Phe Asp Asp Asn Tyr Arg Gly Ala Val Glu Trp Lys Glu Leu Asp
            1940            1945            1950

Gly Glu Met His Tyr Phe Ser Pro Glu Thr Gly Lys Ala Phe Lys Gly
            1955            1960            1965

Leu Asn Gln Ile Gly Asp Tyr Lys Tyr Tyr Phe Asn Ser Asp Gly Val
    1970            1975            1980

Met Gln Lys Gly Phe Val Ser Ile Asn Asp Asn Lys His Tyr Phe Asp
1985            1990            1995            2000

Asp Ser Gly Val Met Lys Val Gly Tyr Thr Glu Ile Asp Gly Lys His
            2005            2010            2015

Phe Tyr Phe Ala Glu Asn Gly Glu Met Gln Ile Gly Val Phe Asn Thr
            2020            2025            2030

Glu Asp Gly Phe Lys Tyr Phe Ala His His Asn Glu Asp Leu Gly Asn
            2035            2040            2045

Glu Glu Gly Glu Glu Ile Ser Tyr Ser Gly Ile Leu Asn Phe Asn Asn
    2050            2055            2060

Lys Ile Tyr Tyr Phe Asp Asp Ser Phe Thr Ala Val Val Gly Trp Lys
2065            2070            2075            2080

Asp Leu Glu Asp Gly Ser Lys Tyr Tyr Phe Asp Glu Asp Thr Ala Glu
            2085            2090            2095

Ala Tyr Ile Gly Leu Ser Leu Ile Asn Asp Gly Gln Tyr Tyr Phe Asn
            2100            2105            2110

Asp Asp Gly Ile Met Gln Val Gly Phe Val Thr Ile Asn Asp Lys Val
            2115            2120            2125

Phe Tyr Phe Ser Asp Ser Gly Ile Ile Glu Ser Gly Val Gln Asn Ile
            2130            2135            2140

Asp Asp Asn Tyr Phe Tyr Ile Asp Asp Asn Gly Ile Val Gln Ile Gly
2145            2150            2155            2160

Val Phe Asp Thr Ser Asp Gly Tyr Lys Tyr Phe Ala Pro Ala Asn Thr
            2165            2170            2175

Val Asn Asp Asn Ile Tyr Gly Gln Ala Val Glu Tyr Ser Gly Leu Val
            2180            2185            2190

Arg Val Gly Glu Asp Val Tyr Tyr Phe Gly Glu Thr Tyr Thr Ile Glu
            2195            2200            2205

-continued

```
Thr Gly Trp Ile Tyr Asp Met Glu Asn Glu Ser Asp Lys Tyr Tyr Phe
            2210                2215                2220

Asn Pro Glu Thr Lys Lys Ala Cys Lys Gly Ile Asn Leu Ile Asp Asp
2225                2230                2235                2240

Ile Lys Tyr Tyr Phe Asp Glu Lys Gly Ile Met Arg Thr Gly Leu Ile
                2245                2250                2255

Ser Phe Glu Asn Asn Tyr Tyr Phe Asn Glu Asn Gly Glu Met Gln
            2260                2265                2270

Phe Gly Tyr Ile Asn Ile Glu Asp Lys Met Phe Tyr Phe Gly Glu Asp
            2275                2280                2285

Gly Val Met Gln Ile Gly Val Phe Asn Thr Pro Asp Gly Phe Lys Tyr
            2290                2295                2300

Phe Ala His Gln Asn Thr Leu Asp Glu Asn Phe Glu Gly Glu Ser Ile
2305                2310                2315                2320

Asn Tyr Thr Gly Trp Leu Asp Leu Asp Glu Lys Arg Tyr Tyr Phe Thr
                2325                2330                2335

Asp Glu Tyr Ile Ala Ala Thr Gly Ser Val Ile Ile Asp Gly Glu Glu
            2340                2345                2350

Tyr Tyr Phe Asp Pro Asp Thr Ala Gln Leu Val Ile Ser Glu
            2355                2360                2365

<210> SEQ ID NO 3
<211> LENGTH: 966
<212> TYPE: PRT
<213> ORGANISM: Clostridium Difficile

<400> SEQUENCE: 3

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
```

```
                 210                 215                 220
Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
                260                 265                 270

Thr Ser Ile Asn Gly Lys His Phe Tyr Phe Asn Thr Asp Gly Ile Met
            275                 280                 285

Gln Ile Gly Val Phe Lys Gly Pro Asn Gly Phe Glu Tyr Phe Ala Pro
        290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
                340                 345                 350

Phe Asn Thr Asn Thr Ala Val Ala Val Thr Gly Trp Gln Thr Ile Asn
            355                 360                 365

Gly Lys Lys Tyr Tyr Phe Asn Thr Asn Thr Ser Ile Ala Ser Thr Gly
        370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
                420                 425                 430

Gln Asn Arg Phe Leu Tyr Leu His Asp Asn Ile Tyr Tyr Phe Gly Asn
            435                 440                 445

Asn Ser Lys Ala Ala Thr Gly Trp Val Thr Ile Asp Gly Asn Arg Tyr
        450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
                500                 505                 510

Ala Asn Asn Ile Glu Gly Gln Ala Ile Arg Tyr Gln Asn Arg Phe Leu
            515                 520                 525

His Leu Leu Gly Lys Ile Tyr Tyr Phe Gly Asn Asn Ser Lys Ala Val
        530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Phe Glu Ile Asp Gly Val Ile
                565                 570                 575

Tyr Phe Phe Gly Val Asp Gly Val Lys Ala Pro Gly Phe Val Ser Ile
                580                 585                 590

Asn Asp Asn Lys His Tyr Phe Asp Asp Ser Gly Val Met Lys Val Gly
            595                 600                 605

Tyr Thr Glu Ile Asp Gly Lys His Phe Tyr Phe Ala Glu Asn Gly Glu
        610                 615                 620

Met Gln Ile Gly Val Phe Asn Thr Glu Asp Gly Phe Lys Tyr Phe Ala
625                 630                 635                 640
```

His His Asn Glu Asp Leu Gly Asn Glu Glu Gly Glu Ile Ser Tyr
            645                 650                 655

Ser Gly Ile Leu Asn Phe Asn Asn Lys Ile Tyr Tyr Phe Asp Asp Ser
        660                 665                 670

Phe Thr Ala Val Val Gly Trp Lys Asp Leu Glu Asp Gly Ser Lys Tyr
        675                 680                 685

Tyr Phe Asp Glu Asp Thr Ala Glu Ala Tyr Ile Gly Leu Ser Leu Ile
        690                 695                 700

Asn Asp Gly Gln Tyr Tyr Phe Asn Asp Gly Ile Met Gln Val Gly
705                 710                 715                 720

Phe Val Thr Ile Asn Asp Lys Val Phe Tyr Phe Ser Asp Ser Gly Ile
            725                 730                 735

Ile Glu Ser Gly Val Gln Asn Ile Asp Asp Asn Tyr Phe Tyr Ile Asp
            740                 745                 750

Asp Asn Gly Ile Val Gln Ile Gly Val Phe Asp Thr Ser Asp Gly Tyr
        755                 760                 765

Lys Tyr Phe Ala Pro Ala Asn Thr Val Asn Asp Asn Ile Tyr Gly Gln
        770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
            805                 810                 815

Asn Glu Ser Asp Lys Tyr Tyr Phe Asn Pro Glu Thr Lys Lys Ala Cys
            820                 825                 830

Lys Gly Ile Asn Leu Ile Asp Asp Ile Lys Tyr Tyr Phe Asp Glu Lys
            835                 840                 845

Gly Ile Met Arg Thr Gly Leu Ile Ser Phe Glu Asn Asn Asn Tyr Tyr
        850                 855                 860

Phe Asn Glu Asn Gly Glu Met Gln Phe Gly Tyr Ile Asn Ile Glu Asp
865                 870                 875                 880

Lys Met Phe Tyr Phe Gly Glu Asp Gly Val Met Gln Ile Gly Val Phe
            885                 890                 895

Asn Thr Pro Asp Gly Phe Lys Tyr Phe Ala His Gln Asn Thr Leu Asp
            900                 905                 910

Glu Asn Phe Glu Gly Glu Ser Ile Asn Tyr Thr Gly Trp Leu Asp Leu
            915                 920                 925

Asp Glu Lys Arg Tyr Tyr Phe Thr Asp Glu Tyr Ile Ala Ala Thr Gly
        930                 935                 940

Ser Val Ile Ile Asp Gly Glu Glu Tyr Tyr Phe Asp Pro Asp Thr Ala
945                 950                 955                 960

Gln Leu Val Ile Ser Glu
            965

<210> SEQ ID NO 4
<211> LENGTH: 966
<212> TYPE: PRT
<213> ORGANISM: Clostridium Difficile

<400> SEQUENCE: 4

Met Gly Trp Gln Thr Ile Asp Gly Lys Lys Tyr Tyr Phe Asn Thr Asn
 1               5                  10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro

-continued

```
               35                  40                  45
Asn Gly Phe Glu Tyr Phe Ala Pro Ala Asn Thr Asp Ala Asn Asn Ile
 50                  55                  60
Glu Gly Gln Ala Ile Leu Tyr Gln Asn Glu Phe Leu Thr Leu Asn Gly
 65                  70                  75                  80
Lys Lys Tyr Tyr Phe Gly Ser Asp Ser Lys Ala Val Thr Gly Trp Arg
                     85                  90                  95
Ile Ile Asn Asn Lys Lys Tyr Tyr Phe Asn Pro Asn Asn Ala Ile Ala
                    100                 105                 110
Ala Ile His Leu Cys Thr Ile Asn Asn Asp Lys Tyr Tyr Phe Ser Tyr
                115                 120                 125
Asp Gly Ile Leu Gln Asn Gly Tyr Ile Thr Ile Glu Arg Asn Asn Phe
                130                 135                 140
Tyr Phe Asp Ala Asn Asn Glu Ser Lys Met Val Thr Gly Val Phe Lys
145                 150                 155                 160
Gly Pro Asn Gly Phe Glu Tyr Phe Ala Pro Ala Asn Thr His Asn Asn
                    165                 170                 175
Asn Ile Glu Gly Gln Ala Ile Val Tyr Gln Asn Lys Phe Leu Thr Leu
                180                 185                 190
Asn Gly Lys Lys Tyr Tyr Phe Asp Asn Asp Ser Lys Ala Val Thr Gly
                195                 200                 205
Trp Gln Thr Ile Asp Gly Lys Lys Tyr Tyr Phe Asn Leu Asn Thr Ala
210                 215                 220
Glu Ala Ala Thr Gly Trp Gln Thr Ile Asp Gly Lys Lys Tyr Tyr Phe
225                 230                 235                 240
Asn Leu Asn Thr Ala Glu Ala Ala Thr Gly Trp Gln Thr Ile Asp Gly
                245                 250                 255
Lys Lys Tyr Tyr Phe Asn Thr Asn Thr Phe Ile Ala Ser Thr Gly Tyr
                260                 265                 270
Thr Ser Ile Asn Gly Lys His Phe Tyr Phe Asn Thr Asp Gly Ile Met
                275                 280                 285
Gln Ile Gly Val Phe Lys Gly Pro Asn Gly Phe Glu Tyr Phe Ala Pro
290                 295                 300
Ala Asn Thr Asp Ala Asn Asn Ile Glu Gly Gln Ala Ile Leu Tyr Gln
305                 310                 315                 320
Asn Lys Phe Leu Thr Leu Asn Gly Lys Lys Tyr Tyr Phe Gly Ser Asp
                325                 330                 335
Ser Lys Ala Val Thr Gly Leu Arg Thr Ile Asp Gly Lys Lys Tyr Tyr
                340                 345                 350
Phe Asn Thr Asn Thr Ala Val Ala Val Thr Gly Trp Gln Thr Ile Asn
                355                 360                 365
Gly Lys Lys Tyr Tyr Phe Asn Thr Asn Thr Ser Ile Ala Ser Thr Gly
                370                 375                 380
Tyr Thr Ile Ile Ser Gly Lys His Phe Tyr Phe Asn Thr Asp Gly Ile
385                 390                 395                 400
Met Gln Ile Gly Val Phe Lys Gly Pro Asp Gly Phe Glu Tyr Phe Ala
                    405                 410                 415
Pro Ala Asn Thr Asp Ala Asn Asn Ile Glu Gly Gln Ala Ile Arg Tyr
                420                 425                 430
Gln Asn Arg Phe Leu Tyr Leu His Asp Asn Ile Tyr Tyr Phe Gly Asn
                435                 440                 445
Asn Ser Lys Ala Ala Thr Gly Trp Val Thr Ile Asp Gly Asn Arg Tyr
                450                 455                 460
```

-continued

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
            485                 490                 495

Phe Lys Gly Ser Asn Gly Phe Glu Tyr Phe Ala Pro Asn Thr Asp
        500                 505                 510

Ala Asn Asn Ile Glu Gly Gln Ala Ile Arg Tyr Gln Asn Arg Phe Leu
            515                 520                 525

His Leu Leu Gly Lys Ile Tyr Tyr Phe Gly Asn Asn Ser Lys Ala Val
530                 535                 540

Thr Gly Trp Gln Thr Ile Asn Gly Lys Val Tyr Tyr Phe Met Pro Asp
545                 550                 555                 560

Thr Ala Met Ala Ala Gly Gly Leu Asn Gln Ile Gly Asp Tyr Lys
            565                 570                 575

Tyr Tyr Phe Asn Ser Asp Gly Val Met Gln Lys Gly Phe Val Ser Ile
            580                 585                 590

Asn Asp Asn Lys His Tyr Phe Asp Asp Ser Gly Val Met Lys Val Gly
            595                 600                 605

Tyr Thr Glu Ile Asp Gly Lys His Phe Tyr Phe Ala Glu Asn Gly Glu
610                 615                 620

Met Gln Ile Gly Val Phe Asn Thr Glu Asp Gly Phe Lys Tyr Phe Ala
625                 630                 635                 640

His His Asn Glu Asp Leu Gly Asn Glu Glu Gly Glu Ile Ser Tyr
            645                 650                 655

Ser Gly Ile Leu Asn Phe Asn Asn Lys Ile Tyr Tyr Phe Asp Asp Ser
            660                 665                 670

Phe Thr Ala Val Val Gly Trp Lys Asp Leu Glu Asp Gly Ser Lys Tyr
            675                 680                 685

Tyr Phe Asp Glu Asp Thr Ala Glu Ala Tyr Ile Gly Leu Ser Leu Ile
            690                 695                 700

Asn Asp Gly Gln Tyr Tyr Phe Asn Asp Asp Gly Ile Met Gln Val Gly
705                 710                 715                 720

Phe Val Thr Ile Asn Asp Lys Val Phe Tyr Phe Ser Asp Ser Gly Ile
                725                 730                 735

Ile Glu Ser Gly Val Gln Asn Ile Asp Asp Asn Tyr Phe Tyr Ile Asp
            740                 745                 750

Asp Asn Gly Ile Val Gln Ile Gly Val Phe Asp Thr Ser Asp Gly Tyr
            755                 760                 765

Lys Tyr Phe Ala Pro Ala Asn Thr Val Asn Asp Asn Ile Tyr Gly Gln
770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
            805                 810                 815

Asn Glu Ser Asp Lys Tyr Tyr Phe Asn Pro Glu Thr Lys Lys Ala Cys
            820                 825                 830

Lys Gly Ile Asn Leu Ile Asp Asp Ile Lys Tyr Tyr Phe Asp Glu Lys
            835                 840                 845

Gly Ile Met Arg Thr Gly Leu Ile Ser Phe Glu Asn Asn Tyr Tyr
            850                 855                 860

Phe Asn Glu Asn Gly Glu Met Gln Phe Gly Tyr Ile Asn Ile Glu Asp
865                 870                 875                 880

-continued

```
Lys Met Phe Tyr Phe Gly Glu Asp Gly Val Met Gln Ile Gly Val Phe
                885                 890                 895

Asn Thr Pro Asp Gly Phe Lys Tyr Phe Ala His Gln Asn Thr Leu Asp
            900                 905                 910

Glu Asn Phe Glu Gly Glu Ser Ile Asn Tyr Thr Gly Trp Leu Asp Leu
        915                 920                 925

Asp Glu Lys Arg Tyr Tyr Phe Thr Asp Glu Tyr Ile Ala Ala Thr Gly
    930                 935                 940

Ser Val Ile Ile Asp Gly Glu Tyr Tyr Phe Asp Pro Asp Thr Ala
945                 950                 955                 960

Gln Leu Val Ile Ser Glu
                965

<210> SEQ ID NO 5
<211> LENGTH: 833
<212> TYPE: PRT
<213> ORGANISM: Clostridium Difficile

<400> SEQUENCE: 5

Met Gly Trp Gln Thr Ile Asp Gly Lys Lys Tyr Tyr Phe Asn Thr Asn
  1               5                  10                  15

Thr Ala Ile Ala Ser Thr Gly Tyr Thr Ile Ile Asn Gly Lys His Phe
             20                  25                  30

Tyr Phe Asn Thr Asp Gly Ile Met Gln Ile Gly Val Phe Lys Gly Pro
         35                  40                  45

Asn Gly Phe Glu Tyr Phe Ala Pro Ala Asn Thr Asp Ala Asn Asn Ile
     50                  55                  60

Glu Gly Gln Ala Ile Leu Tyr Gln Asn Glu Phe Leu Thr Leu Asn Gly
 65                  70                  75                  80

Lys Lys Tyr Tyr Phe Gly Ser Asp Ser Lys Ala Val Thr Gly Trp Arg
                 85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285
```

-continued

```
Gln Ile Gly Val Phe Lys Gly Pro Asn Gly Phe Glu Tyr Phe Ala Pro
290                 295                 300
Ala Asn Thr Asp Ala Asn Asn Ile Glu Gly Gln Ala Ile Leu Tyr Gln
305                 310                 315                 320
Asn Lys Phe Leu Thr Leu Asn Gly Lys Lys Tyr Tyr Phe Gly Ser Asp
                325                 330                 335
Ser Lys Ala Val Thr Gly Leu Arg Thr Ile Asp Gly Lys Lys Tyr Tyr
            340                 345                 350
Phe Asn Thr Asn Thr Ala Val Ala Val Thr Gly Trp Gln Thr Ile Asn
        355                 360                 365
Gly Lys Lys Tyr Tyr Phe Asn Thr Asn Thr Ser Ile Ala Ser Thr Gly
370                 375                 380
Tyr Thr Ile Ile Ser Gly Lys His Phe Tyr Phe Asn Thr Asp Gly Ile
385                 390                 395                 400
Met Gln Ile Gly Val Phe Lys Gly Pro Asp Gly Phe Glu Tyr Phe Ala
                405                 410                 415
Pro Ala Asn Thr Asp Ala Asn Asn Ile Glu Gly Gln Ala Ile Arg Tyr
            420                 425                 430
Gln Asn Arg Phe Leu Tyr Leu His Asp Asn Ile Tyr Tyr Phe Gly Asn
        435                 440                 445
Asn Ser Lys Ala Ala Thr Gly Trp Val Thr Ile Asp Gly Asn Arg Tyr
450                 455                 460
Tyr Phe Glu Pro Asn Thr Ala Met Gly Ala Asn Gly Tyr Lys Thr Ile
465                 470                 475                 480
Asp Asn Lys Asn Phe Tyr Phe Arg Asn Gly Leu Pro Gln Ile Gly Val
                485                 490                 495
Phe Lys Gly Ser Asn Gly Phe Glu Tyr Phe Ala His His Asn Glu Asp
            500                 505                 510
Leu Gly Asn Glu Glu Gly Glu Glu Ile Ser Tyr Ser Gly Ile Leu Asn
        515                 520                 525
Phe Asn Asn Lys Ile Tyr Tyr Phe Asp Asp Ser Phe Thr Ala Val Val
530                 535                 540
Gly Trp Lys Asp Leu Glu Asp Gly Ser Lys Tyr Tyr Phe Asp Glu Asp
545                 550                 555                 560
Thr Ala Glu Ala Tyr Ile Gly Leu Ser Leu Ile Asn Asp Gly Gln Tyr
                565                 570                 575
Tyr Phe Asn Asp Asp Gly Ile Met Gln Val Gly Phe Val Thr Ile Asn
            580                 585                 590
Asp Lys Val Phe Tyr Phe Ser Asp Ser Gly Ile Ile Glu Ser Gly Val
        595                 600                 605
Gln Asn Ile Asp Asp Asn Tyr Phe Tyr Ile Asp Asp Asn Gly Ile Val
610                 615                 620
Gln Ile Gly Val Phe Asp Thr Ser Asp Gly Tyr Lys Tyr Phe Ala Pro
625                 630                 635                 640
Ala Asn Thr Val Asn Asp Asn Ile Tyr Gly Gln Ala Val Glu Tyr Ser
                645                 650                 655
Gly Leu Val Arg Val Gly Glu Asp Val Tyr Tyr Phe Gly Glu Thr Tyr
            660                 665                 670
Thr Ile Glu Thr Gly Trp Ile Tyr Asp Met Glu Asn Glu Ser Asp Lys
        675                 680                 685
Tyr Tyr Phe Asn Pro Glu Thr Lys Lys Ala Cys Lys Gly Ile Asn Leu
690                 695                 700
```

-continued

```
Ile Asp Asp Ile Lys Tyr Tyr Phe Asp Glu Lys Gly Ile Met Arg Thr
705                 710                 715                 720

Gly Leu Ile Ser Phe Glu Asn Asn Tyr Tyr Phe Asn Glu Asn Gly
            725                 730                 735

Glu Met Gln Phe Gly Tyr Ile Asn Ile Glu Asp Lys Met Phe Tyr Phe
                740                 745                 750

Gly Glu Asp Gly Val Met Gln Ile Gly Val Phe Asn Thr Pro Asp Gly
                755                 760                 765

Phe Lys Tyr Phe Ala His Gln Asn Thr Leu Asp Glu Asn Phe Glu Gly
                770                 775                 780

Glu Ser Ile Asn Tyr Thr Gly Trp Leu Asp Leu Asp Glu Lys Arg Tyr
785                 790                 795                 800

Tyr Phe Thr Asp Glu Tyr Ile Ala Ala Thr Gly Ser Val Ile Ile Asp
                805                 810                 815

Gly Glu Glu Tyr Tyr Phe Asp Pro Asp Thr Ala Gln Leu Val Ile Ser
                820                 825                 830

Glu
```

<210> SEQ ID NO 6
<211> LENGTH: 1057
<212> TYPE: PRT
<213> ORGANISM: Clostridium Difficile

<400> SEQUENCE: 6

```
Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
                20                  25                  30

Tyr Phe Asn Thr Asp Gly Ile Met Gln Ile Gly Val Phe Lys Gly Pro
                35                  40                  45

Asn Gly Phe Glu Tyr Phe Ala Pro Ala Asn Thr Asp Ala Asn Asn Ile
            50                  55                  60

Glu Gly Gln Ala Ile Leu Tyr Gln Asn Glu Phe Leu Thr Leu Asn Gly
65              70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
                100                 105                 110

Ala Ile His Leu Cys Thr Ile Asn Asn Asp Lys Tyr Tyr Phe Ser Tyr
                115                 120                 125

Asp Gly Ile Leu Gln Asn Gly Tyr Ile Thr Ile Glu Arg Asn Asn Phe
                130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
                180                 185                 190

Asn Gly Lys Lys Tyr Tyr Phe Asp Asn Asp Ser Lys Ala Val Thr Gly
                195                 200                 205

Trp Gln Thr Ile Asp Gly Lys Lys Tyr Tyr Phe Asn Leu Asn Thr Ala
                210                 215                 220

Glu Ala Ala Thr Gly Trp Gln Thr Ile Asp Gly Lys Lys Tyr Tyr Phe
225                 230                 235                 240
```

-continued

Asn Leu Asn Thr Ala Glu Ala Thr Gly Trp Gln Thr Ile Asp Gly
            245                 250                 255

Lys Lys Tyr Tyr Phe Asn Thr Asn Thr Phe Ile Ala Ser Thr Gly Tyr
    260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
290                 295                 300

Ala Asn Thr Asp Ala Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
    515                 520                 525

His Leu Leu Gly Lys Ile Tyr Tyr Phe Gly Asn Asn Ser Lys Ala Val
530                 535                 540

Thr Gly Trp Gln Thr Ile Asn Gly Lys Val Tyr Tyr Phe Met Pro Asp
545                 550                 555                 560

Thr Ala Met Ala Ala Gly Gly Glu Thr Ile Ile Asp Asp Lys Asn
                565                 570                 575

Tyr Tyr Phe Asn Gln Ser Gly Val Leu Gln Thr Gly Val Phe Ser Thr
            580                 585                 590

Glu Asp Gly Phe Lys Tyr Phe Ala Pro Ala Asn Thr Leu Asp Glu Asn
        595                 600                 605

Leu Glu Gly Glu Ala Ile Asp Phe Thr Gly Lys Leu Ile Ile Asp Glu
    610                 615                 620

Asn Ile Tyr Tyr Phe Asp Asp Asn Tyr Arg Gly Ala Val Glu Trp Lys
625                 630                 635                 640

Glu Leu Asp Gly Glu Met His Tyr Phe Ser Pro Glu Thr Gly Lys Ala
                645                 650                 655

Phe Lys Gly Leu Asn Gln Ile Gly Asp Tyr Lys Tyr Tyr Phe Asn Ser

```
                    660             665             670
Asp Gly Val Met Gln Lys Gly Phe Val Ser Ile Asn Asp Asn Lys His
            675             680             685

Tyr Phe Asp Asp Ser Gly Val Met Lys Val Gly Tyr Thr Glu Ile Asp
        690             695             700

Gly Lys His Phe Tyr Phe Ala Glu Asn Gly Glu Met Gln Ile Gly Val
705             710             715             720

Phe Asn Thr Glu Asp Gly Phe Lys Tyr Phe Ala His His Asn Glu Asp
                725             730             735

Leu Gly Asn Glu Glu Gly Glu Ile Ser Tyr Ser Gly Ile Leu Asn
            740             745             750

Phe Asn Asn Lys Ile Tyr Tyr Phe Asp Asp Ser Phe Thr Ala Val Val
        755             760             765

Gly Trp Lys Asp Leu Glu Asp Gly Ser Lys Tyr Tyr Phe Asp Glu Asp
    770             775             780

Thr Ala Glu Ala Tyr Ile Gly Leu Ser Leu Ile Asn Asp Gly Gln Tyr
785             790             795             800

Tyr Phe Asn Asp Asp Gly Ile Met Gln Val Gly Phe Val Thr Ile Asn
                805             810             815

Asp Lys Val Phe Tyr Phe Ser Asp Ser Gly Ile Ile Glu Ser Gly Val
            820             825             830

Gln Asn Ile Asp Asp Asn Tyr Phe Tyr Ile Asp Asp Asn Gly Ile Val
        835             840             845

Gln Ile Gly Val Phe Asp Thr Ser Asp Gly Tyr Lys Tyr Phe Ala Pro
    850             855             860

Ala Asn Thr Val Asn Asp Asn Ile Tyr Gly Gln Ala Val Glu Tyr Ser
865             870             875             880

Gly Leu Val Arg Val Gly Glu Asp Val Tyr Tyr Phe Gly Glu Thr Tyr
                885             890             895

Thr Ile Glu Thr Gly Trp Ile Tyr Asp Met Glu Asn Glu Ser Asp Lys
            900             905             910

Tyr Tyr Phe Asn Pro Glu Thr Lys Lys Ala Cys Lys Gly Ile Asn Leu
        915             920             925

Ile Asp Asp Ile Lys Tyr Tyr Phe Asp Glu Lys Gly Ile Met Arg Thr
    930             935             940

Gly Leu Ile Ser Phe Glu Asn Asn Asn Tyr Tyr Phe Asn Glu Asn Gly
945             950             955             960

Glu Met Gln Phe Gly Tyr Ile Asn Ile Glu Asp Lys Met Phe Tyr Phe
                965             970             975

Gly Glu Asp Gly Val Met Gln Ile Gly Val Phe Asn Thr Pro Asp Gly
            980             985             990

Phe Lys Tyr Phe Ala His Gln Asn Thr Leu Asp Glu Asn Phe Glu Gly
        995             1000            1005

Glu Ser Ile Asn Tyr Thr Gly Trp Leu Asp Leu Asp Glu Lys Arg Tyr
    1010            1015            1020

Tyr Phe Thr Asp Glu Tyr Ile Ala Ala Thr Gly Ser Val Ile Ile Asp
1025            1030            1035            1040

Gly Glu Glu Tyr Tyr Phe Asp Pro Asp Thr Ala Gln Leu Val Ile Ser
                1045            1050            1055

Glu

<210> SEQ ID NO 7
<211> LENGTH: 971
```

<212> TYPE: PRT
<213> ORGANISM: Clostridium Difficile

<400> SEQUENCE: 7

```
Met Gly Trp Gln Thr Ile Asp Gly Lys Lys Tyr Tyr Phe Asn Thr Asn
 1               5                  10                  15

Thr Ala Ile Ala Ser Thr Gly Tyr Thr Ile Ile Asn Gly Lys His Phe
             20                  25                  30

Tyr Phe Asn Thr Asp Gly Ile Met Gln Ile Gly Val Phe Lys Gly Pro
         35                  40                  45

Asn Gly Phe Glu Tyr Phe Ala Pro Ala Asn Thr Asp Ala Asn Asn Ile
     50                  55                  60

Glu Gly Gln Ala Ile Leu Tyr Gln Asn Glu Phe Leu Thr Leu Asn Gly
 65                  70                  75                  80

Lys Lys Tyr Tyr Phe Gly Ser Asp Ser Lys Ala Val Thr Gly Trp Arg
                 85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400
```

```
Met Gln Ile Gly Val Phe Lys Gly Pro Asp Gly Phe Glu Tyr Phe Ala
                405             410                 415
Pro Ala Asn Thr Asp Ala Asn Asn Ile Glu Gly Gln Ala Ile Arg Tyr
            420                 425                 430
Gln Asn Arg Phe Leu Tyr Leu His Asp Asn Ile Tyr Tyr Phe Gly Asn
            435                 440                 445
Asn Ser Lys Ala Ala Thr Gly Trp Val Thr Ile Asp Gly Asn Arg Tyr
        450                 455                 460
Tyr Phe Glu Pro Asn Thr Ala Met Gly Ala Asn Gly Tyr Lys Thr Ile
465                 470                 475                 480
Asp Asn Lys Asn Phe Tyr Phe Arg Asn Gly Leu Pro Gln Ile Gly Val
                485                 490                 495
Phe Lys Gly Ser Asn Gly Phe Glu Tyr Phe Ala Pro Ala Asn Thr Asp
            500                 505                 510
Ala Asn Asn Ile Glu Gly Gln Ala Ile Arg Tyr Gln Asn Arg Phe Leu
            515                 520                 525
His Leu Leu Gly Lys Ile Tyr Tyr Phe Gly Asn Asn Ser Lys Ala Val
            530                 535                 540
Thr Gly Trp Gln Thr Ile Asn Gly Lys Val Tyr Tyr Phe Met Pro Asp
545                 550                 555                 560
Thr Ala Met Ala Ala Ala Gly Gly Leu Phe Glu Ile Asp Gly Val Ile
                565                 570                 575
Tyr Phe Phe Gly Val Asp Gly Val Lys Ala Pro Gly Ile Tyr Gly Gly
            580                 585                 590
Gly Phe Val Ser Ile Asn Asp Asn Lys His Tyr Phe Asp Asp Ser Gly
            595                 600                 605
Val Met Lys Val Gly Tyr Thr Glu Ile Asp Gly Lys His Phe Tyr Phe
610                 615                 620
Ala Glu Asn Gly Glu Met Gln Ile Gly Val Phe Asn Thr Glu Asp Gly
625                 630                 635                 640
Phe Lys Tyr Phe Ala His His Asn Glu Asp Leu Gly Asn Glu Glu Gly
            645                 650                 655
Glu Glu Ile Ser Tyr Ser Gly Ile Leu Asn Phe Asn Asn Lys Ile Tyr
            660                 665                 670
Tyr Phe Asp Asp Ser Phe Thr Ala Val Val Gly Trp Lys Asp Leu Glu
            675                 680                 685
Asp Gly Ser Lys Tyr Tyr Phe Asp Glu Asp Thr Ala Glu Ala Tyr Ile
            690                 695                 700
Gly Leu Ser Leu Ile Asn Asp Gly Gln Tyr Tyr Phe Asn Asp Asp Gly
705                 710                 715                 720
Ile Met Gln Val Gly Phe Val Thr Ile Asn Asp Lys Val Phe Tyr Phe
                725                 730                 735
Ser Asp Ser Gly Ile Ile Glu Ser Gly Val Gln Asn Ile Asp Asp Asn
            740                 745                 750
Tyr Phe Tyr Ile Asp Asp Asn Gly Ile Val Gln Ile Gly Val Phe Asp
            755                 760                 765
Thr Ser Asp Gly Tyr Lys Tyr Phe Ala Pro Ala Asn Thr Val Asn Asp
            770                 775                 780
Asn Ile Tyr Gly Gln Ala Val Glu Tyr Ser Gly Leu Val Arg Val Gly
785                 790                 795                 800
Glu Asp Val Tyr Tyr Phe Gly Glu Thr Tyr Thr Ile Glu Thr Gly Trp
                805                 810                 815
```

```
Ile Tyr Asp Met Glu Asn Glu Ser Asp Lys Tyr Tyr Phe Asn Pro Glu
            820                 825                 830

Thr Lys Lys Ala Cys Lys Gly Ile Asn Leu Ile Asp Asp Ile Lys Tyr
            835                 840                 845

Tyr Phe Asp Glu Lys Gly Ile Met Arg Thr Gly Leu Ile Ser Phe Glu
            850                 855                 860

Asn Asn Asn Tyr Tyr Phe Asn Glu Asn Gly Glu Met Gln Phe Gly Tyr
865                 870                 875                 880

Ile Asn Ile Glu Asp Lys Met Phe Tyr Phe Gly Glu Asp Gly Val Met
            885                 890                 895

Gln Ile Gly Val Phe Asn Thr Pro Asp Gly Phe Lys Tyr Phe Ala His
            900                 905                 910

Gln Asn Thr Leu Asp Glu Asn Phe Glu Gly Glu Ser Ile Asn Tyr Thr
            915                 920                 925

Gly Trp Leu Asp Leu Asp Glu Lys Arg Tyr Tyr Phe Thr Asp Glu Tyr
            930                 935                 940

Ile Ala Ala Thr Gly Ser Val Ile Ile Asp Gly Glu Glu Tyr Tyr Phe
945                 950                 955                 960

Asp Pro Asp Thr Ala Gln Leu Val Ile Ser Glu
            965                 970

<210> SEQ ID NO 8
<211> LENGTH: 321
<212> TYPE: PRT
<213> ORGANISM: Clostridium Difficile

<400> SEQUENCE: 8

Met Ala Ser Thr Gly Tyr Thr Ser Ile Asn Gly Lys His Phe Tyr Phe
1               5                   10                  15

Asn Thr Asp Gly Ile Met Gln Ile Gly Val Phe Lys Gly Pro Asn Gly
            20                  25                  30

Phe Glu Tyr Phe Ala Pro Ala Asn Thr Asp Ala Asn Asn Ile Glu Gly
            35                  40                  45

Gln Ala Ile Leu Tyr Gln Asn Lys Phe Leu Thr Leu Asn Gly Lys Lys
    50                  55                  60

Tyr Tyr Phe Gly Ser Asp Ser Lys Ala Val Thr Gly Leu Arg Thr Ile
65                  70                  75                  80

Asp Gly Lys Lys Tyr Tyr Phe Asn Thr Asn Thr Ala Val Ala Val Thr
            85                  90                  95

Gly Trp Gln Thr Ile Asn Gly Lys Lys Tyr Tyr Phe Asn Thr Asn Thr
            100                 105                 110

Ser Ile Ala Ser Thr Gly Tyr Thr Ile Ile Ser Gly Lys His Phe Tyr
            115                 120                 125

Phe Asn Thr Asp Gly Ile Met Gln Ile Gly Val Phe Lys Gly Pro Asp
            130                 135                 140

Gly Phe Glu Tyr Phe Ala Pro Ala Asn Thr Asp Ala Asn Asn Ile Glu
145                 150                 155                 160

Gly Gln Ala Ile Arg Tyr Gln Asn Arg Phe Leu Tyr Leu His Asp Asn
            165                 170                 175

Ile Tyr Tyr Phe Gly Asn Asn Ser Lys Ala Ala Thr Gly Trp Val Thr
            180                 185                 190

Ile Asp Gly Asn Arg Tyr Tyr Phe Glu Pro Asn Thr Ala Met Gly Ala
            195                 200                 205

Asn Gly Tyr Lys Thr Ile Asp Asn Lys Asn Phe Tyr Phe Arg Asn Gly
            210                 215                 220
```

-continued

```
Leu Pro Gln Ile Gly Val Phe Lys Gly Ser Asn Gly Phe Glu Tyr Phe
225                 230                 235                 240

Ala Pro Ala Asn Thr Asp Ala Asn Asn Ile Glu Gly Gln Ala Ile Arg
            245                 250                 255

Tyr Gln Asn Arg Phe Leu His Leu Leu Gly Lys Ile Tyr Tyr Phe Gly
        260                 265                 270

Asn Asn Ser Lys Ala Val Thr Gly Trp Gln Thr Ile Asn Gly Lys Val
    275                 280                 285

Tyr Tyr Phe Met Pro Asp Thr Ala Met Ala Ala Gly Gly Leu Phe
290                 295                 300

Glu Ile Asp Gly Val Ile Tyr Phe Phe Gly Val Asp Gly Val Lys Ala
305                 310                 315                 320

Pro

<210> SEQ ID NO 9
<211> LENGTH: 612
<212> TYPE: PRT
<213> ORGANISM: Clostridium Difficile

<400> SEQUENCE: 9

Met Ile Leu Met Ser Thr Ser Glu Glu Asn Lys Val Ser Gln Val Lys
1               5                   10                  15

Ile Arg Phe Val Asn Val Phe Lys Asp Lys Thr Leu Ala Asn Lys Leu
            20                  25                  30

Ser Phe Asn Phe Ser Asp Lys Gln Asp Val Pro Val Ser Glu Ile Ile
        35                  40                  45

Leu Ser Phe Thr Pro Ser Tyr Tyr Glu Asp Gly Leu Ile Gly Tyr Asp
    50                  55                  60

Leu Gly Leu Val Ser Leu Tyr Asn Glu Lys Phe Tyr Ile Asn Asn Phe
65                  70                  75                  80

Gly Met Met Val Ser Gly Leu Ile Tyr Ile Asn Asp Ser Leu Tyr Tyr
                85                  90                  95

Phe Lys Pro Pro Val Asn Asn Leu Ile Thr Gly Phe Val Thr Val Gly
            100                 105                 110

Asp Asp Lys Tyr Tyr Phe Asn Pro Ile Asn Gly Gly Ala Ala Ser Ile
        115                 120                 125

Gly Glu Thr Ile Ile Asp Asp Lys Asn Tyr Tyr Phe Asn Gln Ser Gly
    130                 135                 140

Val Leu Gln Thr Gly Val Phe Ser Thr Glu Asp Gly Phe Lys Tyr Phe
145                 150                 155                 160

Ala Pro Ala Asn Thr Leu Asp Glu Asn Leu Glu Gly Glu Ala Ile Asp
                165                 170                 175

Phe Thr Gly Lys Leu Ile Ile Asp Glu Asn Ile Tyr Tyr Phe Asp Asp
            180                 185                 190

Asn Tyr Arg Gly Ala Val Glu Trp Lys Glu Leu Asp Gly Glu Met His
        195                 200                 205

Tyr Phe Ser Pro Glu Thr Gly Lys Ala Phe Lys Gly Leu Asn Gln Ile
    210                 215                 220

Gly Asp Tyr Lys Tyr Tyr Phe Asn Ser Asp Gly Val Met Gln Lys Gly
225                 230                 235                 240

Phe Val Ser Ile Asn Asp Asn Lys His Tyr Phe Asp Asp Ser Gly Val
                245                 250                 255

Met Lys Val Gly Tyr Thr Glu Ile Asp Gly Lys His Phe Tyr Phe Ala
            260                 265                 270
```

```
Glu Asn Gly Glu Met Gln Ile Gly Val Phe Asn Thr Glu Asp Gly Phe
            275                 280                 285

Lys Tyr Phe Ala His His Asn Glu Asp Leu Gly Asn Glu Glu Gly Glu
        290                 295                 300

Glu Ile Ser Tyr Ser Gly Ile Leu Asn Phe Asn Asn Lys Ile Tyr Tyr
305                 310                 315                 320

Phe Asp Asp Ser Phe Thr Ala Val Val Gly Trp Lys Asp Leu Glu Asp
                325                 330                 335

Gly Ser Lys Tyr Tyr Phe Asp Glu Asp Thr Ala Glu Ala Tyr Ile Gly
                340                 345                 350

Leu Ser Leu Ile Asn Asp Gly Gln Tyr Tyr Phe Asn Asp Asp Gly Ile
            355                 360                 365

Met Gln Val Gly Phe Val Thr Ile Asn Asp Lys Val Phe Tyr Phe Ser
    370                 375                 380

Asp Ser Gly Ile Ile Glu Ser Gly Val Gln Asn Ile Asp Asp Asn Tyr
385                 390                 395                 400

Phe Tyr Ile Asp Asp Asn Gly Ile Val Gln Ile Gly Val Phe Asp Thr
                405                 410                 415

Ser Asp Gly Tyr Lys Tyr Phe Ala Pro Ala Asn Thr Val Asn Asp Asn
            420                 425                 430

Ile Tyr Gly Gln Ala Val Glu Tyr Ser Gly Leu Val Arg Val Gly Glu
        435                 440                 445

Asp Val Tyr Tyr Phe Gly Glu Thr Tyr Thr Ile Glu Thr Gly Trp Ile
    450                 455                 460

Tyr Asp Met Glu Asn Glu Ser Asp Lys Tyr Tyr Phe Asn Pro Glu Thr
465                 470                 475                 480

Lys Lys Ala Cys Lys Gly Ile Asn Leu Ile Asp Asp Ile Lys Tyr Tyr
                485                 490                 495

Phe Asp Glu Lys Gly Ile Met Arg Thr Gly Leu Ile Ser Phe Glu Asn
            500                 505                 510

Asn Asn Tyr Tyr Phe Asn Glu Asn Gly Glu Met Gln Phe Gly Tyr Ile
        515                 520                 525

Asn Ile Glu Asp Lys Met Phe Tyr Phe Gly Glu Asp Gly Val Met Gln
    530                 535                 540

Ile Gly Val Phe Asn Thr Pro Asp Gly Phe Lys Tyr Phe Ala His Gln
545                 550                 555                 560

Asn Thr Leu Asp Glu Asn Phe Glu Gly Glu Ser Ile Asn Tyr Thr Gly
                565                 570                 575

Trp Leu Asp Leu Asp Glu Lys Arg Tyr Tyr Phe Thr Asp Glu Tyr Ile
            580                 585                 590

Ala Ala Thr Gly Ser Val Ile Ile Asp Gly Glu Glu Tyr Tyr Phe Asp
        595                 600                 605

Pro Asp Thr Ala
    610

<210> SEQ ID NO 10
<211> LENGTH: 3339
<212> TYPE: DNA
<213> ORGANISM: Clostridium Difficile

<400> SEQUENCE: 10
atggcaaccg gttggcagac catcgatggc aaaaaatatt attttaatac caacaccgca      60
attgcaagca ccggctatac cattatcaac ggcaaacact ttatttttaa caccgacggc     120
```

| | |
|---|---|
| attatgcaga ttggtgtgtt taaaggtccg aacggctttg aatactttgc accggcaaat | 180 |
| accgatgcca ataatattga aggccaggcc attctgtatc agaatgaatt tctgaccctg | 240 |
| aacggcaaaa aatactactt tggcagcgat agcaaagcag ttaccggttg cgcatcatc | 300 |
| aacaataaga aatattactt caacccgaat aatgcaattg cagcaattca tctgtgcacc | 360 |
| attaacaacg acaaatatta tttcagctat gacggtattc tgcagaatgg ctacattacc | 420 |
| atcgaacgca caacttttta tttcgatgcc aacaacgaaa gcaaaatggt gaccggtgtt | 480 |
| ttcaaaggcc ctaatggttt tgagtatttc gctccggcaa acacccataa taacaacatt | 540 |
| gaaggtcagg cgatcgttta tcagaacaaa ttcctgacgc tgaatggtaa gaaatactat | 600 |
| ttcgataatg acagcaaagc cgtgaccggc tggcagacaa ttgacgggaa gaaatattac | 660 |
| tttaatctga ataccgcaga agcagcaacc ggttggcaaa cgatcgacgg taaaaagtac | 720 |
| tacttcaacc tgaacacagc cgaagcagcc acaggatggc agactattga tggaaaaaaa | 780 |
| tactatttca acaccaacac ctttattgca tctaccggtt ataccagcat taacggtaaa | 840 |
| catttctact tcaacaccga tggtatcatg cagatcggcg ttttcaaagg tccaaatggt | 900 |
| ttcgaatact tgcccctgc caatacagat gcaaataaca tcgagggtca ggcaatcctg | 960 |
| taccaaaaca aatttctgac cctgaatggg aaaaaatatt actttggtag cgattctaaa | 1020 |
| gccgttaccg gtctgcgtac cattgatggt aaaaaatact actttaatac gaatacagcc | 1080 |
| gttgcggtta caggctggca gaccattaac gggaaaaaat actatttaa cacaaatacc | 1140 |
| agcattgcct caacgggtta taccattatt tcgggtaaac acttctactt taataccgat | 1200 |
| ggtattatgc aaatcggagt ctttaaagga cctgatgggt tcgaatatt tgcgcctgcg | 1260 |
| aacactgatg cgaacaatat cgaaggacag gcaatccgct atcagaatcg ctttctgtat | 1320 |
| ctgcacgaca acatctatta ttttggcaac aattcaaaag cagccaccgg ctgggttaca | 1380 |
| attgatggca accgctacta tttcgaaccg aataccgcaa tgggtgcaaa tggctacaaa | 1440 |
| accatcgata taaaaatttt ctattttcgc aacggtctgc cgcagatcgg ggtatttaaa | 1500 |
| ggtagcaacg gcttcgaata cttcgctcca gcgaatacgg acgcgaacaa tattgagggt | 1560 |
| caagcgattc gttatcaaaa ccgttttctg catctgctgg gcaaaatcta ctactttggc | 1620 |
| aataacagta aagcagttac tggatggcag acaatcaatg gtaaagtgta ctatttatg | 1680 |
| ccggataccg ccatggcagc agccggtggt ctgtttgaaa ttgatggcgt gatctatttt | 1740 |
| tttggtgtgg atggtgttaa agcaccggga atatacggtg gtaccggctt tgtgaccgtg | 1800 |
| ggtgatgata aatactattt caatccgatt aacggtggtg cagcgagcat tggcgaaacc | 1860 |
| atcatcgatg acaaaaacta ttatttcaac cagagcggtg tgctgcagac cggtgtgttt | 1920 |
| agcaccgaag atggctttaa atatttttgcg ccagcgaaca ccctggatga aaacctggaa | 1980 |
| ggcgaagcga ttgattttac cggcaaactg atcatcgatg aaaacatcta ttacttcgat | 2040 |
| gataactatc gtggtgcggt ggaatggaaa gaactggatg cgaaatgca ttattttct | 2100 |
| ccggaaaccg gtaaagcgtt taaggcctg aaccagatcg cgattacaa atactacttc | 2160 |
| aacagcgatg gcgtgatgca gaaaggcttt gtgagcatca cgataacaa acactatttc | 2220 |
| gatgatagcg gtgtgatgaa agtgggctat accgaaattg atggcaaaca tttctacttc | 2280 |
| gcggaaaacg gcgaaatgca gattggcgtg ttcaataccg aagatggttt caaatacttc | 2340 |
| gcgcaccata cgaagatct gggtaacgaa gaaggcgaag aaattagcta tagcggcatc | 2400 |
| ctgaacttca caacaaaat ctactacttt gatgatagct ttaccgcggt ggtgggctgg | 2460 |
| aaagatctgg aagatggcag caaatattat ttcgatgaag ataccgcgga agcgtatatt | 2520 |

-continued

```
ggcctgagcc tgattaacga tggccagtac tattttaacg atgatggcat tatgcaggtg    2580
ggtttcgtga ccattaatga taaagtgttc tatttcagcg atagcggcat tattgaaagc    2640
ggcgtgcaga acattgatga taactacttc tacatcgatg ataacggcat tgtgcagatc    2700 ggcgttttg  ataccagcga tggctacaaa tatttcgcac cggccaatac cgtgaacgat    2760
aacatttatg ccaggcggt  ggaatatagc ggtctggtgc gtgtgggcga agatgtgtat    2820
tatttcggcg aaacctatac catcgaaacc ggctggattt atgatatgga aaacgaaagc    2880
gataaatatt actttaatcc ggaaacgaaa aaagcgtgca aaggcattaa cctgatcgat    2940
gatatcaaat actattttga tgaaaaaggc attatgcgta ccggtctgat tagcttcgaa    3000
aacaacaact attacttcaa cgaaaacggt gaaatgcagt tcggctacat caacatcgaa    3060
gataaaatgt tctacttcgg cgaagatggt gttatgcaga ttggtgtttt taacaccccg    3120
gatggcttca atactttgc  ccatcagaat accctggatg aaaatttcga aggtgaaagc    3180
attaactata ccggctggct ggatctggat gaaaaacgct actacttcac cgatgaatac    3240
attgcggcga ccggcagcgt gattattgat ggcgaagaat actacttcga tccggatacc    3300
gcgcagctgg tgattagcga acatcatcat catcaccat                           3339
```

<210> SEQ ID NO 11
<211> LENGTH: 1113
<212> TYPE: PRT
<213> ORGANISM: Clostridium Difficile

<400> SEQUENCE: 11

```
Met Ala Thr Gly Trp Gln Thr Ile Asp Gly Lys Lys Tyr Tyr Phe Asn
  1               5                  10                  15

Thr Asn Thr Ala Ile Ala Ser Thr Gly Tyr Thr Ile Ile Asn Gly Lys
                 20                  25                  30

His Phe Tyr Phe Asn Thr Asp Gly Ile Met Gln Ile Gly Val Phe Lys
             35                  40                  45

Gly Pro Asn Gly Phe Glu Tyr Phe Ala Pro Ala Asn Thr Asp Ala Asn
         50                  55                  60

Asn Ile Glu Gly Gln Ala Ile Leu Tyr Gln Asn Glu Phe Leu Thr Leu
 65                  70                  75                  80

Asn Gly Lys Lys Tyr Tyr Phe Gly Ser Asp Ser Lys Ala Val Thr Gly
                 85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
            115                 120                 125

Ser Tyr Asp Gly Ile Leu Gln Asn Gly Tyr Ile Thr Ile Glu Arg Asn
            130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
            195                 200                 205

Thr Gly Trp Gln Thr Ile Asp Gly Lys Lys Tyr Tyr Phe Asn Leu Asn
            210                 215                 220
```

-continued

```
Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
            245                 250                 255

Asp Gly Lys Lys Tyr Tyr Phe Asn Thr Asn Thr Phe Ile Ala Ser Thr
        260                 265                 270

Gly Tyr Thr Ser Ile Asn Gly Lys His Phe Tyr Phe Asn Thr Asp Gly
    275                 280                 285

Ile Met Gln Ile Gly Val Phe Lys Gly Pro Asn Gly Phe Glu Tyr Phe
290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
            325                 330                 335

Ser Asp Ser Lys Ala Val Thr Gly Leu Arg Thr Ile Asp Gly Lys Lys
        340                 345                 350

Tyr Tyr Phe Asn Thr Asn Thr Ala Val Ala Val Thr Gly Trp Gln Thr
    355                 360                 365

Ile Asn Gly Lys Lys Tyr Tyr Phe Asn Thr Asn Thr Ser Ile Ala Ser
370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
            405                 410                 415

Phe Ala Pro Ala Asn Thr Asp Ala Asn Asn Ile Glu Gly Gln Ala Ile
        420                 425                 430

Arg Tyr Gln Asn Arg Phe Leu Tyr Leu His Asp Asn Ile Tyr Tyr Phe
    435                 440                 445

Gly Asn Asn Ser Lys Ala Ala Thr Gly Trp Val Thr Ile Asp Gly Asn
450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
            485                 490                 495

Gly Val Phe Lys Gly Ser Asn Gly Phe Glu Tyr Phe Ala Pro Ala Asn
        500                 505                 510

Thr Asp Ala Asn Asn Ile Glu Gly Gln Ala Ile Arg Tyr Gln Asn Arg
    515                 520                 525

Phe Leu His Leu Leu Gly Lys Ile Tyr Tyr Phe Gly Asn Asn Ser Lys
530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
            565                 570                 575

Val Ile Tyr Phe Phe Gly Val Asp Gly Val Lys Ala Pro Gly Ile Tyr
        580                 585                 590

Gly Gly Thr Gly Phe Val Thr Val Gly Asp Asp Lys Tyr Tyr Phe Asn
    595                 600                 605

Pro Ile Asn Gly Gly Ala Ala Ser Ile Gly Glu Thr Ile Ile Asp Asp
610                 615                 620

Lys Asn Tyr Tyr Phe Asn Gln Ser Gly Val Leu Gln Thr Gly Val Phe
625                 630                 635                 640

Ser Thr Glu Asp Gly Phe Lys Tyr Phe Ala Pro Ala Asn Thr Leu Asp
```

-continued

```
                645                 650                 655
Glu Asn Leu Glu Gly Glu Ala Ile Asp Phe Thr Gly Lys Leu Ile Ile
            660                 665                 670

Asp Glu Asn Ile Tyr Tyr Phe Asp Asp Asn Tyr Arg Gly Ala Val Glu
        675                 680                 685

Trp Lys Glu Leu Asp Gly Glu Met His Tyr Phe Ser Pro Glu Thr Gly
    690                 695                 700

Lys Ala Phe Lys Gly Leu Asn Gln Ile Gly Asp Tyr Lys Tyr Tyr Phe
705                 710                 715                 720

Asn Ser Asp Gly Val Met Gln Lys Gly Phe Val Ser Ile Asn Asp Asn
                725                 730                 735

Lys His Tyr Phe Asp Asp Ser Gly Val Met Lys Val Gly Tyr Thr Glu
            740                 745                 750

Ile Asp Gly Lys His Phe Tyr Phe Ala Glu Asn Gly Glu Met Gln Ile
        755                 760                 765

Gly Val Phe Asn Thr Glu Asp Gly Phe Lys Tyr Phe Ala His His Asn
    770                 775                 780

Glu Asp Leu Gly Asn Glu Glu Gly Glu Glu Ile Ser Tyr Ser Gly Ile
785                 790                 795                 800

Leu Asn Phe Asn Asn Lys Ile Tyr Tyr Phe Asp Asp Ser Phe Thr Ala
                805                 810                 815

Val Val Gly Trp Lys Asp Leu Glu Asp Gly Ser Lys Tyr Tyr Phe Asp
            820                 825                 830

Glu Asp Thr Ala Glu Ala Tyr Ile Gly Leu Ser Leu Ile Asn Asp Gly
        835                 840                 845

Gln Tyr Tyr Phe Asn Asp Asp Gly Ile Met Gln Val Gly Phe Val Thr
    850                 855                 860

Ile Asn Asp Lys Val Phe Tyr Phe Ser Asp Ser Gly Ile Ile Glu Ser
865                 870                 875                 880

Gly Val Gln Asn Ile Asp Asp Asn Tyr Phe Tyr Ile Asp Asp Asn Gly
                885                 890                 895

Ile Val Gln Ile Gly Val Phe Asp Thr Ser Asp Gly Tyr Lys Tyr Phe
            900                 905                 910

Ala Pro Ala Asn Thr Val Asn Asp Asn Ile Tyr Gly Gln Ala Val Glu
        915                 920                 925

Tyr Ser Gly Leu Val Arg Val Gly Glu Asp Val Tyr Tyr Phe Gly Glu
    930                 935                 940

Thr Tyr Thr Ile Glu Thr Gly Trp Ile Tyr Asp Met Glu Asn Glu Ser
945                 950                 955                 960

Asp Lys Tyr Tyr Phe Asn Pro Glu Thr Lys Lys Ala Cys Lys Gly Ile
                965                 970                 975

Asn Leu Ile Asp Asp Ile Lys Tyr Tyr Phe Asp Glu Lys Gly Ile Met
            980                 985                 990

Arg Thr Gly Leu Ile Ser Phe Glu Asn Asn Asn Tyr Tyr Phe Asn Glu
        995                 1000                1005

Asn Gly Glu Met Gln Phe Gly Tyr Ile Asn Ile Glu Asp Lys Met Phe
    1010                1015                1020

Tyr Phe Gly Glu Asp Gly Val Met Gln Ile Gly Val Phe Asn Thr Pro
1025                1030                1035                1040

Asp Gly Phe Lys Tyr Phe Ala His Gln Asn Thr Leu Asp Glu Asn Phe
                1045                1050                1055

Glu Gly Glu Ser Ile Asn Tyr Thr Gly Trp Leu Asp Leu Asp Glu Lys
            1060                1065                1070
```

Arg Tyr Tyr Phe Thr Asp Glu Tyr Ile Ala Ala Thr Gly Ser Val Ile
    1075                1080                1085

Ile Asp Gly Glu Glu Tyr Tyr Phe Asp Pro Asp Thr Ala Gln Leu Val
    1090                1095                1100

Ile Ser Glu His His His His His His
1105                1110

<210> SEQ ID NO 12
<211> LENGTH: 3324
<212> TYPE: DNA
<213> ORGANISM: Clostridium Difficile

<400> SEQUENCE: 12

```
atggcaaccg gttggcagac catcgatggc aaaaaatatt attttaatac caacaccgca      60
attgcaagca ccggctatac cattatcaac ggcaaacact tttattttaa caccgacggc     120
attatgcaga ttggtgtgtt taaaggtccg aacggctttg aatactttgc accggcaaat     180
accgatgcca taatattga aggccaggcc attctgtatc agaatgaatt tctgaccctg     240
aacggcaaaa aatactactt tggcagcgat agcaaagcag ttaccggttg cgcatcatc     300
aacaataaga aatattactt caacccgaat aatgcaattg cagcaattca tctgtgcacc     360
attaacaacg acaaatatta tttcagctat gacggtattc tgcagaatgg ctacattacc     420
atcgaacgca caacttttta tttcgatgcc aacaacgaaa gcaaatggt gaccggtgtt     480
ttcaaaggcc ctaatggttt tgagtatttc gctccggcaa cacccataa taacaacatt     540
gaaggtcagg cgatcgttta tcagaacaaa ttcctgacgc tgaatggtaa gaaatactat     600
ttcgataatg acagcaaagc cgtgaccggc tggcagacaa ttgacgggaa gaaatattac     660
tttaatctga ataccgcaga agcagcaacc ggttggcaaa cgatcgacgg taaaaagtac     720
tacttcaacc tgaacacagc cgaagcagcc acaggatggc agactattga tggaaaaaaa     780
tactatttca acaccaacac ctttattgca tctaccggtt ataccagcat aacggtaaa     840
catttctact tcaacaccga tggtatcatg cagatcggcg ttttcaaagg tccaaatggt     900
ttcgaatact tgccccctgc aatacagat gcaaataaca tcgagggtca ggcaatcctg     960
taccaaaaca aatttctgac cctgaatggg aaaaaatatt actttggtag cgattctaaa    1020
gccgttaccg tctgcgtac cattgatggt aaaaaatact actttaatac gaatacagcc    1080
gttgcggtta caggctggca gaccattaac gggaaaaaat actattttaa cacaaatacc    1140
agcattgcct caacgggtta taccattatt tcgggtaaac acttctactt taataccgat    1200
ggtattatgc aaatcggagt ctttaaagga cctgatgggt tcgaatattt tgcgcctgcg    1260
aacactgatg cgaacaatat cgaaggacag gcaatccgct atcagaatcg ctttctgtat    1320
ctgcacgaca acatctatta ttttggcaac aattcaaaag cagccaccgg ctgggttaca    1380
attgatggca accgctacta tttcgaaccg aataccgcaa tgggtgcaaa tggctacaaa    1440
accatcgata taaaaatttt ctattttcgc aacggtctgc cgcagatcgg ggtatttaaa    1500
ggtagcaacg gcttcgaata cttcgctcca gcgaatacgg acgcgaacaa tattgagggt    1560
caagcgattc gttatcaaaa ccgttttctg catctgctgg gcaaaatcta ctactttggc    1620
aataacagta aagcagttac tggatggcag acaatcaatg gtaaagtgta ctattttatg    1680
ccggataccg ccatggcagc agccggtggt ctgtttgaaa ttgatggcgt gatctatttt    1740
tttggtgtgg atggtgttaa agcagttacc ggctttgtga ccgtgggtga tgataaatac    1800
tatttcaatc cgattaacgg tggtgcagcg agcattggcg aaaccatcat cgatgacaaa    1860
```

-continued

```
aactattatt tcaaccagag cggtgtgctg cagaccggtg tgtttagcac cgaagatggc   1920
tttaaatatt ttgcgccagc gaacaccctg gatgaaaacc tggaaggcga agcgattgat   1980
tttaccggca aactgatcat cgatgaaaac atctattact tcgatgataa ctatcgtggt   2040
gcggtggaat ggaaagaact ggatggcgaa atgcattatt tttctccgga aaccggtaaa   2100
gcgtttaaag gcctgaacca gatcggcgat tacaaatact acttcaacag cgatggcgtg   2160
atgcagaaag gctttgtgag catcaacgat aacaaacact atttcgatga tagcggtgtg   2220
atgaaagtgg gctataccga aattgatggc aaacatttct acttcgcgga aaacggcgaa   2280
atgcagattg gcgtgttcaa taccgaagat ggtttcaaat acttcgcgca ccataacgaa   2340
gatctgggta acgaagaagg cgaagaaatt agctatagcg gcatcctgaa cttcaacaac   2400
aaaatctact actttgatga tagctttacc gcggtggtgg gctggaaaga tctggaagat   2460
ggcagcaaat attatttcga tgaagatacc gcggaagcgt atattggcct gagcctgatt   2520
aacgatggcc agtactattt taacgatgat ggcattatgc aggtgggttt cgtgaccatt   2580
aatgataaag tgttctattt cagcgatagc ggcattattg aaagcggcgt gcagaacatt   2640
gatgataact acttctacat cgatgataac ggcattgtgc agatcggcgt tttgatacc    2700 agcgatggct acaaatattt cgcaccggcc aataccgtga acgataacat ttatggccag   2760
gcggtggaat atagcggtct ggtgcgtgtg ggcgaagatg tgtattattt cggcgaaacc   2820
tataccatcg aaaccggctg gatttatgat atggaaaacg aaagcgataa atattacttt   2880
aatccggaaa cgaaaaaagc gtgcaaaggc attaacctga tcgatgatat caaatactat   2940
tttgatgaaa aaggcattat gcgtaccggt ctgattagct tcgaaaacaa caactattac   3000
ttcaacgaaa acggtgaaat gcagttcggc tacatcaaca tcgaagataa aatgttctac   3060
ttcggcgaag atggtgttat gcagattggt gtttttaaca ccccggatgg cttcaaatac   3120
tttgcccatc agaataccct ggatgaaaat ttcgaaggtg aaagcattaa ctataccggc   3180
tggctggatc tggatgaaaa acgctactac ttcaccgatg aatacattgc ggcgaccggc   3240
agcgtgatta ttgatggcga agaatactac ttcgatccgg ataccgcgca gctggtgatt   3300
agcgaacatc atcatcatca ccat                                          3324
```

<210> SEQ ID NO 13
<211> LENGTH: 1108
<212> TYPE: PRT
<213> ORGANISM: Clostridium Difficile

<400> SEQUENCE: 13

```
Met Ala Thr Gly Trp Gln Thr Ile Asp Gly Lys Lys Tyr Tyr Phe Asn
 1               5                  10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45

Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110
```

```
Ile Ala Ala Ile His Leu Cys Thr Ile Asn Asn Asp Lys Tyr Tyr Phe
            115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn
    450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
        515                 520                 525
```

-continued

Phe Leu His Leu Leu Gly Lys Ile Tyr Tyr Phe Gly Asn Asn Ser Lys
    530                 535                 540

Ala Val Thr Gly Trp Gln Thr Ile Asn Gly Lys Val Tyr Tyr Phe Met
545                 550                 555                 560

Pro Asp Thr Ala Met Ala Ala Gly Gly Leu Phe Glu Ile Asp Gly
                565                 570                 575

Val Ile Tyr Phe Phe Gly Val Asp Gly Val Lys Ala Val Thr Gly Phe
            580                 585                 590

Val Thr Val Gly Asp Asp Lys Tyr Tyr Phe Asn Pro Ile Asn Gly Gly
        595                 600                 605

Ala Ala Ser Ile Gly Glu Thr Ile Ile Asp Asp Lys Asn Tyr Tyr Phe
    610                 615                 620

Asn Gln Ser Gly Val Leu Gln Thr Gly Val Phe Ser Thr Glu Asp Gly
625                 630                 635                 640

Phe Lys Tyr Phe Ala Pro Ala Asn Thr Leu Asp Glu Asn Leu Glu Gly
                645                 650                 655

Glu Ala Ile Asp Phe Thr Gly Lys Leu Ile Ile Asp Glu Asn Ile Tyr
            660                 665                 670

Tyr Phe Asp Asp Asn Tyr Arg Gly Ala Val Glu Trp Lys Glu Leu Asp
        675                 680                 685

Gly Glu Met His Tyr Phe Ser Pro Glu Thr Gly Lys Ala Phe Lys Gly
    690                 695                 700

Leu Asn Gln Ile Gly Asp Tyr Lys Tyr Tyr Phe Asn Ser Asp Gly Val
705                 710                 715                 720

Met Gln Lys Gly Phe Val Ser Ile Asn Asp Asn Lys His Tyr Phe Asp
                725                 730                 735

Asp Ser Gly Val Met Lys Val Gly Tyr Thr Glu Ile Asp Gly Lys His
            740                 745                 750

Phe Tyr Phe Ala Glu Asn Gly Glu Met Gln Ile Gly Val Phe Asn Thr
        755                 760                 765

Glu Asp Gly Phe Lys Tyr Phe Ala His His Asn Glu Asp Leu Gly Asn
    770                 775                 780

Glu Glu Gly Glu Glu Ile Ser Tyr Ser Gly Ile Leu Asn Phe Asn Asn
785                 790                 795                 800

Lys Ile Tyr Tyr Phe Asp Asp Ser Phe Thr Ala Val Val Gly Trp Lys
                805                 810                 815

Asp Leu Glu Asp Gly Ser Lys Tyr Tyr Phe Asp Glu Asp Thr Ala Glu
            820                 825                 830

Ala Tyr Ile Gly Leu Ser Leu Ile Asn Asp Gly Gln Tyr Tyr Phe Asn
        835                 840                 845

Asp Asp Gly Ile Met Gln Val Gly Phe Val Thr Ile Asn Asp Lys Val
    850                 855                 860

Phe Tyr Phe Ser Asp Ser Gly Ile Ile Glu Ser Gly Val Gln Asn Ile
865                 870                 875                 880

Asp Asp Asn Tyr Phe Tyr Ile Asp Asn Gly Ile Val Gln Ile Gly
                885                 890                 895

Val Phe Asp Thr Ser Asp Gly Tyr Lys Tyr Phe Ala Pro Ala Asn Thr
            900                 905                 910

Val Asn Asp Asn Ile Tyr Gly Gln Ala Val Glu Tyr Ser Gly Leu Val
        915                 920                 925

Arg Val Gly Glu Asp Val Tyr Tyr Phe Gly Glu Thr Tyr Thr Ile Glu
    930                 935                 940

Thr Gly Trp Ile Tyr Asp Met Glu Asn Glu Ser Asp Lys Tyr Tyr Phe

```
                  945                 950                 955                 960
            Asn Pro Glu Thr Lys Lys Ala Cys Lys Gly Ile Asn Leu Ile Asp Asp
                            965                 970                 975
            Ile Lys Tyr Tyr Phe Asp Glu Lys Gly Ile Met Arg Thr Gly Leu Ile
                            980                 985                 990
            Ser Phe Glu Asn Asn Asn Tyr Tyr Phe Asn Glu Asn Gly Glu Met Gln
                            995                 1000                1005
            Phe Gly Tyr Ile Asn Ile Glu Asp Lys Met Phe Tyr Phe Gly Glu Asp
                            1010                1015                1020
            Gly Val Met Gln Ile Gly Val Phe Asn Thr Pro Asp Gly Phe Lys Tyr
                            1025                1030                1035                1040
            Phe Ala His Gln Asn Thr Leu Asp Glu Asn Phe Glu Gly Glu Ser Ile
                                1045                1050                1055
            Asn Tyr Thr Gly Trp Leu Asp Leu Asp Glu Lys Arg Tyr Tyr Phe Thr
                                1060                1065                1070
            Asp Glu Tyr Ile Ala Ala Thr Gly Ser Val Ile Ile Asp Gly Glu Glu
                                1075                1080                1085
            Tyr Tyr Phe Asp Pro Asp Thr Ala Gln Leu Val Ile Ser Glu His His
                                1090                1095                1100
            His His His His
            1105

<210> SEQ ID NO 14
<211> LENGTH: 3387
<212> TYPE: DNA
<213> ORGANISM: Clostridium Difficile

<400> SEQUENCE: 14
atggcaaccg gttggcagac catcgatggc aaaaaatatt attttaatac caacaccgca      60
attgcaagca ccggctatac cattatcaac ggcaaacact tttattttaa caccgacggc     120
attatgcaga ttggtgtgtt taaaggtccg aacggctttg aatactttgc accggcaaat     180
accgatgcca ataatattga aggccaggcc attctgtatc agaatgaatt tctgaccctg     240
aacggcaaaa aatactactt tggcagcgat agcaaagcag ttaccggttg cgcatcatc      300
aacaataaga aatattactt caacccgaat aatgcaattg cagcaattca tctgtgcacc     360
attaacaacg acaaatatta tttcagctat gacggtattc tgcagaatgg ctacattacc     420
atcgaacgca caacttttta tttcgatgcc aacaacgaaa gcaaatggt gaccggtgtt      480
ttcaaaggcc taatggtttt tgagtatttc gctccggcaa acacccataa taacaacatt     540
gaaggtcagg cgatcgttta tcagaacaaa ttcctgacgc tgaatggtaa aaatactat      600
ttcgataatg acagcaaagc cgtgaccggc tggcagacaa ttgacgggaa gaaatattac     660
tttaatctga ataccgcaga agcagcaacc ggttggcaaa cgatcgacgg taaaaagtac     720
tacttcaacc tgaacacagc cgaagcagcc acaggatggc agactattga tggaaaaaaa     780
tactatttca acaccaacac ctttattgca tctaccggtt ataccagcat taacggtaaa     840
catttctact caacaccga tggtatcatg cagatcggcg ttttcaaagg tccaaatggt     900
ttcgaatact tgcccctgc caatacagat gcaaataaca tcgagggtca ggcaatcctg     960
taccaaaaca aatttctgac cctgaatggg aaaaaatatt actttggtag cgattctaaa    1020
gccgttaccg gtctgcgtac cattgatggt aaaaaatact actttaatac gaatacagcc    1080
gttgcggtta caggctggca gaccattaac gggaaaaaat actatttaa cacaaatacc    1140
agcattgcct caacgggtta taccattatt tcgggtaaac acttctactt taataccgat    1200
```

```
ggtattatgc aaatcggagt ctttaaagga cctgatgggt tcgaatattt tgcgcctgcg    1260
aacactgatg cgaacaatat cgaaggacag gcaatccgct atcagaatcg ctttctgtat    1320
ctgcacgaca acatctatta ttttggcaac aattcaaaag cagccaccgg ctgggttaca    1380
attgatggca accgctacta tttcgaaccg aataccgcaa tgggtgcaaa tggctacaaa    1440
accatcgata ataaaaattt ctattttcgc aacggtctgc cgcagatcgg ggtatttaaa    1500
ggtagcaacg gcttcgaata cttcgctcca gcgaatacgg acgcgaacaa tattgagggt    1560
caagcgattc gttatcaaaa ccgttttctg catctgctgg gcaaaatcta ctactttggc    1620
aataacagta aagcagttac tggatggcag acaatcaatg gtaaagtgta ctattttatg    1680
ccggataccg ccatggcagc agccggtggt ctgtttgaaa ttgatggcgt gatctatttt    1740
tttggtgtgg atggtgttaa agcagtgagc ggtctgattt atattaacga tagcctgtat    1800
tactttaaac caccggtgaa taacctgatt accggctttg tgaccgtggg tgatgataaa    1860
tactatttca atccgattaa cggtggtgca gcgagcattg gcgaaaccat catcgatgac    1920
aaaaactatt atttcaacca gagcggtgtg ctgcagaccg gtgtgtttag caccgaagat    1980
ggctttaaat attttgcgcc agcgaacacc ctggatgaaa acctggaagg cgaagcgatt    2040
gattttaccg gcaaactgat catcgatgaa aacatctatt acttcgatga taactatcgt    2100
ggtgcggtgg aatggaaaga actggatggc gaaatgcatt atttttctcc ggaaaccggt    2160 aaagcgtttta aaggcctgaa ccagatcggc gattacaaat actacttcaa cagcgatggc    2220
gtgatgcaga aaggctttgt gagcatcaac gataacaaac actatttcga tgatagcggt    2280
gtgatgaaag tgggctatac cgaaattgat ggcaaacatt tctacttcgc ggaaaacggc    2340
gaaatgcaga ttggcgtgtt caataccgaa gatggtttca atacttcgc gcaccataac    2400 gaagatctgg gtaacgaaga aggcgaagaa attagctata gcggcatcct gaacttcaac    2460
aacaaaatct actactttga tgatagcttt accgcggtgg tgggctggaa agatctggaa    2520
gatggcagca aatattattt cgatgaagat accgcggaag cgtatattgg cctgagcctg    2580
attaacgatg gccagtacta ttttaacgat gatggcatta tgcaggtggg tttcgtgacc    2640
attaatgata aagtgttcta tttcagcgat agcggcatta ttgaaagcgg cgtgcagaac    2700
attgatgata ctacttcta catcgatgat aacggcattg tgcagatcgg cgttttttgat    2760 accagcgatg gctacaaata tttcgcaccg gccaataccg tgaacgataa catttatggc    2820
caggcggtgg aatatagcgg tctggtgcgt gtgggcgaag atgtgtatta tttcggcgaa    2880
acctatacca tcgaaaccgg ctggatttat gatatgaaa acgaaagcga taaatattac    2940
tttaatccgg aaacgaaaaa agcgtgcaaa ggcattaacc tgatcgatga tatcaaatac    3000
tattttgatg aaaaaggcat tatgcgtacc ggtctgatta gcttcgaaaa caacaactat    3060
tacttcaacg aaaacggtga atgcagttc ggctacatca acatcgaaga taaaatgttc    3120
tacttcggcg aagatggtgt tatgcagatt ggtgtttttta acaccccgga tggcttcaaa    3180
tactttgccc atcagaatac cctggatgaa aattttcgaag gtgaaagcat taactatacc    3240
ggctggctgg atctggatga aaaacgctac tacttcaccg atgaatacat tgcggcgacc    3300
ggcagcgtga ttattgatgg cgaagaatac tacttcgatc cggataccgc gcagctggtg    3360
attagcgaac atcatcatca tcaccat                                        3387

<210> SEQ ID NO 15
<211> LENGTH: 1129
<212> TYPE: PRT
```

<213> ORGANISM: Clostridium Difficile

<400> SEQUENCE: 15

```
Met Ala Thr Gly Trp Gln Thr Ile Asp Gly Lys Lys Tyr Tyr Phe Asn
1               5                   10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45

Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400
```

Gly Ile Met Gln Ile Gly Val Phe Lys Gly Pro Asp Gly Phe Glu Tyr
            405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
            435                 440                 445

Gly Asn Asn Ser Lys Ala Ala Thr Gly Trp Val Thr Ile Asp Gly Asn
450                 455                 460

Arg Tyr Tyr Phe Glu Pro Asn Thr Ala Met Ala Asn Gly Tyr Lys
465                 470                 475                 480

Thr Ile Asp Asn Lys Asn Phe Tyr Phe Arg Asn Gly Leu Pro Gln Ile
            485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
            515                 520                 525

Phe Leu His Leu Leu Gly Lys Ile Tyr Tyr Phe Gly Asn Asn Ser Lys
            530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
            565                 570                 575

Val Ile Tyr Phe Phe Gly Val Asp Gly Val Lys Ala Val Ser Gly Leu
            580                 585                 590

Ile Tyr Ile Asn Asp Ser Leu Tyr Tyr Phe Lys Pro Pro Val Asn Asn
            595                 600                 605

Leu Ile Thr Gly Phe Val Thr Val Gly Asp Asp Lys Tyr Tyr Phe Asn
            610                 615                 620

Pro Ile Asn Gly Gly Ala Ala Ser Ile Gly Glu Thr Ile Ile Asp Asp
625                 630                 635                 640

Lys Asn Tyr Tyr Phe Asn Gln Ser Gly Val Leu Gln Thr Gly Val Phe
            645                 650                 655

Ser Thr Glu Asp Gly Phe Lys Tyr Phe Ala Pro Ala Asn Thr Leu Asp
            660                 665                 670

Glu Asn Leu Glu Gly Glu Ala Ile Asp Phe Thr Gly Lys Leu Ile Ile
            675                 680                 685

Asp Glu Asn Ile Tyr Tyr Phe Asp Asp Asn Tyr Arg Gly Ala Val Glu
            690                 695                 700

Trp Lys Glu Leu Asp Gly Glu Met His Tyr Phe Ser Pro Glu Thr Gly
705                 710                 715                 720

Lys Ala Phe Lys Gly Leu Asn Gln Ile Gly Asp Tyr Lys Tyr Tyr Phe
            725                 730                 735

Asn Ser Asp Gly Val Met Gln Lys Gly Phe Val Ser Ile Asn Asp Asn
            740                 745                 750

Lys His Tyr Phe Asp Asp Ser Gly Val Met Lys Val Gly Tyr Thr Glu
            755                 760                 765

Ile Asp Gly Lys His Phe Tyr Phe Ala Glu Asn Gly Glu Met Gln Ile
            770                 775                 780

Gly Val Phe Asn Thr Glu Asp Gly Phe Lys Tyr Phe Ala His His Asn
785                 790                 795                 800

Glu Asp Leu Gly Asn Glu Glu Gly Glu Glu Ile Ser Tyr Ser Gly Ile
            805                 810                 815

Leu Asn Phe Asn Asn Lys Ile Tyr Tyr Phe Asp Asp Ser Phe Thr Ala

```
                820                 825                 830
Val Val Gly Trp Lys Asp Leu Glu Asp Gly Ser Lys Tyr Tyr Phe Asp
            835                 840                 845

Glu Asp Thr Ala Glu Ala Tyr Ile Gly Leu Ser Leu Ile Asn Asp Gly
            850                 855                 860

Gln Tyr Tyr Phe Asn Asp Asp Gly Ile Met Gln Val Gly Phe Val Thr
865                 870                 875                 880

Ile Asn Asp Lys Val Phe Tyr Phe Ser Asp Ser Gly Ile Ile Glu Ser
                885                 890                 895

Gly Val Gln Asn Ile Asp Asp Asn Tyr Phe Tyr Ile Asp Asp Asn Gly
            900                 905                 910

Ile Val Gln Ile Gly Val Phe Asp Thr Ser Asp Gly Tyr Lys Tyr Phe
            915                 920                 925

Ala Pro Ala Asn Thr Val Asn Asp Asn Ile Tyr Gly Gln Ala Val Glu
            930                 935                 940

Tyr Ser Gly Leu Val Arg Val Gly Glu Asp Val Tyr Tyr Phe Gly Glu
945                 950                 955                 960

Thr Tyr Thr Ile Glu Thr Gly Trp Ile Tyr Asp Met Glu Asn Glu Ser
                965                 970                 975

Asp Lys Tyr Tyr Phe Asn Pro Glu Thr Lys Lys Ala Cys Lys Gly Ile
            980                 985                 990

Asn Leu Ile Asp Asp Ile Lys Tyr Tyr Phe Asp Glu Lys Gly Ile Met
            995                 1000                1005

Arg Thr Gly Leu Ile Ser Phe Glu Asn Asn Asn Tyr Tyr Phe Asn Glu
            1010                1015                1020

Asn Gly Glu Met Gln Phe Gly Tyr Ile Asn Ile Glu Asp Lys Met Phe
1025                1030                1035                1040

Tyr Phe Gly Glu Asp Gly Val Met Gln Ile Gly Val Phe Asn Thr Pro
            1045                1050                1055

Asp Gly Phe Lys Tyr Phe Ala His Gln Asn Thr Leu Asp Glu Asn Phe
            1060                1065                1070

Glu Gly Glu Ser Ile Asn Tyr Thr Gly Trp Leu Asp Leu Asp Glu Lys
            1075                1080                1085

Arg Tyr Tyr Phe Thr Asp Glu Tyr Ile Ala Ala Thr Gly Ser Val Ile
            1090                1095                1100

Ile Asp Gly Glu Glu Tyr Tyr Phe Asp Pro Asp Thr Ala Gln Leu Val
1105                1110                1115                1120

Ile Ser Glu His His His His His His
                1125

<210> SEQ ID NO 16
<211> LENGTH: 2985
<212> TYPE: DNA
<213> ORGANISM: Clostridium Difficile

<400> SEQUENCE: 16
atggcaaccg gttggcagac catcgatggc aaaaaatatt attttaatac caacaccgca    60
attgcaagca ccggctatac cattatcaac ggcaaacact tttattttaa caccgacggc   120
attatgcaga ttggtgtgtt taaaggtccg aacggctttg aatactttgc accggcaaat   180
accgatgcca ataatattga aggccaggcc attctgtatc agaatgaatt tctgaccctg   240
aacggcaaaa atactacttt ggcagcgat agcaaagcag ttaccggttg cgcatcatc    300 aacaataaga aatattactt caacccgaat aatgcaattg cagcaattca tctgtgcacc   360
```

```
attaacaacg acaaatatta tttcagctat gacggtattc tgcagaatgg ctacattacc    420
atcgaacgca acaacttta tttcgatgcc aacaacgaaa gcaaaatggt gaccggtgtt    480
ttcaaaggcc ctaatggttt tgagtatttc gctccggcaa acacccataa taacaacatt    540
gaaggtcagg cgatcgttta tcagaacaaa ttcctgacgc tgaatggtaa gaaatactat    600
ttcgataatg acagcaaagc cgtgaccggc tggcagacaa ttgacgggaa gaaatattac    660
tttaatctga ataccgcaga agcagcaacc ggttggcaaa cgatcgacgg taaaaagtac    720
tacttcaacc tgaacacagc cgaagcagcc acaggatggc agactattga tggaaaaaaa    780
tactatttca acaccaacac ctttattgca tctaccggtt ataccagcat taacggtaaa    840
catttctact tcaacaccga tggtatcatg cagatcggcg ttttcaaagg tccaaatggt    900
ttcgaatact tgcccctgc caatacagat gcaaataaca tcgagggtca ggcaatcctg    960
taccaaaaca aatttctgac cctgaatggg aaaaatatt actttggtag cgattctaaa   1020
gccgttaccg tctgcgtac cattgatggt aaaaaatact actttaatac gaatacagcc   1080
gttgcggtta caggctggca gaccattaac gggaaaaaat actatttaa cacaaatacc   1140 agcattgcct caacgggtta taccattatt tcgggtaaac acttctactt taataccgat   1200
ggtattatgc aaatcggagt cttaaagga cctgatgggt tcgaatattt tgcgcctgcg   1260
aacactgatg cgaacaatat cgaaggacag gcaatccgct atcagaatcg ctttctgtat   1320
ctgcacgaca acatctatta ttttggcaac aattcaaaag cagccaccgg ctgggttaca   1380
attgatggca accgctacta tttcgaaccg aataccgcaa tgggtgcaaa tggctacaaa   1440
accatcgata ataaaaattt ctattttcgc aacggtctgc cgcagatcgg ggtatttaaa   1500
ggtagcaacg gcttcgaata cttcgctcca gcgaatacgg acgcgaacaa tattgagggt   1560
caagcgattc gttatcaaaa ccgttttctg catctgctgg gcaaaatcta ctactttggc   1620
aataacagta aagcagttac tggatggcag acaatcaatg gtaaagtgta ctattttatg   1680
ccggataccg ccatggcagc agccggtggt ctgtttgaaa ttgatggcgt gatctatttt   1740
tttggtgtgg atggtgttaa agcagtgaaa ggcctgaacc agatcggcga ttacaaatac   1800
tacttcaaca gcgatggcgt gatgcagaaa ggctttgtga gcatcaacga taacaaacac   1860
tatttcgatg atagcggtgt gatgaaagtg ggctataccg aaattgatgg caaacatttc   1920
tacttcgcgg aaaacggcga aatgcagatt ggcgtgttca ataccgaaga tggtttcaaa   1980
tacttcgcgc accataacga agatctgggt aacgaagaag gcgaagaaat tagctatagc   2040
ggcatcctga acttcaacaa caaaatctac tactttgatg atagctttac cgcggtggtg   2100
ggctggaaag atctggaaga tggcagcaaa tattatttcg atgaagatac cgcggaagcg   2160
tatattggcc tgagcctgat taacgatggc cagtactatt ttaacgatga tggcattatg   2220
caggtgggtt tcgtgaccat taatgataaa gtgttctatt tcagcgatag cggcattatt   2280
gaaagcggcg tgcagaacat tgatgataac tacttctaca tcgatgataa cggcattgtg   2340
cagatcggcg tttttgatac cagcgatggc tacaaatatt tcgcaccggc caataccgtg   2400
aacgataaca tttatggcca ggcggtggaa tatagcggtc tggtgcgtgt gggcgaagat   2460
gtgtattatt tcggcgaaac ctataccatc gaaccggct ggatttatga tatggaaaac   2520
gaaagcgata atatactt taatccggaa acgaaaaaag cgtgcaaagg cattaacctg   2580
atcgatgata tcaaatacta ttttgatgaa aaaggcatta tgcgtaccgg tctgattagc   2640
ttcgaaaaca caactatta cttcaacgaa acggtgaaa tgcagttcgg ctacatcaac   2700
atcgaagata aaatgttcta cttcggcgaa gatggtgtta tgcagattgg tgttttaac   2760
```

```
acccggatg gcttcaaata ctttgcccat cagaataccc tggatgaaaa tttcgaaggt    2820
gaaagcatta actataccgg ctggctggat ctggatgaaa aacgctacta cttcaccgat    2880
gaatacattg cggcgaccgg cagcgtgatt attgatggcg aagaatacta cttcgatccg    2940
gataccgcgc agctggtgat tagcgaacat catcatcatc accat                    2985

<210> SEQ ID NO 17
<211> LENGTH: 995
<212> TYPE: PRT
<213> ORGANISM: Clostridium Difficile

<400> SEQUENCE: 17

Met Ala Thr Gly Trp Gln Thr Ile Asp Gly Lys Lys Tyr Tyr Phe Asn
1               5                   10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45

Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335
```

```
Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
            355                 360                 365

Ile Asn Gly Lys Lys Tyr Tyr Phe Asn Thr Asn Thr Ser Ile Ala Ser
370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
                420                 425                 430

Arg Tyr Gln Asn Arg Phe Leu Tyr Leu His Asp Asn Ile Tyr Tyr Phe
                435                 440                 445

Gly Asn Asn Ser Lys Ala Ala Thr Gly Trp Val Thr Ile Asp Gly Asn
            450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
                500                 505                 510

Thr Asp Ala Asn Asn Ile Glu Gly Gln Ala Ile Arg Tyr Gln Asn Arg
            515                 520                 525

Phe Leu His Leu Leu Gly Lys Ile Tyr Tyr Phe Gly Asn Asn Ser Lys
            530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
                565                 570                 575

Val Ile Tyr Phe Phe Gly Val Asp Gly Val Lys Ala Val Lys Gly Leu
                580                 585                 590

Asn Gln Ile Gly Asp Tyr Lys Tyr Tyr Phe Asn Ser Asp Gly Val Met
            595                 600                 605

Gln Lys Gly Phe Val Ser Ile Asn Asp Asn Lys His Tyr Phe Asp Asp
            610                 615                 620

Ser Gly Val Met Lys Val Gly Tyr Thr Glu Ile Asp Gly Lys His Phe
625                 630                 635                 640

Tyr Phe Ala Glu Asn Gly Glu Met Gln Ile Gly Val Phe Asn Thr Glu
                645                 650                 655

Asp Gly Phe Lys Tyr Phe Ala His His Asn Glu Asp Leu Gly Asn Glu
            660                 665                 670

Glu Gly Glu Glu Ile Ser Tyr Ser Gly Ile Leu Asn Phe Asn Asn Lys
            675                 680                 685

Ile Tyr Tyr Phe Asp Asp Ser Phe Thr Ala Val Val Gly Trp Lys Asp
            690                 695                 700

Leu Glu Asp Gly Ser Lys Tyr Tyr Phe Asp Glu Asp Thr Ala Glu Ala
705                 710                 715                 720

Tyr Ile Gly Leu Ser Leu Ile Asn Asp Gly Gln Tyr Tyr Phe Asn Asp
                725                 730                 735

Asp Gly Ile Met Gln Val Gly Phe Val Thr Ile Asn Asp Lys Val Phe
                740                 745                 750
```

-continued

```
Tyr Phe Ser Asp Ser Gly Ile Ile Glu Ser Gly Val Gln Asn Ile Asp
        755                 760                 765
Asp Asn Tyr Phe Tyr Ile Asp Asp Asn Gly Ile Val Gln Ile Gly Val
        770                 775                 780
Phe Asp Thr Ser Asp Gly Tyr Lys Tyr Phe Ala Pro Ala Asn Thr Val
785             790                 795                 800
Asn Asp Asn Ile Tyr Gly Gln Ala Val Glu Tyr Ser Gly Leu Val Arg
                805                 810                 815
Val Gly Glu Asp Val Tyr Tyr Phe Gly Glu Thr Tyr Thr Ile Glu Thr
            820                 825                 830
Gly Trp Ile Tyr Asp Met Glu Asn Glu Ser Asp Lys Tyr Tyr Phe Asn
        835                 840                 845
Pro Glu Thr Lys Lys Ala Cys Lys Gly Ile Asn Leu Ile Asp Asp Ile
        850                 855                 860
Lys Tyr Tyr Phe Asp Glu Lys Gly Ile Met Arg Thr Gly Leu Ile Ser
865             870                 875                 880
Phe Glu Asn Asn Asn Tyr Tyr Phe Asn Glu Asn Gly Glu Met Gln Phe
                885                 890                 895
Gly Tyr Ile Asn Ile Glu Asp Lys Met Phe Tyr Phe Gly Glu Asp Gly
                900                 905                 910
Val Met Gln Ile Gly Val Phe Asn Thr Pro Asp Gly Phe Lys Tyr Phe
            915                 920                 925
Ala His Gln Asn Thr Leu Asp Glu Asn Phe Glu Gly Glu Ser Ile Asn
        930                 935                 940
Tyr Thr Gly Trp Leu Asp Leu Asp Glu Lys Arg Tyr Tyr Phe Thr Asp
945             950                 955                 960
Glu Tyr Ile Ala Ala Thr Gly Ser Val Ile Ile Asp Gly Glu Glu Tyr
                965                 970                 975
Tyr Phe Asp Pro Asp Thr Ala Gln Leu Val Ile Ser Glu His His His
                980                 985                 990
His His His
        995
```

US 9,644,024 B2

NUCLEOTIDE SEQUENCES, VECTORS AND HOST CELLS

CROSS-REFERENCE TO RELATED APPLICATIONS

This application is a continuation application of Ser. No. 14/122,690 filed 27 Nov. 2013, allowed, which was filed pursuant to 35 U.S.C. §371 as a United States National Phase Application of International Application No. PCT/EP2012/059793 filed May 25, 2012, which claims priority to U.S. Provisional Patent Application No. 61/490,734 filed May 27, 2011 and to U.S. Provisional Patent Application No. 61/490,707 filed May 27, 2011 and to U.S. Provisional Patent Application No. 61/490,716 filed May 27, 2011, the entire contents of which are incorporated by reference herein for all purposes.

TECHNICAL FIELD

The present invention relates to antigens from *Clostridium difficile*. In particular the invention relates to recombinant polypeptides comprising fragments of toxin A and toxin B from *C. difficile*. The invention additionally relates to immunogenic compositions or vaccines comprising these polypeptides, and the use of the vaccines and immunogenic compositions of the invention in prophylaxis or therapy. The invention also relates to methods of immunising using the compositions of the invention, and the use of the compositions of the invention in the manufacture of a medicament.

BACKGROUND

*C. difficile* is the most important cause of nosocomial intestinal infections and is the major cause of pseudomembranous colitis in humans (Bartlett et al *Am. J. Clin. Nutr.* 11 suppl:2521-6 (1980)). The overall associated mortality rate for individuals infected with *C. difficile* was calculated to be 5.99% within 3 months of diagnosis, with higher mortality associated with advanced age, being 13.5% in patients over 80 years (karas et al *Journal of Infection* 561:1-9 (2010)). The current treatment for *C. difficile* infection is the administration of antibiotics (metronidazole and vancomycin), however there has been evidence of strains which are resistant to these antibiotics (Shah et al., Expert Rev. Anti Infect. Ther. 8(5), 555-564 (2010)). Accordingly there is a need for immunogenic compositions capable of inducing antibodies to, and/or a protective immune response to, *C. difficile*.

BRIEF SUMMARY

The enterotoxicity of *C. difficile* is primarily due to the action of two toxins, toxin A and toxin B. These are both potent cytotoxins (Lyerly et al Current Microbiology 21:29-32 (1990). The C-terminal domains of toxin A and toxin B comprise repeating units, for example the C-terminal domain of toxin A is made up of contiguous repeating units (Dove et al *Infect. Immun.* 58:480-499 (1990)), for this reason the C-terminal domain may be referred to as the 'repeating domain'. These repeat portions can be separated further into short repeats (SRs) and long repeats (LRs) as described in Ho et al (PNAS 102:18373-18378 (2005)).

The structure of a 127-aa fragment from the C terminus of the toxin A repeat domain has been determined (Ho et al PNAS 102:18373-18378 (2005)). This fragment formed a β-solenoid like fold, composed predominantly of β strands with a low proportion of a helices.

It has been demonstrated that fragments of toxin A, in particular fragments of the C-terminal domain, can lead to a protective immune response in hamsters (Lyerly et al Current Microbiology 21:29-32 (1990)), WO96/12802 and WO 000/61762.

There is known to be difficulty involved in designing fusion proteins which fold correctly during expression. The polypeptides of the present invention are fusion proteins in which the native β-solenoid like structure is maintained, and which are seen to provide an immune response against both toxin A and toxin B in mice.

In a first aspect of the invention there is provided a polypeptide comprising a first fragment and a second fragment, wherein
 (i) the first fragment is a toxin A repeating domain fragment;
 (ii) the second fragment is a toxin B repeating domain fragment;
 (iii) the first fragment comprises a first proximal end within a first repeat portion;
 (iv) the second fragment comprises a second proximal end within a second repeat portion;
and wherein the first fragment and the second fragment are adjacent to one another and wherein the first repeat portion and the second repeat portion have sequence similarity to one another.

In a second aspect of the invention there is provided a polynucleotide encoding the polypeptide of the invention.

In a third aspect of the invention there is provided a vector comprising the polynucleotide of the invention linked to an inducible promoter.

In a fourth aspect of the invention there is provided a host cell comprising the vector of the invention or the polynucleotide of the invention.

In a fifth aspect of the invention there is provided an immunogenic composition comprising the polypeptide of the invention and a pharmaceutically acceptable excipient.

In a sixth aspect of the invention there is provided a vaccine comprising the immunogenic composition of the invention and a pharmaceutically acceptable excipient.

In a seventh aspect of the invention there is provided a use of the immunogenic composition of the invention or the vaccine of the invention in the treatment or prevention of *C. difficile* disease.

In an eighth aspect of the invention there is provided a use of the immunogenic composition of the invention or the vaccine of the invention in the preparation of a medicament for the prevention or treatment of *C. difficile* disease.

In a ninth aspect of the invention there is provided a method of preventing or treating *C. difficile* disease comprising administering the immunogenic composition of the invention or the vaccine of the invention to a patient.

BRIEF DESCRIPTION OF THE DRAWINGS

FIG. 1A-FIG. 1Q—Sequence listings of polypeptides of the invention.
 FIG. 1A—Provides the amino acid sequence of toxin A.
 FIG. 1B—Provides the amino acid sequence of toxin B.
 FIG. 1C—Provides the amino acid sequence of 'Fusion 1' fusion protein (SEQ ID NO:3).
 FIG. 1D—Provides the amino acid sequence of 'Fusion 2' fusion protein (SEQ ID NO:4).
 FIG. 1E—Provides the amino acid sequence of 'Fusion 3' fusion protein (SEQ ID NO:5).

FIG. 1F—Provides the amino acid sequence of 'Fusion 4' fusion protein (SEQ ID NO:6).

FIG. 1G—Provides the amino acid sequence of 'Fusion 5' fusion protein (SEQ ID NO:7).

FIG. 1H—Provides the amino acid sequence of toxin A fragment (SEQ ID NO:8).

FIG. 1I—Provides the amino acid sequence of toxin B fragment (SEQ ID NO:9).

FIG. 1J—Provides the nucleotide sequence encoding 'F54 Gly' (SEQ ID NO:10).

FIG. 1K—Provides the amino acid sequence of 'F54 Gly' (SEQ ID NO:11).

FIG. 1L—Provides the nucleotide sequence encoding 'F54 New' (SEQ ID NO:12).

FIG. 1M—Provides the amino acid sequence of 'F54 New' (SEQ ID NO:13)

FIG. 1N—Provides the nucleotide sequence encoding the 'F5 Tox B' fusion protein (SEQ ID NO:14).

FIG. 1O—Provides the amino acid sequence of the 'F5 Tox B' fusion protein (SEQ ID NO:15).

FIG. 1P—Provides the nucleotide sequence encoding the 'F52 new' fusion protein (SEQ ID NO:16).

FIG. 1Q—Provides the amino acid sequence of the 'F52 new' fusion protein (SEQ ID NO:17).

FIG. 6—Pictorial representation of a junction between the second SR VIII of ToxA and the third SR I of ToxB used in Fusion 4.

FIG. 7—Pictorial representation of a junction comprising a glycine linker between the last residue of the ToxA protein sequence and the beginning of the fourth SRII of ToxB used in Fusion 5.

FIG. 10—Graph describing the near-UV spectrum of Fusions 2, 3, 4, and 5 measured using circular dichroism. The spectrum for fusion 2 is represented by a line with the points depicted as cross shapes, the spectrum for fusion 3 is represented by a line with the points depicted as circles, the spectrum for fusion 4 is represented by a line with the points depicted as triangles, and the spectrum for fusion 5 is represented by a line with the points depicted as small diamond shapes.

FIG. 11—Graph showing anti-ToxA immunogenicity in mice immunised with a fragment of the C-terminus of toxin A (aa 2387-2706), a fragment of the C-terminus of toxin B (aa 1750-2360), or fusions 1, 2, 3, 4 or 5.

FIG. 17—Graph describing the Near-UV spectrum of fusions F52New, F54Gly, F54New and F5ToxB measured using circular dichroism. The spectrum for F52New is represented by a line with the points depicted as double crosses, the spectrum for F54Gly is represented by a line with the points depicted as triangles, F54New is represented by a line with the points depicted as squares, and F5ToxB is represented by a line with the points depicted as cross shapes.

FIG. 18—Graph showing anti-ToxA ELISA results for mice immunised with the F2, F52New, F54Gly, G54New or F5ToxB fusions.

FIG. 19—Graph showing anti-ToxB ELISA results for mice immunised with the F2, F52New, F54Gly, F54New or F5ToxB fusions.

FIG. 20—Graph showing hemagglutination inhibition in mice immunised with the F2, F52New, F54Gly, F54New or F5ToxB fusions.

DETAILED DESCRIPTION

Polypeptides

Figure 2:
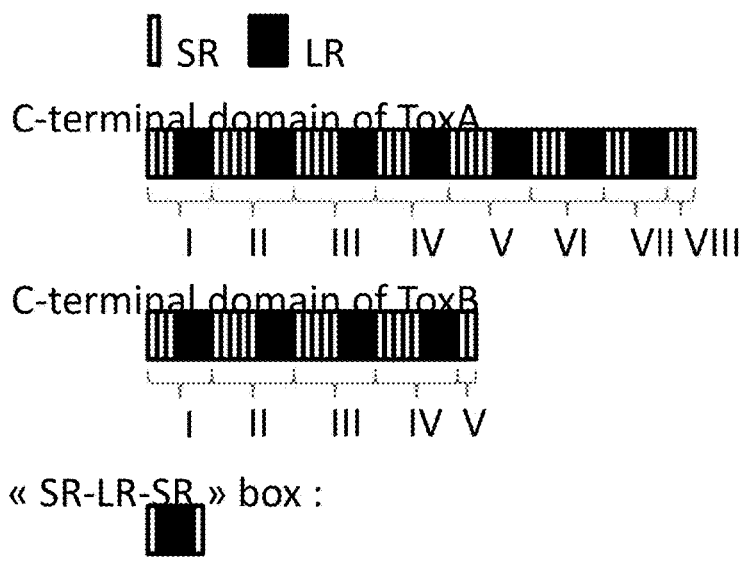
FIG. 2—Pictorial representation of the C-terminal domains of ToxA and ToxB, with the SR repeats depicted as white boxes and the LR boxes depicted as black boxes.

The invention relates to a polypeptide comprising a first fragment and a second fragment, wherein (i) the first fragment is a toxin A repeating domain fragment;

(ii) the second fragment is a toxin B repeating domain fragment;

(iii) the first fragment comprises a first proximal end within a first repeat portion;

(iv) the second fragment comprises a second proximal end within a second repeat portion; and wherein the first fragment and the second fragment are adjacent to one another and wherein the first repeat portion and the second repeat portion have sequence similarity to one another.

The term polypeptide refers to a contiguous sequence of amino acids.

The term 'toxin A repeating domain' refers to the C-terminal domain of the toxin A protein from *C. difficile*, comprising repeated sequences. This domain refers to amino acids 1832-2710 of toxin A from strain VP110463 (ATCC43255) and their equivalents in a different strain, the sequence of amino acids 1832-2710 from strain VP110463 (ATCC43255) corresponds to amino acids 1832-2710 of SEQ ID NO:1.

The term 'toxin B repeating domain' refers to the C-terminal domain of the toxin B protein from *C. difficile*. This domain refers to amino acids 1834-2366 from strain VP110463 (ATCC43255) and their equivalents in a different strain, the sequence of amino acids 1834-2366 from strain VP110463 (ATCC43255) corresponds to amino acids 1834-2366 of SEQ ID NO:2.

The *C. difficile* toxins A and B are conserved proteins, however the sequence differs a small amount between strains, moreover the amino acid sequence for toxins A and B in different strains may differ in number of amino acids.

The invention therefore contemplates the term toxin A repeating domain and/or toxin B repeating domain to refer to a sequence which is a variant with 90%, 95%, 98%, 99% or 100% sequence identity to amino acids 1832-2710 of SEQ ID NO:1 or a variant with 90%, 95%, 98%, 99% or 100% sequence identity to amino acids 1834-2366 of SEQ ID NO:2. In one embodiment a 'variant' is a polypeptide that varies from the referent polypeptides by conservative amino acid substitutions, whereby a residue is substituted by another with the same physico-chemical properties. Typically such substitutions are among Ala, Val, Leu and Ile; among Ser and Thr; among the acidic residues Asp and Glu; among Asn and Gln, and among the basic residues Lys and Arg; or aromatic residues Phe and Tyr. In one embodiment a 'fragment' is a polypeptide which comprises a contiguous portion of at least 250 amino acids of a polypeptide.

Furthermore the amino acid numbering may differ between the C-terminal domains of toxin A (or toxin B) from one strain and toxin A (or toxin B) from another strain. For this reason the term 'equivalents in a different strain' refers to amino acids which correspond those of a reference strain (e.g., *C. difficile* VP110463), but which are found in a toxin from a different strain and which may thus be numbered differently. A region of 'equivalent' amino acids may be determined by aligning the sequences of the toxins from the different strains. The amino acids numbers provided throughout refer to those of strain VP110463.

The term 'fragment' of a polypeptide or protein refers to a contiguous portion of at least 200, 230, 250, 300, 350, 380, 400, 450, 480, 500, 530, 550, 580 or 600 amino acids from that polypeptide or protein. The term 'first fragment' refers to a contiguous portion of at least 250, 300, 350, 380, 400, 450, 480, 500, 530, 550, 580 or 600 amino acids of the toxin A repeating domain. The term 'second fragment' refers to a contiguous portion of at least 200, 230, 250, 280, 300, 350, 400, 450 or 500 amino acids of the toxin B repeating domain.

The term 'first proximal end' refers to the end of the first fragment (Tox A fragment) which is covalently linked to the second fragment (ToxB fragment) or covalently linked to a linker sequence between the first and second fragment. The term 'second proximal end' refers to the end of the second fragment which is closest to the first fragment in primary structure (amino acid sequence).

FIG. 2 depicts the organisation of the C-terminal domains of ToxA and ToxB. The C-terminal domain of toxin A is made up of 8 repeat portions (designated repeat portion I, repeat portion II, repeat portion III, repeat portion IV, repeat portion V, repeat portion VI, repeat portion VII and repeat portion VIII) each of these repeat portions can be further divided into short repeats (SRs) which are depicted as white boxes in FIG. 2 and long repeats (LRs) which are depicted as black boxes in FIG. 2 (except for Tox A repeat portion VIII which does not have a long repeat). Each of the long repeats has some structural and sequence similarity to the other long repeats. Similarly the short repeats have some sequence and structural similarity to one another. Similarly the C-terminal domain of toxin B is made up of 5 repeat portions subdivided into SRs and LRs. Each repeat portion contains one LR and between 2 and 5 SRs (except for Tox B repeat portion V which does not have a long repeat). For the purposes of the disclosure the phrase 'a repeat portion' refers to one of the eight repeat portions of ToxA (designated I, II, III, IV, V, VI, VII and VIII.) or one of the five repeat portions of ToxB (designated I, II, III, IV or V As used herein the term 'first repeat portion' refers to a repeat portion (or partial repeat portion) from the toxin A repeating domain. The term 'second repeat portion' refers to a repeat portion (or partial repeat portion) from the toxin B repeating domain. For the purposes of the disclosure the term 'long repeat' refers to one of the LR domains depicted as black boxes in FIG. 2. For the purposes of the disclosure the term 'short repeat' refers to one of the SR domains depicted as white boxes in FIG. 2.

Thus for example, repeat portion I of ToxA contains three SRs and one LR, which can be referred to as the first SRI of ToxA, the second SRI of ToxA, the third SRI of ToxA and the LRI of ToxA, respectively.

The first proximal end is considered to be within a 'repeat portion' if the first fragment ends in an amino acid that is within that repeat portion (i.e., the first proximal end contains only part of the repeat portion sequence). Similarly the second proximal end is considered to be within a 'repeat portion' if the second fragment ends in an amino acid that is within that repeat portion. For example the first proximal end is within 'repeat portion I of ToxA if the first fragment ends with any one of amino acids 1832-1924 (inclusive) of VP110463 or their equivalent in another strain. The first proximal end is within a 'long repeat' or a 'short repeat' if the first fragment ends in an amino acid that is within a 'long repeat' or a 'short repeat', similarly the second proximal end is within a 'long repeat' or a 'short repeat' if the second fragment ends in an amino acid that is within a 'long repeat' or a 'short repeat'.

The amino acid positions of each domain has been defined for toxin A and toxin B from strain VP110463 (ATCC43255). These are as follows

TABLE 1

| Name | | Start position | End position |
|---|---|---|---|
| ToxA_I | SR1 | 1832 | 1852 |
| | SR2 | 1853 | 1873 |
| | SR3 | 1874 | 1893 |
| | LR | 1894 | 1924 |
| ToxA_II | SR1 | 1925 | 1944 |
| | SR2 | 1945 | 1965 |
| | SR3 | 1966 | 1986 |
| | SR4 | 1987 | 2007 |
| | SR5 | 2008 | 2027 |
| | LR | 2028 | 2058 |
| ToxA_III | SR1 | 2059 | 2078 |
| | SR2 | 2079 | 2099 |
| | SR3 | 2100 | 2120 |
| | SR4 | 2121 | 2141 |
| | SR5 | 2142 | 2161 |
| | LR | 2162 | 2192 |
| ToxA_IV | SR1 | 2193 | 2212 |
| | SR2 | 2213 | 2233 |
| | SR3 | 2234 | 2253 |
| | SR4 | 2254 | 2275 |
| | LR | 2276 | 2306 |
| ToxA_V | SR1 | 2307 | 2326 |
| | SR2 | 2327 | 2347 |
| | SR3 | 2348 | 2368 |
| | SR4 | 2369 | 2389 |
| | SR5 | 2390 | 2409 |
| | LR | 2410 | 2440 |
| ToxA_VI | SR1 | 2441 | 2460 |
| | SR2 | 2461 | 2481 |
| | SR3 | 2482 | 2502 |
| | SR4 | 2503 | 2522 |
| | LR | 2523 | 2553 |
| ToxA_VII | SR1 | 2554 | 2573 |
| | SR2 | 2574 | 2594 |
| | SR3 | 2595 | 2613 |
| | LR | 2614 | 2644 |
| ToxA_VIII | SR1 | 2645 | 2664 |
| | SR2 | 2665 | 2686 |
| | SR3 | 2687 | 2710 |
| ToxB_I | SR1 | 1834 | 1854 |
| | SR2 | 1855 | 1876 |
| | SR3 | 1877 | 1896 |
| | LR | 1897 | 1926 |
| ToxB_II | SR1 | 1927 | 1946 |
| | SR2 | 1947 | 1967 |
| | SR3 | 1968 | 1987 |
| | SR4 | 1988 | 2007 |
| | SR5 | 2008 | 2027 |
| | LR | 2028 | 2057 |
| ToxB_III | SR1 | 2058 | 2078 |
| | SR2 | 2079 | 2099 |
| | SR3 | 2100 | 2119 |
| | SR4 | 2120 | 2139 |
| | SR5 | 2140 | 2159 |
| | LR | 2160 | 2189 |
| ToxB_IV | SR1 | 2190 | 2212 |
| | SR2 | 2213 | 2233 |
| | SR3 | 2234 | 2253 |
| | SR4 | 2254 | 2273 |
| | SR5 | 2274 | 2293 |
| | LR | 2294 | 2323 |
| ToxB_V | SR1 | 2324 | 2343 |
| | SR2 | 2344 | 2366 |

For this reason the term 'repeat portion' may refer to amino acids 1832-1924, 1925-2058, 2059-2192, 2193-2306, 2307-2440, 2441-2553, 2554-2644 or 2645-2710 of toxin A (SEQ ID NO:1), or amino acids 1834-1926, 1927-2057, 2058-2189, 2190-2323 or 2324-2366 of toxin B (SEQ ID NO:2) or their equivalents in a different strain of C. difficile.

For this reason the term 'short repeat' may refer to amino acids 1832-1852, 1853-1873, 1874-1893, 1925-1944 1945-1965, 1966-1986, 1987-2007, 2008-2027, 2059-2078, 2079-2099, 2100-2120, 2121-2141, 2142-2161, 2193-2212, 2213-2233, 2234-2253, 2254-2275, 2307-2326, 2327-2347, 2348-2368, 2369-2389, 2390-2409, 2441-2460, 2461-2481, 2482-2502, 2503-2522, 2554-2573, 2574-2594, 2595-2613, 2645-2664, 2665-2686 or 2687-2710 of toxin A (SEQ ID NO:1) or amino acids 1834-1854, 1855-1876, 1877-1896, 1927-1946, 1947-1967, 1968-1987, 1988-2007, 2008-2027, 2058-2078, 2079-2099, 2100-2119, 2120-2139, 2140-2159, 2190-2212, 2213-2233, 2234-2253, 2254-2273, 2274-2293, 2324-2343 or 2344-2366 of toxin B (SEQ ID NO:2) or their equivalents in a different strain of C. difficile.

Similarly the term 'long repeat' may refer to amino acids 1894-1924, 2028-2058, 2162-2192, 2276-2306, 2410-2440, 2523-2553 or 2614-2644 of toxin A (SEQ ID NO:1) or amino acids 1897-1926, 2028-2057, 2160-2189 or 2294-2323 of toxin B (SEQ ID NO:2) or their equivalents in a different strain of C. difficile.

The polypeptides of the invention may be part of a larger protein such as a precursor or a fusion protein. It is often advantageous to include an additional amino acid sequence which contains sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

The word 'adjacent' means separated by less than or exactly 20, 15, 10, 8, 5, 2, 1 or 0 amino acids in the primary structure.

The fragments may be positioned such that the N-terminus of the first fragment is adjacent to the C-terminus of the second fragment, alternatively the C-terminus of the first fragment may be adjacent to the N-terminus of the second fragment, or the C-terminus of the first fragment may be adjacent to the C-terminus of the second fragment, or the N-terminus of the first fragment may be adjacent to the N-terminus of the second fragment.

Two sequences will have 'sequence similarity to one another' if they have greater than 50%, 70%, 75%, 80%, 85%, 90%, 95%, 98%, 99 or 100% sequence identity.

The term 'identity' is known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the Needle program BLASTP, BLASTN (Altschul, S. F. et al., J. Molec. Biol. 215: 403-410 (1990), and FASTA (Pearson and Lipman Proc. Natl. Acad. Sci. USA 85; 2444-2448 (1988). The BLAST family of programs is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

Parameters for polypeptide sequence comparison include the following:
Algorithm: Needleman and Wunsch, J. Mol Biol. 48: 443-453 (1970)
Comparison matrix: BLOSSUM62 from Henikoff and Henikoff, Proc. Natl. Acad. Sci. USA. 89:10915-10919 (1992)
Gap Penalty: 10
Gap extension penalty: 0.5

A program useful with these parameters is publicly available as the 'needle' program from EMBOSS package (Rice P et al, Trends in Genetics 2000 col. 16(6):276-277). The aforementioned parameters are the default parameters for peptide comparisons (along with no penalty for end gaps).

In one embodiment the first repeat portion and the second repeat portion have high structural similarity to one another. Two sequences can be considered to have high structural similarity when their percentage identity is higher than 40%, 45%, 50% or 60% (M. Marty-Renom et al. Annu. Rev. Biophys. Biomol Struct. 2000 vol. 29:291-325). The presence of high structural similarity can be determined by comparing the two sequences using the SwissModel and SwissPDB Viewer softwares.

In one embodiment the polypeptide of the invention elicits antibodies that neutralise toxin A or toxin B. In a further embodiment the polypeptide elicits antibodies that neutralise toxin A. In a further embodiment the polypeptide elicits antibodies that neutralise toxin B. In a further embodiment the polypeptide elicits antibodies that neutralise toxin A and toxin B. The phrase 'elicits neutralising antibodies' means that the when the compositions are used to immunise a mammal for example a mouse, a guinea pig or a human, the mammal generates neutralising antibodies.

Whether a polypeptide elicits neutralizing antibodies against a toxin can be measured by immunising mice with an immunogenic composition comprising the polypeptide, collecting sera and analysing the anti-toxin titres of the sera using by ELISA. The sera should be compared to a reference sample obtained from mice which have not been immunised. An example of this technique can be found in example 6. The polypeptide of the invention elicits antibodies that neutralise toxin A if the sera against the polypeptide gives an ELISA readout more than 10%, 20%, 30%, 50%, 70%, 80%, 90% or 100% higher than the reference sample.

In a further embodiment the polypeptide of the invention elicits a protective immune response in a mammalian host against strains of C. difficile. The phrase 'elicit a protective immune response' means that when the immunogenic composition of the invention is used to immunise a mammal such as a mouse, guinea pig or human, the mammal generates antibodies capable of protecting the mammal from death caused by C. difficile. In one embodiment the mammalian host is selected from the group consisting of mouse, rabbit, guinea pig, monkey, non-human primate or human. In one embodiment the mammalian host is a mouse. In a further embodiment the mammalian host is a human.

Whether a polypeptide elicits a protective immune response in a mammalian host against strains of C. difficile can be determined using a challenge assay. In such an assay the mammalian host is vaccinated with the polypeptide and challenged by exposure to C. difficile, the time which the mammal survives after challenge is compared with the time which a reference mammal that has not been immunised with the polypeptide survives. A polypeptide elicits a protective immune response if a mammal immunised with the polypeptide survives at least 10%, 20%, 30%, 50%, 70%, 80%, 90%, or 100% longer than a reference mammal which has not been immunised after challenge with C. difficile. In one embodiment the polypeptide of the invention elicits a protective immune response against strains of C. difficile in a mammal selected from the group consisting of mouse, guinea pig, monkey or human. In one embodiment the mammal is a mouse, in a further embodiment the mammal is a human.

The native structure of the C-terminal (repeat) domains from toxins A and B consist of an extended β solenoid-like structure. This structure consists of primarily β sheet structures, with a minority of a helical structures as seen in Ho et al (PNAS 102:18373-18378 (2005)). The secondary structures present can be determined using circular dichroism. For example measuring the shape and the magnitude of the CD spectra in the far-UV region (190-250 nm) and comparing the results with those of known structures. This can be carried out using an optical path of 0.01 cm from 178 to 250 nm, with a 1 nm resolution and bandwidth on a Jasco J-720 spectropolarimeter, for example as seen in example 5 below.

In one embodiment the first fragment comprises less than 28%, 25%, 23%, 20%, 18%, 15%, 10%, or 7% alpha helical secondary structure. In one embodiment the second fragment comprises less than 28%, 25%, 23%, 20%, 18%, 15%, 10%, or 7% alpha helical secondary structure. In a further embodiment both the first fragment and the second fragment comprise less than 28%, 25%, 23%, 20%, 18%, 15%, 10%, or 7% alpha helical secondary structure.

In one embodiment the first fragment comprises more than 20%, 25%, 28%, 30%, 33%, 35%, 38%, 40%, or 42% beta sheet structure. In one embodiment the second fragment comprises more than 20%, 25%, 28%, 30%, 33%, 35%, 38%, 40%, or 42% beta sheet structure. In a further embodiment both the first fragment and the second fragment comprises more than 20%, 25%, 28%, 30%, 33%, 35%, 38%, 40%, or 42% beta sheet structure.

In one embodiment the first proximal end is within repeat portion V (amino acids 2307-2440 of SEQ ID NO:1 or their equivalent in a different strain), VI (amino acids 2441-2553 of SEQ ID NO:1 or their equivalent in a different strain), VII (amino acids 2554-2644 of SEQ ID NO:1 or their equivalent in a different strain) or VIII (amino acids 2645-2710 of SEQ ID NO:1 or their equivalent in a different strain) of toxin A. In a further embodiment the first proximal end is within repeat portion VII (amino acids 2554-2644 of SEQ ID NO:1 or their equivalent in a different strain) of toxin A. In a further embodiment the first proximal end is within repeat portion VIII (amino acids 2645-2710 of SEQ ID NO:1 or their equivalent in a different strain) of toxin A.

In one embodiment the second proximal end is within repeat portion I (amino acids 1834-1926 of SEQ ID NO:2 or their equivalent in a different strain), II (amino acids 1927-2057 of SEQ ID NO:2 or their equivalent in a different strain), or III (amino acids 2058-2189 of SEQ ID NO:2 or their equivalent in a different strain) of toxin B. In a further embodiment the second proximal end is within repeat portion II (amino acids 1927-2057 of SEQ ID NO:2 or their equivalent in a different strain) of toxin B. In a further embodiment the second proximal end is within repeat portion I (amino acids 1834-1926 of SEQ ID NO:2 or their equivalent in a different strain) of toxin B.

In one embodiment the first proximal end is within a long repeat. The first proximal end may be within long repeat V of toxin A (amino acids 2410-2440 of SEQ ID NO:1 or their equivalent in a different strain), or within long repeat VI of toxin A (amino acids 2523-2553 of SEQ ID NO:1 or their equivalent in a different strain), or within long repeat VII of toxin A (amino acids 2614-2644 of SEQ ID NO:1 or their equivalent in a different strain).

In one embodiment the second proximal end is within a long repeat. The second proximal end may be within long repeat I of toxin B (amino acids 1897-1926 of SEQ ID NO:2 or their equivalent in a different strain), or within long repeat II of toxin B (amino acids 2028-2057 of SEQ ID NO:2 or their equivalent in a different strain), or within long repeat III of toxin B (amino acids 2160-2189 of SEQ ID NO:2 or their equivalent in a different strain).

In a further embodiment the first proximal end and the second proximal end are both within long repeats. In one embodiment the first proximal end is within long repeat V of toxin A (amino acids 2410-2440 of SEQ ID NO:1 or their equivalent in a different strain), or within long repeat VI of toxin A (amino acids 2523-2553 of SEQ ID NO:1 or their equivalent in a different strain), or within long repeat VII of toxin A (amino acids 2614-2644 of SEQ ID NO:1 or their equivalent in a different strain) and the second proximal end is within long repeatIof toxin B (amino acids 1897-1926 of SEQ ID NO:2 or their equivalent in a different strain), or within long repeat II of toxin B (amino acids 2028-2057 of SEQ ID NO:2 or their equivalent in a different strain), or within long repeat III of toxin B (amino acids 2160-2189 of SEQ ID NO:2 or their equivalent in a different strain). In one embodiment the first proximal end is within long repeat VII of toxin A (amino acids 2614-2644 of SEQ ID NO:1 or their equivalent in a different strain) and the second proximal end is within long repeat II of toxin B (amino acids 2028-2057 of SEQ ID NO:2 or their equivalent in a different strain).

In one embodiment the first proximal end is within amino acids 2620-2660 of toxin A. In one embodiment the second proximal end is within amino acids 2030-2050 of toxin B. In a further embodiment the first proximal end is within amino acids 2620-2660 of toxin A and the second proximal end is within amino acids 2030-2050 of toxin B.

In one embodiment the first fragment comprises at least 100, 150, 180, 200, 240, 250, 280, 300, 330, 350, 380, 400, 430, 450, 480, 500 or 530 amino acids. In one embodiment the second fragment comprises at least 100, 130, 150, 180, 200, 230, 250, 270, 300, 330, 350, 390, or 400 amino acids.

In one embodiment the polypeptide further comprises a linker. This linker may be between the first proximal end and the second proximal end, alternatively the linker may link the distal ends of the first fragment and/or the second fragment to a further sequence of amino acids.

A peptide linker sequence may be employed to separate the first fragment and second fragment. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first fragment and/or the second fragments; and (3) the lack of hydrophobic or charged residues that might react with the Tox A and/or ToxB functional epitopes. Peptide linker sequences may contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46 (1985); Murphy et al., Proc. Natl. Acad. Sci. USA 83:8258-8262 (1986); U.S. Pat. No. 4,935, 233 and U.S. Pat. No. 4,751,180. The linker sequence may generally be from 1 to about 50 amino acids in length.

In one embodiment the linker comprises between 1-20, 1-15, 1-10, 1-5, 1-2, 5-20, 5-15, 5-15, 10-20, or 10-15 amino acids. In one embodiment the linker is a glycine linker, the linker may comprise multiple contiguous glycine residues (1, 2, 3, 4, 5, 6, 7, 8, 9, 10, 11, 12, 13, 14, 15, 17, or 20), or alternatively the linker may comprise some glycine residues and some residues of other amino acids such as alanine. In a further embodiment the linker comprises a single glycine residue.

In an embodiment the polypeptide of the invention is part of a larger fusion protein. The fusion proteins may further comprise amino acids encoding an immunogenic portion of a further protein antigen. For example the fusion protein may further comprise an immunogenic portion of a protein antigen obtained or derived from a bacterium selected from the group consisting of *S. pneumoniae, H. influenzae, N. meningitidis, E. coli, M. cattarhalis, C. tentanii, C. diphtheriae, B. pertussis, S. epidermidis*, enterococci, *S. aureus*, and *Pseudomonas aeruginosa*. In this case the linker may be between the first fragment or the second fragment and a further immunogenic portion of a protein antigen.

The term "immunogenic portion thereof" or 'immunogenic fragment' refers to a fragment of a polypeptide wherein the fragment comprises an epitope that is recognized by cytotoxic T lymphocytes, helper T lymphocytes or B cells. Suitably, the immunogenic portion will comprise at least 30%, suitably at least 50%, especially at least 75% and in particular at least 90% (e.g. 95% or 98%) of the amino acids in the reference sequence. The immunogenic portion will suitably comprise all of the epitope regions of the reference sequence.

Polynucleotides

The invention further provides a polynucleotide encoding the polypeptide of the invention. For the purposes of the invention the term 'polynucleotide(s)' generally refers to any polyribonucleotide or polydeoxyribonucleotide, which may be unmodified RNA or DNA or modified RNA or DNA including single and double-stranded regions/forms.

The term "polynucleotide encoding a peptide" as used herein encompasses polynucleotides that include a sequence encoding a peptide or polypeptide of the invention. The term also encompasses polynucleotides that include a single continuous region or discontinuous regions encoding the peptide or polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native (i.e. naturally occurring) gene. Nonetheless, polynucleotides that vary due to differences in codon usage are specifically contemplated by the present invention, for example polynucleotides that are optimized for human and/or primate and/or *E. coli* codon selection.

Sequences encoding a desired polypeptide may be synthesized, in whole or in part, using chemical methods well known in the art (see Caruthers, M. H. et al., *Nucl. Acids Res. Symp. Ser.* pp. 215-223 (1980), Horn et al., *Nucl. Acids Res. Symp. Ser.* pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., Science 269:202-204 (1995)) and automated synthesis may be achieved, for example, using the ASI 431 A Peptide Synthesizer (Perkin Elmer, Palo Alto, Calif.).

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

Vectors

In a further aspect of the invention the present invention relates vector optionally comprising a polynucleotide of the invention linked to an inducible promoter such that when the promoter is induced a polypeptide encoded by the polynucleotide is expressed.

A further aspect of the invention comprises said vector wherein the inducible promoter is activated by addition of a sufficient quantity of IPTG (Isopropyl β-D-1-thiogalactopyranoside) to the growth medium. Optionally this is at a concentration of between 0.1 and 10 mM, 0.1 and 5 mM, 0.1 and 2.5 mM, 0.2 and 10 mM, 0.2 and 5 mM, 0.2 and 2.5 mM, 0.4 and 10 mM, 1 and 10 mM, 1 and 5 mM, 2.5 and 10 mM, 2.5 and 5 mM, 5 and 10 mM. Alternatively the promoter may be induced by a change in temperature or pH.

Host Cells

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, conjugation, transduction, scrape loading, ballistic introduction and infection.

Representative examples of appropriate hosts include gram negative bacterial cells, such as cells of, *E. coli, Acinetobacter, Actinobacillus, Bordetella, Brucella, Campylobacter, Cyanobacteria, Enterobacter, Erwinia, Franciscella, Helicobacter, hemophilus, Klebsiella, Legionella, Moraxella, Neisseria, Pasteurella, Proteus, Pseudomonas, Salmonella, Serratia, Shigella, Treponema, Vibrio, Yersinia*. In one embodiment the host cell is an *Escherichia coli* cell. Alternatively gram positive bacterial cells may also be used. A great variety of expression systems can be used to produce the polypeptides of the invention. In one embodiment the vector is derived from bacterial plasmids. Generally any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

Immunogenic Compositions and Vaccines

There is further provided an immunogenic composition comprising a polypeptide of the invention and a pharmaceutically acceptable excipient.

In one embodiment the immunogenic composition further comprises an adjuvant. The choice of a suitable adjuvant to be mixed with bacterial toxins or conjugates made using the processes of the invention is within the knowledge of the person skilled in the art. Suitable adjuvants include an aluminium salt such as aluminium hydroxide gel or aluminum phosphate or alum, but may also be other metal salts such as those of calcium, magnesium, iron or zinc, or may be an insoluble suspension of acylated tyrosine, or acylated sugars, cationically or anionically derivatized saccharides, or polyphosphazenes.

In one embodiment the immunogenic composition further comprises additional antigens. In one embodiment the additional antigens are antigens derived from a bacterium selected from the group consisting of *S. pneumoniae, H. influenzae, N. meningitidis, E. coli, M. cattarhalis*, tetanus, diphtheria, *pertussis, S. epidermidis*, enterococci, *S. aureus*, and *Pseudomonas aeruginosa*. In a further embodiment the immunogenic composition of the invention may comprise further antigens from *C. difficile* for example the S-layer proteins (WO01/73030). Optionally the immunogenic composition further comprises a saccharide from *C. difficile*.

There is further provide a vaccine comprising the immunogenic composition this vaccine may further comprise a pharmaceutically acceptable excipient. In a further aspect of the invention there is provided a vaccine comprising the immunogenic composition of the invention and an adjuvant.

The vaccine preparations containing immunogenic compositions of the present invention may be used to protect a mammal susceptible to *C. difficile* infection or treat a mammal with a *C. difficile* infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for coordination of the immune responses with respect to each other). In addition to a single route of administration, 2 different routes of administration may be used. For example, saccharides or saccharide conjugates may be administered intramuscularly (IM) or intradermally (ID) and bacterial proteins may be administered intranasally (IN) or intradermally (ID). In addition, the vaccines of the invention may be administered IM for priming doses and IN for booster doses.

The content of toxins in the vaccine will typically be in the range 1-250 µg, preferably 5-50 µg, most typically in the range 5-25 µg. Following an initial vaccination, subjects may receive one or several booster immunizations adequately spaced. Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

A further aspect of the invention is a method of preventing or treating C. difficile infection comprising administering to the host an immunoprotective dose of the immunogenic composition or vaccine or kit of the invention. In one embodiment there is provided a method of preventing or treating primary and/or recurrence episodes of C. difficile infection comprising administering to the host an immunoprotective dose of the immunogenic composition or vaccine or kit of the invention.

A further aspect of the invention is an immunogenic composition or vaccine or kit of the invention for use in the treatment or prevention of C. difficile disease. In one embodiment there is provided an immunogenic composition or vaccine or kit of the invention for use in the treatment or prevention of primary and/or recurrence episodes of C. difficile disease.

A further aspect of the invention is use of the immunogenic composition or vaccine or kit of the invention in the manufacture of a medicament for the treatment or prevention of C. difficile disease. In one embodiment there is provided an immunogenic composition or vaccine or kit of the invention for use in the manufacture of a medicament for the treatment or prevention of primary and/or recurrence episodes of C. difficile disease.

Around" or "approximately" are defined as within 10% more or less of the given figure for the purposes of the invention.

The terms "comprising", "comprise" and "comprises" herein are intended by the inventors to be optionally substitutable with the terms "consisting of", "consist of" and "consists of", respectively, in every instance. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

Embodiments herein relating to "vaccine compositions" of the invention are also applicable to embodiments relating to "immunogenic compositions" of the invention, and vice versa.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, may be approximate.

All references or patent applications cited within this patent specification are incorporated by reference herein in their entirety.

In order that this invention may be better understood, the following examples are set forth. These examples are for purposes of illustration only, and are not to be construed as limiting the scope of the invention in any manner.

EXAMPLES

Example 1

Design of Five C. Difficile ToxA-ToxB Fusions

Fusion proteins containing fragments of the C-terminal repeating domains of ToxA and ToxB were designed. These fusions contained a fragment of the C-terminal repeating domain of ToxA and a fragment of the C-terminal repeating domain of ToxB, and a junction between the C-terminal end of the ToxA fragment and the N terminal end of the ToxB fragment. Two strategies were devised, in the first strategy; the fusion was designed such that the long solenoid structure was maintained at the junction between the two fragments. In the second strategy, the two fragments of the fusions are separated by a linker to allow their independent correct folding.

The C-terminal part of ToxA and B is composed of repeated sequences: short repeats (SR) and long repeats (LR) (PNAS 2005 vol 102: 18373-18378).

The partial known 3D structure for the C-terminal domain of ToxA (PNAS 2005 Greco et al., vol 102: 18373-18378; Nature Structural & Molecular biology 2006 vol 13(5): 460-461; PDB codes: 2F6E, 2G7C and 2QJ6).

The inventors predicted that there are two kinds of important interactions between residues of the C-terminal part of ToxA and ToxB. The first interaction is occurring between residues contained in a LR and its preceding SR and is important to maintain the solenoid-like structure. The second type of interaction occurs between residues contained in a LR and the following SR and this interaction is mediating the carbohydrate-binding function of the toxin.

A new "structural-functional" repeat SR-LR-SR was defined. The structure of this repeat was maintained intact in our designed fusions.

FIG. 2 represents the C-terminal domains of ToxA and ToxB and the defined "SR-LR-SR" box.

The positions of the short (SR) and long repeats (LR) of ToxA and ToxB repeats are presented in table 1.

A list of the "SR-LR-SR" boxes contained in the C-terminal domain of ToxA and ToxB is presented in Table 2.

TABLE 2

| Name | Start position | End position |
| --- | --- | --- |
| ToxA_1 | 1874 | 1944 |
| ToxA_2 | 2008 | 2078 |

TABLE 2-continued

| Name | Start position | End position |
|---|---|---|
| ToxA_3 | 2142 | 2212 |
| ToxA_4 | 2254 | 2326 |
| ToxA_5 | 2390 | 2460 |
| ToxA_6 | 2503 | 2573 |
| ToxA_7 | 2595 | 2664 |
| ToxB_1 | 1877 | 1946 |
| ToxB_2 | 2008 | 2077 |
| ToxB_3 | 2140 | 2212 |
| ToxB_4 | 2274 | 2343 |

Finally, the number of SRs between two LRs will be maintained in the designed fusions to keep the long solenoid-like structure.

Before the design of junctions for the fusions, two working hypotheses were defined: first hypothesis, the shorter the fusions, the better the probability for the fusions to be stably over expressed; second hypothesis, according to the concept of "SR-LR-SR" boxes, the start position has to be chosen in order to ensure a correct folding of the first SR of this previously defined SR-LR-SR box. Thus the fusions start at the beginning of the SR that precedes the SR-LR-SR box. Using these two hypothesis, three start positions were analysed: residue 2370, 2234 and 2121 of ToxA.

The start position 2370 was excluded. The start position 2234 was also excluded because one of the residues involved in interactions important for the protein structural stability is not conserved. So, it was decided that all the designed fusion will begin at residue 2121 of ToxA.

All fusions will end at the last residue of ToxB.

Four fusions (F1-4) were designed in order to maintain the entire fusion in a long solenoid-like structure between the two fusion fragments.

Figure 3:
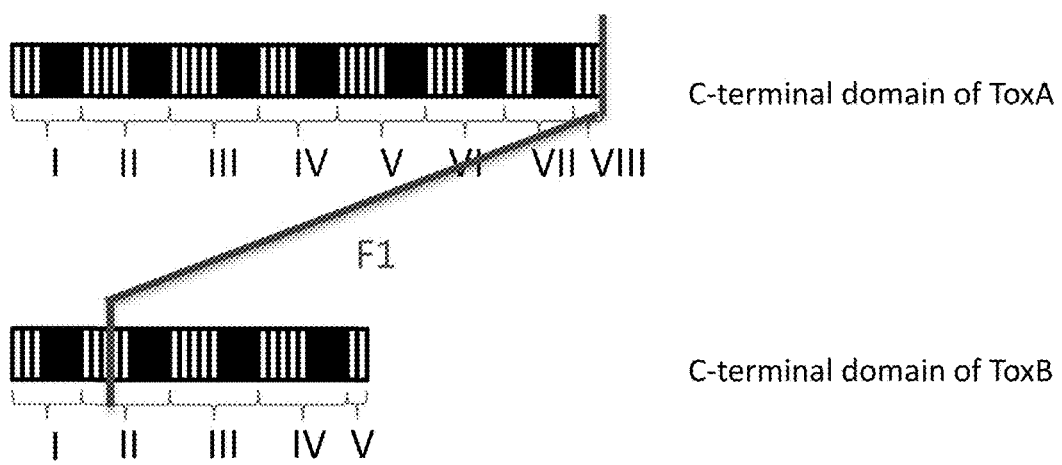
FIG. 3—Pictorial representation of a junction between the third SR VIII of ToxA and the fourth SR II of Tox B used in Fusion 1.
Figure 4:
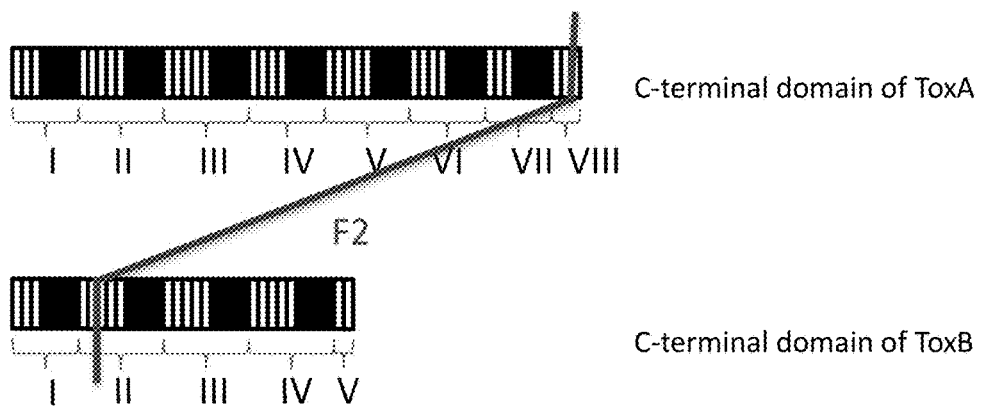
FIG. 4—Pictorial representation of a junction between the second SR VIII of ToxA and the third SR II of Tox B used in Fusion 2.

The fusions 1 (F1) and 2 (F2) were designed using the same hypothesis. All SR protein sequences of ToxA and ToxB had been compared using a multiple alignment software (ClustalW—Thompson J D et al. (1994) *Nucleic Acids Res.*, 22, 4673-4680). The more similar sequences were the third SR VIII of ToxA and the third SR II of ToxB and third SR III of ToxB. In order to make a choice between these two SR of ToxB, a structural homology modeling (using the SwissModel interface—Arnold K et al. (2006) *Bioinformatics*, 22, 195-201) was performed on the C-terminal part of ToxB using the known 3D structure of partial ToxA C-terminal domain (PDB code: 2QJ6). Using the third SR VIII of ToxA, the best local structural superposition (performed using SwissPDBViewer—Guex N et al. (1997), *Electrophoresis* 18, 2714-2723) was obtained with the third SR II of ToxB. So, two junctions were designed: the first one is between the third SR VIII of ToxA and the fourth SR II of ToxB (F1) and the second one is between the second SR VIII of ToxA and the third SR II of ToxB (F2). These junctions are presented in FIGS. 3 and 4 respectively.

Figure 5:
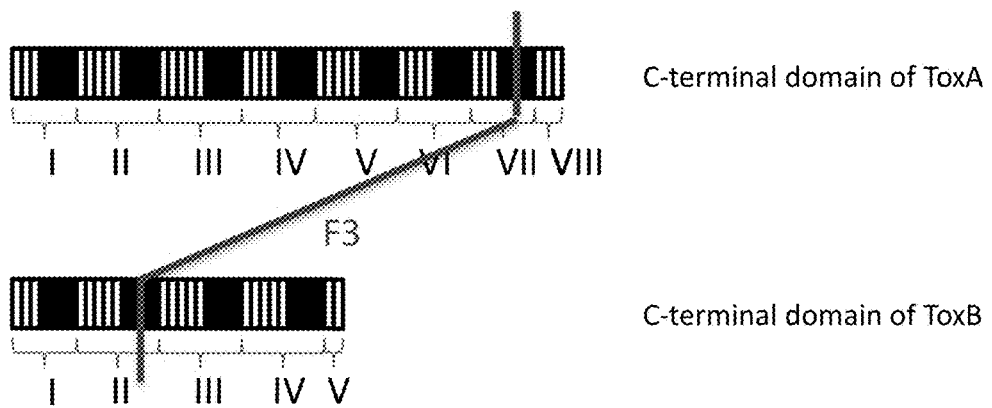
FIG. 5—Pictorial representation of a junction between LRVII of ToxA and LRII of ToxB used in Fusion 3 (containing only part of LRVII of ToxA and part of LR II of ToxB).
Figure 8A:
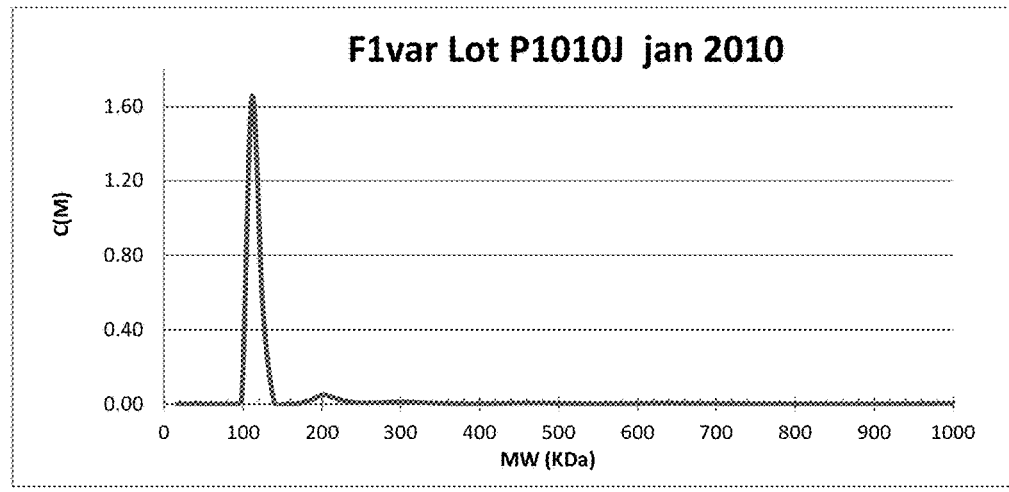
FIG. 8—Graphs describing the distribution of *C. difficile* ToxA-ToxB fusions 1-5 as determined by sedimentation velocity analytical ultracentrifugation. Panel a) describes the distribution of Fusion 1, panel b) describes the distribution of Fusion 2, panel c) describes the distribution of Fusion 3, panel d) describes the distribution of Fusion 4 and panel e) describes the distribution of Fusion 5.
Figure 8B:
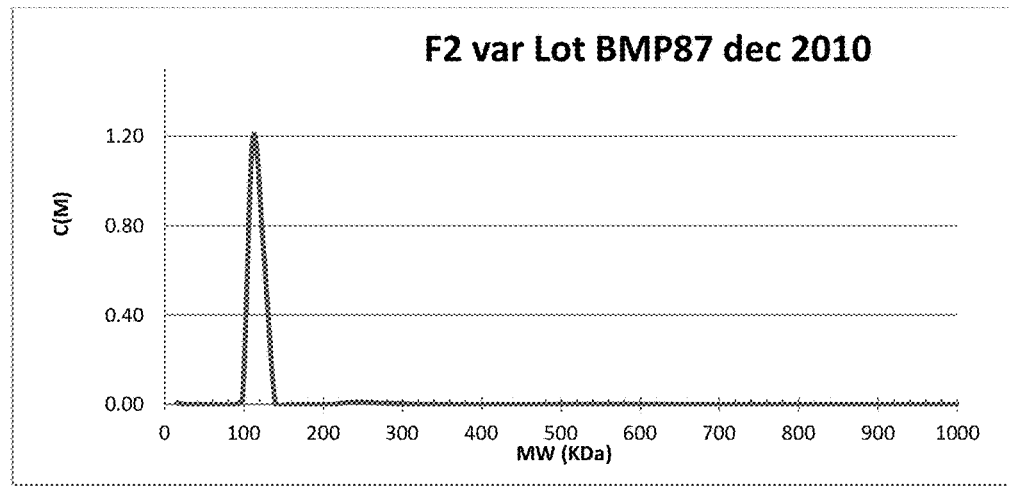
Figure 8C:
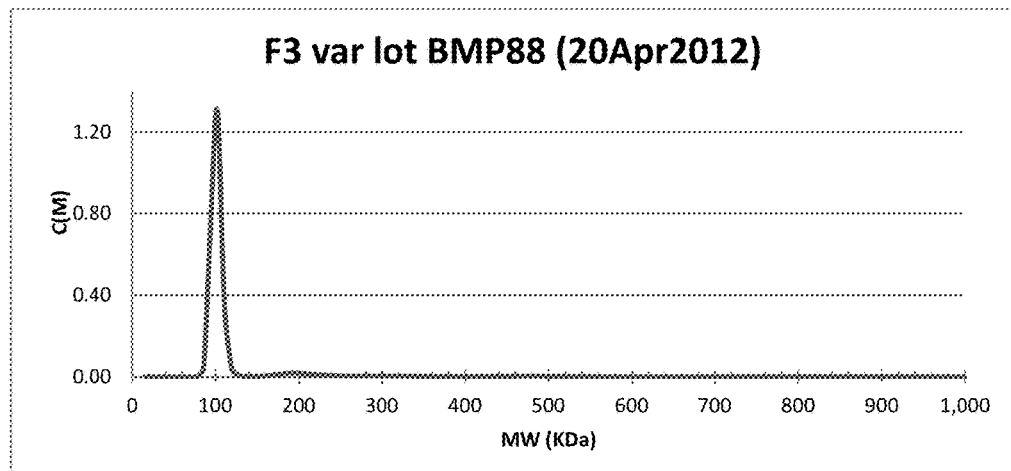
Figure 8D:
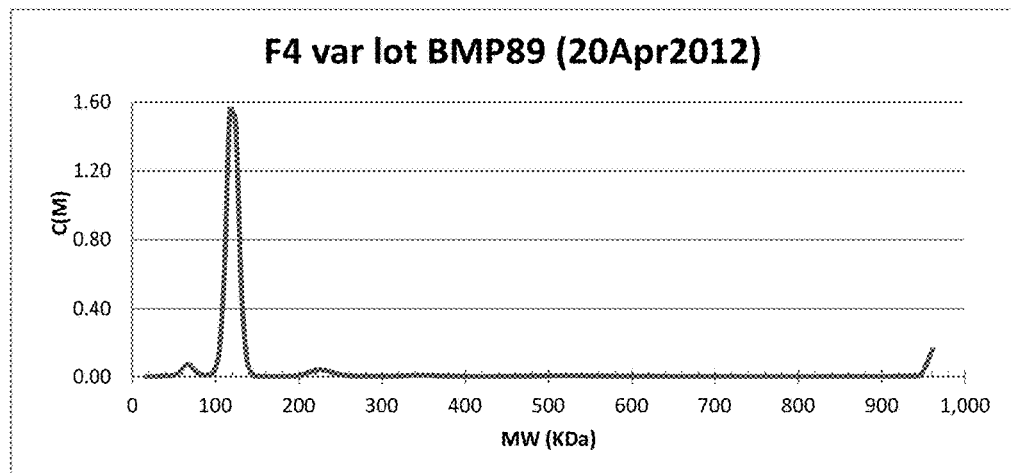
Figure 8E:
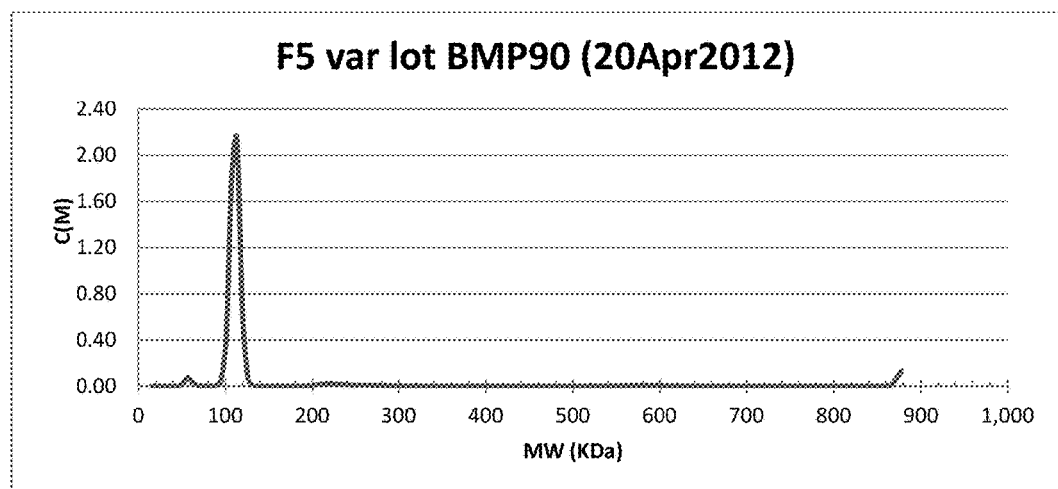

To design the fusion 3 (F3), a global structural superposition was performed between both the known structure of the partial C-terminal domain of ToxA and the predicted structure of C-terminal domain of ToxB (using SwissModel and SwissPDBViewer softwares). The best superposition was found between LR VII of ToxA and LR II of ToxB. So, it was decided to make a junction in this similar LR. The junction was performed firstly in a region where the sequence is conserved between ToxA and ToxB, after that in order to keep in the ToxA part of the fusion, the residues in interaction with the preceding SR and lastly, in order to keep in the ToxB part, the residues in interaction with the following SR. This junction is shown in FIG. 5.

For the design of fusion 4 (F4), the C-terminal domain of ToxB was divided in 4 fragments and a more precise homology modeling (SwissModel) was performed on them. The split was realised in order to keep intact the "SR-LR-SR" boxes (each domain finishes at the end of the SR that follows a LR). A structural superposition between the predicted structures of these fragment and the known 3D structure of ToxA was made and the best structural surperposition was obtained for the third SR of ToxB (SR I) and the last SR of ToxA (third SR VIII). So, the junction was done between the second SR VIII of ToxA and the third SRI of ToxB. This design is presented in FIG. 6.

The last fusion (F5) was designed in order to allow an independent correct folding of the two fragments of the fusion. The linker was added between the last residue of the ToxA protein sequence and the beginning of the fourth SR II of ToxB (always taking into account the importance of an intact "SR-LR-SR" box). Only one exogenous residue (Glycine) was added as linker and located between two existing Glycines. Thus, the linker can also be described as composed of 3 Glycines surrounding by known (for ToxA) and predicted (for ToxB) beta-strand. This last design is shown in FIG. 7.

Example 2

Cloning Expression and Purification of the Fusion Proteins

Expression Plasmid and Recombinant Strain

Genes encoding the fusion proteins of partial C-terminal domains of ToxA and ToxB (SEQ ID NO:3, 4, 5, 6 and 7) and a His tag were cloned into the pET24b(+) expression vector (Novagen) using the NdeI/XhoI restriction sites using standard procedures. The final construct was generated by the transformation of *E. coli* strain BLR (DE3) with the recombinant expression vector according to standard method with CaCl2-treated cells (Hanahan D. 'Plasmid transformation by Simanis.' In Glover, D. M. (Ed), DNA cloning. IRL Press London. (1985): p. 109-135.).

Host Strain:

BLR(DE3). BLR is a recA derivative of BL21. Strains having the designation (DE3) are lysogenic for a λ prophage that contains an IPTG inducible T7 RNA polymerase. λ DE3 lysogens are designed for protein expression from pET vectors This strain is also deficient in the lon and ompT proteases.

Genotype: *E. coli* BLR::DE3 strain, F⁻ ompT hsdS.$_B$($r_B^-$ $m_B^-$) gal dcm (DE3) Δ(srl-recA)306::Tn 10 (Tet$^R$)

Expression of the Recombinant Proteins:

An *E. coli* transformant was stripped from agar plate and used to inoculate 200 ml of LBT broth+1% (w/v) glucose+ kanamycin (50 μg/ml) to obtain O.D.600 nm between 0.1-0.2. Cultures were incubated overnight at 37° C., 250 RPM.

This overnight culture was diluted to 1:20 in 500 ml of LBT medium containing kanamycin (50 μg/ml) and grown at 37° C. at a stirring speed of 250 rpm until O.D.620 reached 0.5/0.6.

At O.D.600 around 0.6, the culture was cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After overnight induction (around 16 hours), O.D.·600 nm was evaluated after induction and culture was centrifuged at 14 000 RPM for 15 minutes and pellets were frozen at −20° C. separately.

Purification:

The bacterial pellet was resuspended in 20 mM bicine buffer (pH 8.0) containing 500 mM NaCl and a mixture of protease inhibitor (Complete, Roche). Bacteria were lysed using a French Press system 20 000 PSI. Soluble (supernatant) and insoluble (pellet) components were separated by centrifugation for example at 20 000 g for 30 min at 4° C.

The 6-His tagged-protein was purified under native conditions on IMAC. The soluble components were loaded on a GE column (15 ml for example) (Ni loaded) preequilibrated with the same buffer used to bacterial resuspension. After loading on the column, the column was washed with the same buffer. Elution was performed using a 20 mM bicine buffer (pH 8.0) containing 500 mM NaCl and different concentrations of imidazole (5-600 mM). After gel analysis, more pure fractions were selected, concentrated and loaded on SEC chromatography for further purification step.

Fractions containing the fusion proteins were selected on the basis of purity by SDS-PAGE and dialyzed against bicine buffer (20 mM Bicine, 150 mM NaCl, with or without 5 mM EDTA pH8.0), Protein concentration was determined using DC Protein Assay of BioRad. Proteins were thus pooled, sterile-filtered on 0.22 μm, stored at −80° C.

Alternatively, IMAC purification was preceded by a DEAE purification step using 2 mM bicine buffer (pH 8.0) for loading and washing, and eluted using a gradient with the same buffer but with 1 M NaCl added.

Example 3

Cloning Expression and Purification of the Separate *C. Difficile* Tox A and Tox B Fragments Expression Plasmid and Recombinant Strain.

Genes encoding the protein fragments of ToxA and ToxB (SEQ ID NO:8 and SEQ ID NO:9) and a His tag were cloned into the pET24b(+) expression vector (Novagen) using the NdeI/XhoI restriction sites using standard procedures. The final construct was generated by the transformation of *E. coli* strain BLR (DE3) with the recombinant expression vector according to standard method with CaCl2-treated cells (Hanahan D. 'Plasmid transformation by Simanis.' In Glover, D. M. (Ed), DNA cloning. IRL Press London. (1985): p. 109-135.).

Host Strain:

BLR(DE3). BLR is a recA derivative of BL21. Strains having the designation (DE3) are lysogenic for a λ prophage that contains an IPTG inducible T7 RNA polymerase. λ DE3 lysogens are designed for protein expression from pET vectors This strain is also deficient in the Ion and ompT proteases.

Genotype: *E. coli* BLR::DE3 strain, $F^-$ ompT hsd$S_B$ ($r_B^-$ $m_B^-$) gal dcm (DE3) Δ(srl-recA)306::Tn10 ($Tet^R$)

Expression of the Recombinant Proteins:

A *E. coli* transformant was stripped from agar plate and used to inoculate 200 ml of LBT broth+1% (w/v) glucose+ kanamycin (50 μg/ml) to obtain O.D.$_{600\ nm}$ between 0.1-0.2. Cultures were incubated overnight at 37° C., 250 RPM.

This overnight culture was diluted to 1:20 in 500 ml of LBT medium containing kanamycin (50 μg/ml) and grown at 37° C. at a stirring speed of 250 rpm until O.D.$_{620}$ reached 0.5/0.6.

At an O.D. at 600 nm of around 0.6, the culture was cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After the overnight induction (around 16 hours), O.D. at 600 nm was evaluated after induction and culture was centrifuged at 14 000 RPM for 15 minutes and pellets were frozen at −20° C. separately.

Purification:

The bacterial pellet was resuspended in 20 mM bicine buffer (pH 8.0) containing 500 mM NaCl supplemented by a mixture of protease inhibitor (Complete without EDTA, Roche cat 11873580001) and benzonase. (Roche cat 1.01695.0001). Bacteria were lysed using a French Press system 2×20 000 PSI. Soluble (supernatant) and insoluble (pellet) components were separated by centrifugation at 34 000 g or 48 000 g for 25-30 min at 4° C. Supernatant was harvested and filtrated on 0.22 μm filter.

The 6-His tagged-protein was purified under native conditions on IMAC. The soluble components were loaded on a GE column (for example 15 ml) (Ni loaded) pre-equilibrated with the same buffer used to bacterial resuspension. After loading, the column was washed with the same buffer.

For ToxA:

Elution was performed using a 20 mM bicine buffer (pH 8.0) containing 500 mM NaCl and different concentrations of imidazole (5-100 mM). After gel analysis, more pure fractions were selected, concentrated and loaded on SEC chromatography (SUPERDEX™ 75) for further purification step in the same buffer without imidazole.

For ToxB:

A second wash was performed with 20 mM bicine buffer (pH 8.0) containing 500 mM NaCl and 0.5% deoxycholate or same buffer with 150 mM NaCl. Elution was performed using a 20 mM bicine buffer (pH 8.0) containing 500 mM NaCl and different concentrations of imidazole (10-500 mM). After gel analysis, more pure fractions were selected, supplemented with 5 mM EDTA and loaded on SEC chromatography (SUPERDEX™ 200) for further purification step in same buffer with 5 mM EDTA.

Fractions containing ToxA or ToxB fragments were selected on the basis of purity by SDS-PAGE and dialyzed against bicine buffer (20 mM Bicine, 150 mM NaCl, pH8.0), protein concentration was determined using RCDC Protein Assay of BioRad. Proteins were thus pooled, sterile-filtered on 0.22 μm, stored at −80° C.

Example 4

Molecular Weight Evaluation of the Five *C. Difficile* ToxA-ToxB Fusions

Analytical ultracentrifugation is used to determine the homogeneity and size distribution in solution of the different species within a protein sample by measuring the rate at which molecules move in response to a centrifugal force. This is based on the calculation of the coefficients of sedimentation of the different species that are obtained by sedimentation velocity experiment, which depend on their molecular shape and mass.

1. Protein samples are spun in a Beckman-Coulter PROTEOMELAB™ XL-1 analytical ultracentrifuge at 42 000 RPM after the AN-0Ti rotor had been equilibrated to 15° C.
   a. F1 fusion protein, 500 μg/ml, 20 mM Bicine, 150 mM NaCl, pH8.0 b. F2 fusion protein, 500 µg/ml, 20 mM Bicine, 150 mM NaCl, pH8.0
c. F3 fusion protein, 500 µg/ml, 20 mM Bicine, 150 mM NaCl, pH8.0
d. F4 fusion protein, 500 µg/ml, 20 mM Bicine, 150 mM NaCl, pH8.0
e. F5 fusion protein, 500 µg/ml, 20 mM Bicine, 150 mM NaCl, pH8.0

2. For data collection, 160 scans were recorded at 280 nm every 5 minutes.
3. Data analysis was performed using the program SEDFIT for determination of the C(S) distribution. Determination of the partial specific volume of the proteins was performed with the SEDNTERP software from their amino acid sequence. SEDNTERP was also used to determine the viscosity and the density of the buffer.
4. The molecular weight of the different species was determined from the C(S) distribution plot (concentration vs sedimentation coefficient), considering that it's a better representation of the raw data than the C(M) distribution (concentration vs molecular weight) to characterize the size distribution of a mixture.

FIG. 8 describes the distribution of the ToxA-ToxB fusions as determined by sedimentation velocity analytical ultracentrifugation.

The molecular weight of the major species detected from the C(S) distribution of all five ToxA-ToxB fusion proteins corresponds to their monomeric form. The best fit frictional ratios determined for the five fusions are all between 2 and 2.2. This may indicate that the proteins are present in solution as an elongated form, which would be consistent with the protein structure.

Example 5

Evaluation of Secondary and Tertiary Structures of C. Difficile ToxA-ToxB Fusions by Circular Dichroism and Fluorescence Spectroscopy Circular dichroism is used to determine the secondary structure composition of a protein by measuring the difference in the absorption of left-handed polarized light versus right-handed polarized light which is due to structural asymmetry. The shape and the magnitude of the CD spectra in the far-UV region (190-250 nm) are different whether a protein exhibits a beta-sheet, alpha-helix or random coil structure. The relative abundance of each secondary structure type in a given protein sample can be calculated by comparison to reference spectra.

The tertiary structure of a protein sample can be assessed by the evaluation of the immobilisation of the aromatic amino acids. The observation of a CD signal in the near-UV region (250-50 nm) may be attributable to the polarization of phenylalanine, tyrosine and tryptophane residues and is a good indication that the protein is folded into a well defined structure.

The following protocol was used:
1. Far UV spectra are measured using an optical path of 0.01 cm from 178 to 250 nm, with a 1 nm resolution and bandwidth on a Jasco J-720 spectropolarimeter. Temperature of the cell is maintained at 23° C. by a Peltier thermostated RTE-111 cell block. A nitrogen flow of 10 L/min is maintained during the measurements.
2. Near-UV spectra are measured using an optical path of 0.01 cm from 250 to 300 nm, with a 1 nm resolution and bandwidth on a Jasco J-720 spectropolarimeter. Temperature of the cell is maintained at 23° C. by a Peltier thermostated RTE-111 cell block. A nitrogen flow of 6 L/min is maintained during the measurements.

Figure 9:
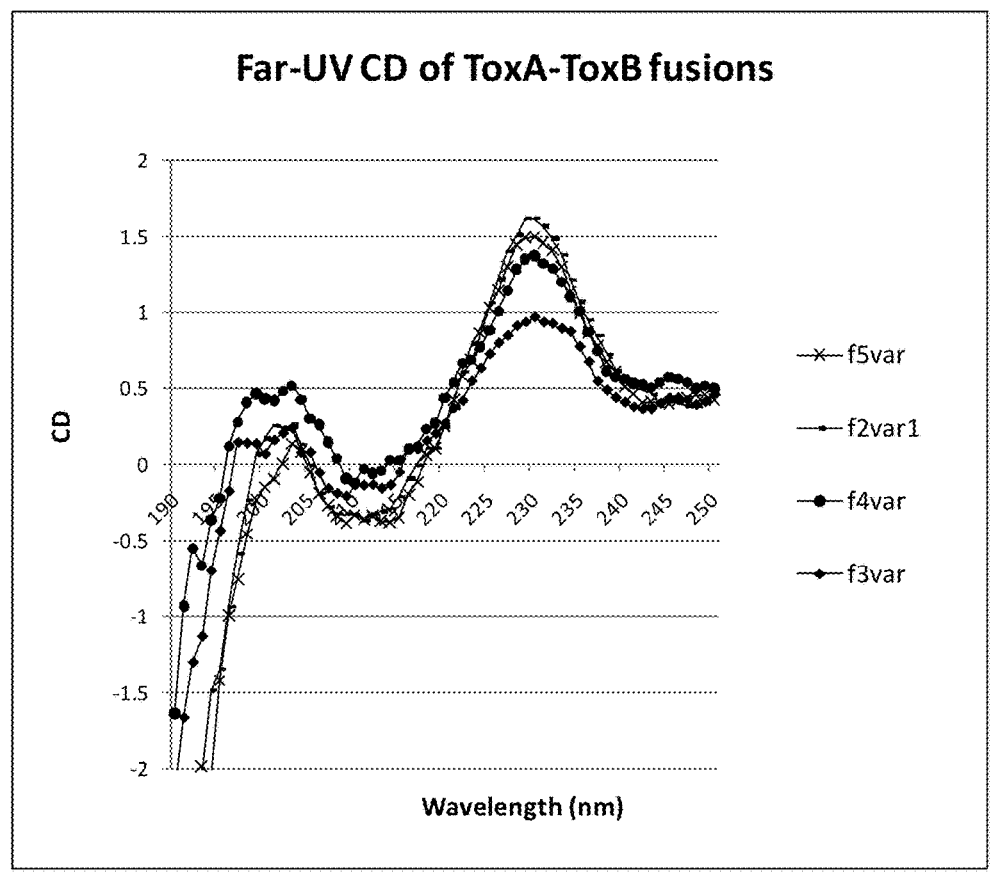
FIG. 9—Graph describing the Far-UV spectrum of Fusions, 2, 3, 4, and 5 measured using circular dichroism. The spectrum for fusion 2 is represented by a line with the points depicted as small squares, the spectrum for fusion 3 is represented by a line with the points depicted as small diamond shapes, fusion 4 is represented by a line with the points depicted as circles, and fusion 5 is represented by a line with the points depicted as cross shapes.

The observation of the far-UV spectra (FIG. 9) for all five ToxA-ToxB fusion proteins suggests a weak content of alpha helix structures and a high content of beta sheet structures. Also, all proteins exhibited a maximum at 230 nm, which is unusual for soluble globular proteins. This particularity has been well characterized in the literature and is associated with a small group of proteins known for their absence of alpha helix and their high content in beta sheet and aromatic amino acids (Zsila, Analytical Biochemistry, 391(2009) 154-156). Those particularities are coherent with the structure that is expected for the ToxA-ToxB fusion proteins. Crystal structures of 13 proteins exhibiting the characteristic CD spectra with a positive signal at 230 nm were compared (Protein Data Bank). The average secondary structure content of those proteins is 42% beta sheet+9% and 7% alpha helix+6%. This strongly indicates that the spectral signature of the ToxA-ToxB fusion proteins is diagnostic of a high beta sheet and low alpha helix containing protein.

The observation of the shape of the near-UV spectra (FIG. 10) for all five fusion proteins indicates that at least some of the aromatic amino acids are immobilised, which is a strong indication of a compact and specific tertiary structure. Moreover, the treatment of the protein with a denaturing concentration of urea caused the disappearance of the near-UV signal, which is an additional indication that this characteristic spectra was due to protein folding.

Example 6

Immunisation of Mice with Tox A or Tox B Fragments and ToxA-ToxB Fusions

Balb/C mice were immunized with the constructs described in examples 2 and 3.

Mice Immunization

Groups of 15 female Balb/c mice were immunized IM at days 0, 14 and 28 with 3 µg or 10 µg of the separate fragments of toxA and toxB (see example 2) as well as with ToxA-ToxB fusions proteins (see example 3) adjuvanted with ASO3B. A control group of 10 mice was vaccinated with ASO3B alone.

Anti-ToxA and anti-ToxB ELISA titers were determined in individual sera collected at day 42 (post III).

Hemagglutination inhibition titers were determined in pooled Post III sera.

Anti-ToxA and Anti-ToxB ELISA Response: Protocol

Samples of the toxA or toxB fragments were coated at 1 µg/ml in phosphate buffered saline (PBS) on high-binding microtitre plates (Nunc MAXISORP™), overnight at 4° C. The plates were blocked with PBS-BSA 1% for 30 min at RT with agitation. The mice anti-sera are prediluted 1/500 in PBS-BSA 0.2%-TWEEN™ 0.05%. and then, further two-fold dilutions were made in microplates and incubated at RT for 30 min with agitation. After washing, bound murine antibody was detected using Jackson ImmunoLaboratories Inc. peroxidase-conjugated affiniPure Goat Anti-Mouse IgG (H+L) (ref: 115-035-003) diluted 1:5000 in PBS-BSA 0.2%-tween 0.05%. The detection antibodies were incubated for 30 min. at room temperature (RT) with agitation. The color was developed using 4 mg O-phenylenediamine (OPD)+5 µl $H_2O_2$ per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-ToxA or anti-ToxB antibodies present in the sera was expressed in mid-point titers. A GMT was calculated for the 15 samples in each treatment group (10 for the control group).

Hemaqqlutination Inhibition Assay: Protocol

Serial twofold dilutions of mice pooled antisera (25 μl) were performed in phosphate buffered saline (PBS) in 96-well U-bottom microplates.

25 μl of native Toxin A (0.2 μg/well) were then added and the plates were incubated at room temperature for 30 minutes.

After incubation, 50 μl of purified rabbit erythrocytes diluted at 2% were added to each well. The plates were incubated at 37° C. for 2 hours.

Plates were analysed visually, with hemagglutination presenting as diffuse red cells in the well and the inhibition of hemagglutination observed as a red point settled in the well.

The inhibition titers were defined as the reciprocal of the highest dilution of the serum inhibiting hemagglutination.

Cytotoxicity Assay

IMR90 fibroblast cells were cultured at 37° C. with 5% $CO_2$, in EMEM+10% fetal bovine serum+1% glutamine+1% antibiotics (penicillin-streptomycin-amphotericin) and were seeded in 96-well tissue culture plates at a density of $5.10^4$ cells/well.

After 24 h, the cell media was removed from the wells.

Serial twofold dilutions of mice pooled antisera (50 μl) were performed in cell media.

50 μl of native Toxin B (0.5 ng/ml) is then added and the plates incubated at 37° C. with 5% CO2 for 24 hours.

Cells were observed after 24 hours, and the proportion of rounded cells was determined.

The inhibition titers were defined as the reciprocal of the highest dilution of the serum inhibiting 50% cell rounding.

Results:

Elisa results, using Tox A antibodies are described in FIG. 11. Anti-Tox A antibodies were induced after immunization with the ToxA alone but also with each of the 5 fusions.

The functional properties of these antibodies were tested in the hemagglutination assay. This assay is only adapted for Tox A evaluation as no hemagglutination is observed with ToxB.

Figure 12:
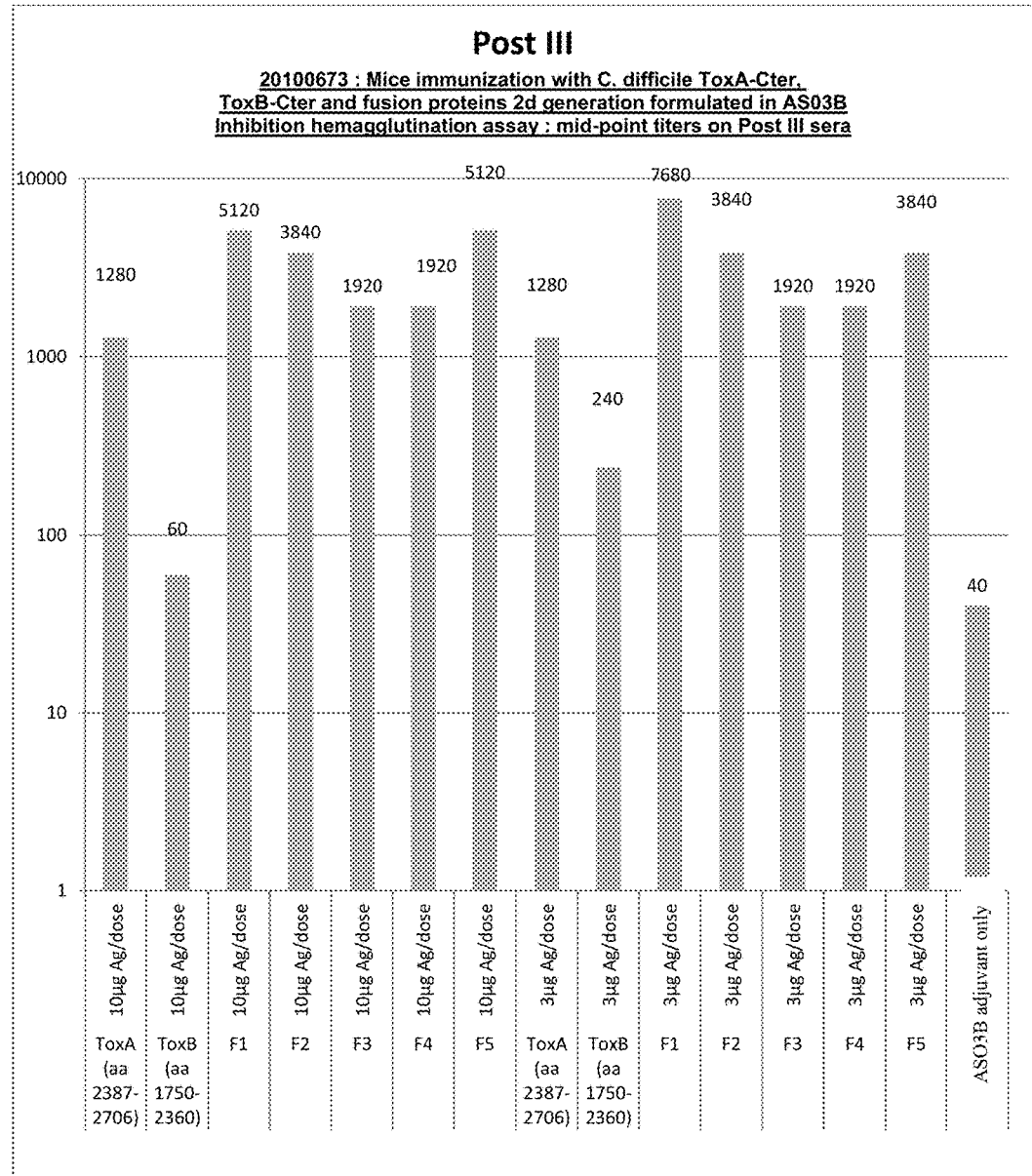
FIG. 12—Graph showing hemagglutination inhibition in mice immunised with a fragment of the C-terminus of toxin A (aa 2387-2706), a fragment of the C-terminus of toxin B (aa 1750-2360), or fusions 1, 2, 3, 4 or 5.

Haemagglutination inhibition titres are described in FIG. 12. Haemaglutination inhibition was observed with the anti-Tox A fragment sera or sera directed against each of the ToxA-ToxB fusions.

Figure 13:
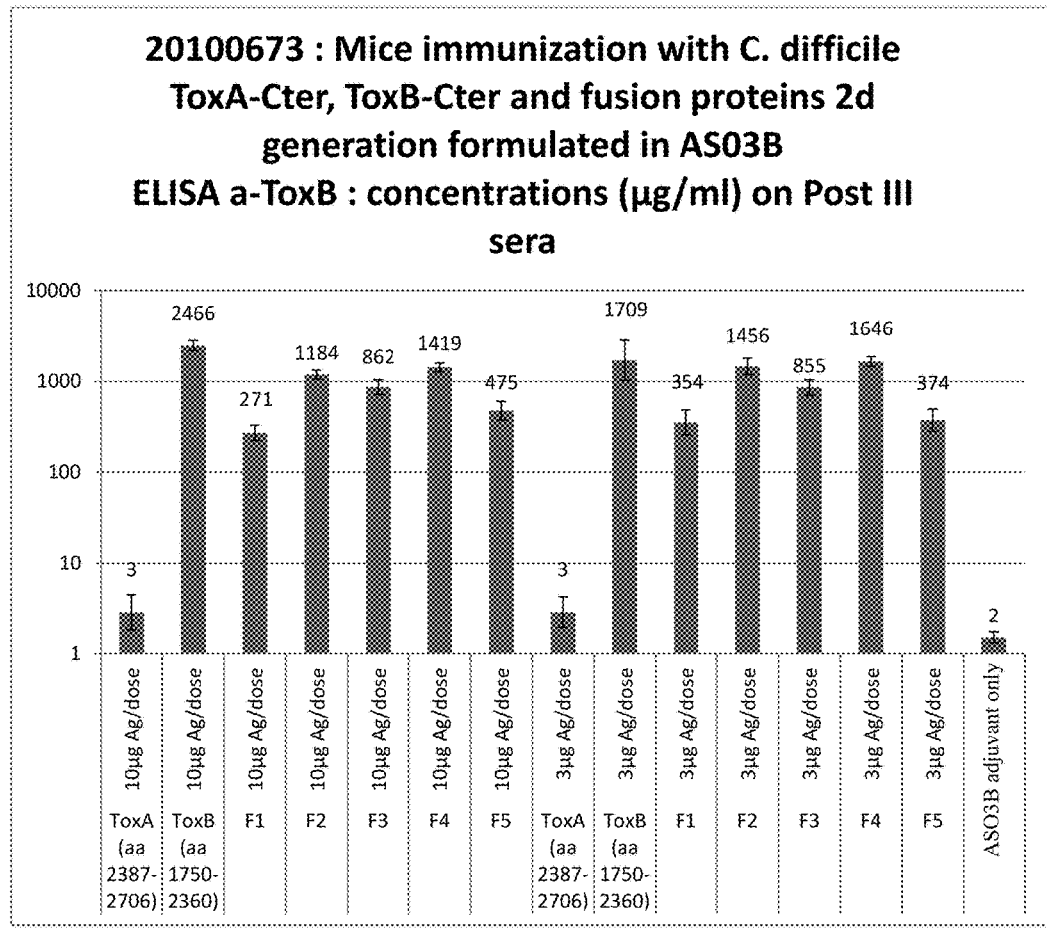
FIG. 13—Graph showing anti-ToxB immunogenicity in mice immunised with a fragment of the C-terminus of toxin A (aa 2387-2706), a fragment of the C-terminus of toxin B (aa 1750-2360), or fusions 1, 2, 3, 4 or 5.

An ELISA using ToxB antibodies was also performed; the results of this are illustrated in FIG. 13. Anti-Tox B antibodies were induced after immunization with the ToxB fragment alone but also with the F2, F3 and F4 fusions.

Figure 14:
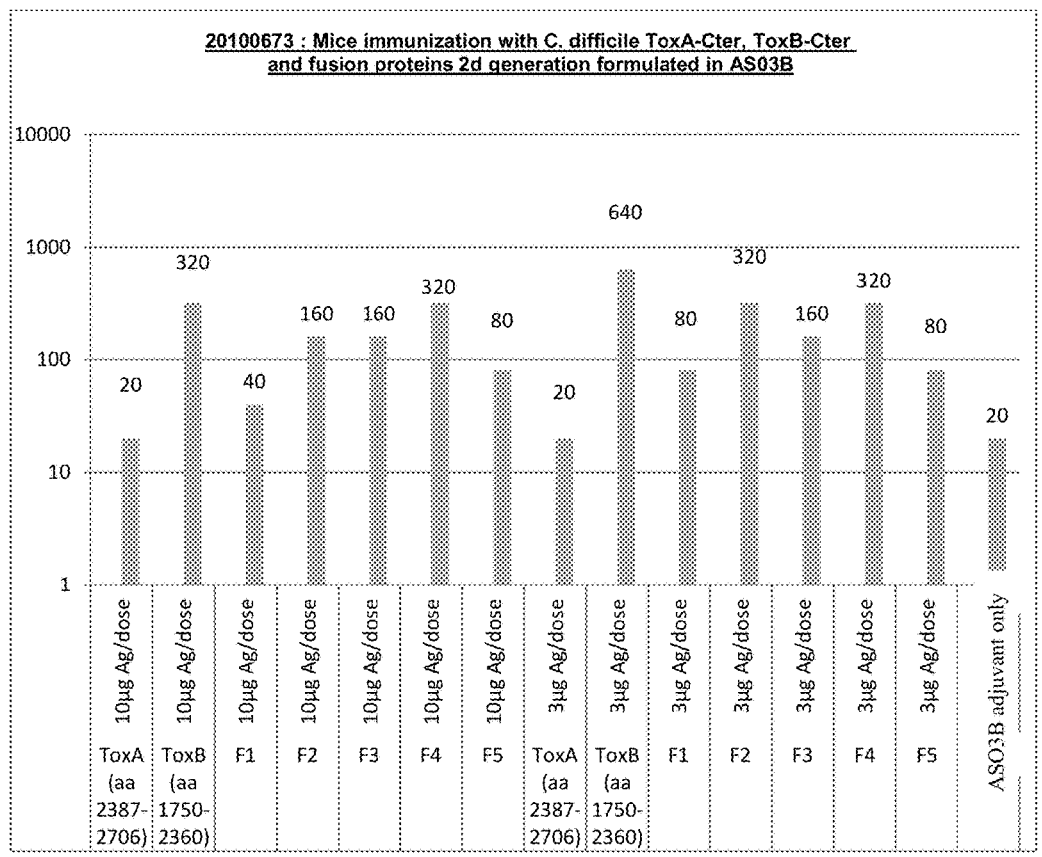
FIG. 14—Cyotoxicity inhibition titres from mice immunised with a fragment of the C-terminus of toxin A (aa 2387-2706), a fragment of the C-terminus of toxin B (aa 1750-2360), or fusions 1, 2, 3, 4 or 5.
Figure 15A:
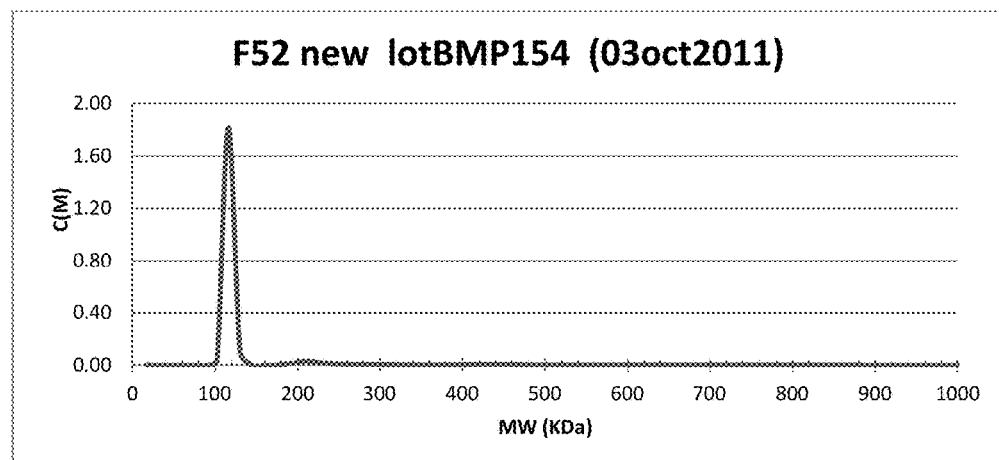
FIG. 15—Graphs describing the distribution of *C. difficile* ToxA-ToxB fusions F52New, F54Gly, F54New and F5ToxB as determined by sedimentation velocity analytical ultracentrifugation. Panel a) describes the distribution of F52New, panel b) describes the distribution of F54Gly, panel c) describes the distribution of F54New and panel d) describes the distribution of F5ToxB.
Figure 15B:
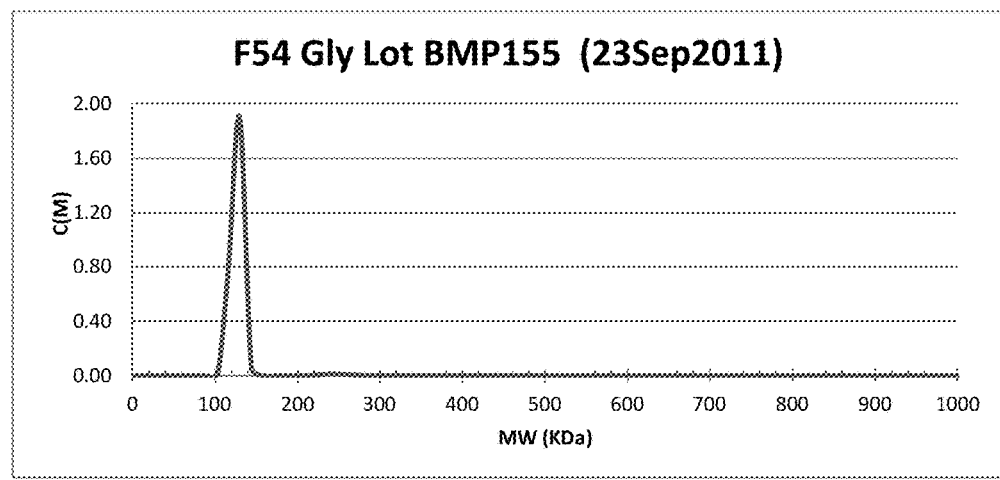
Figure 15C:
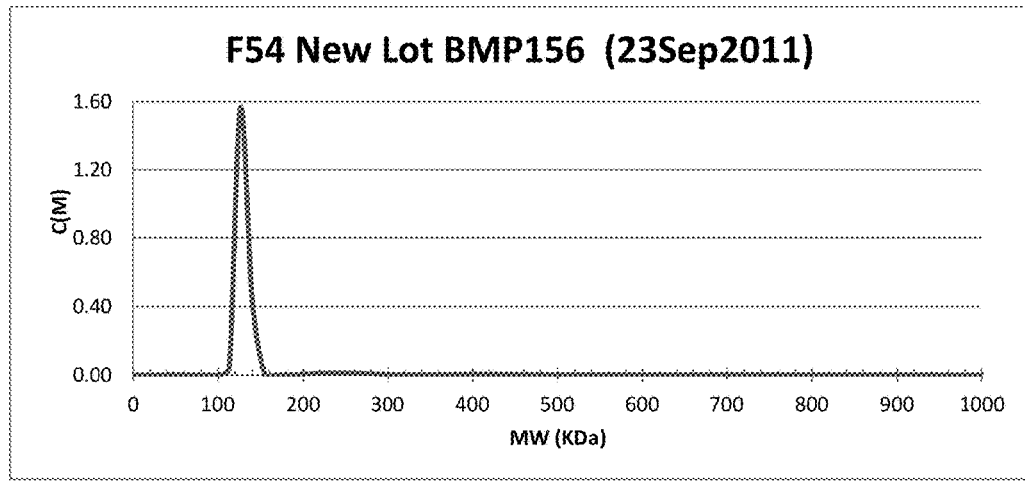
Figure 15D:
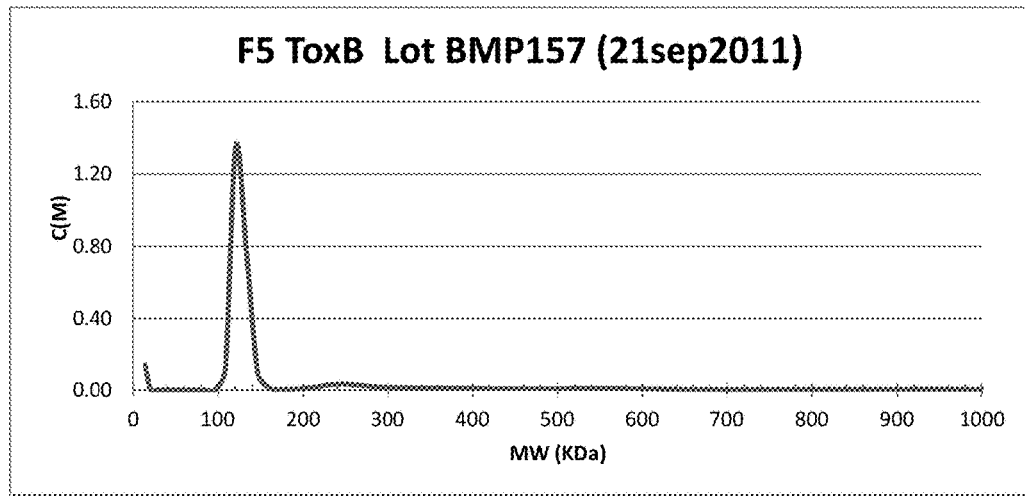
Figure 16:
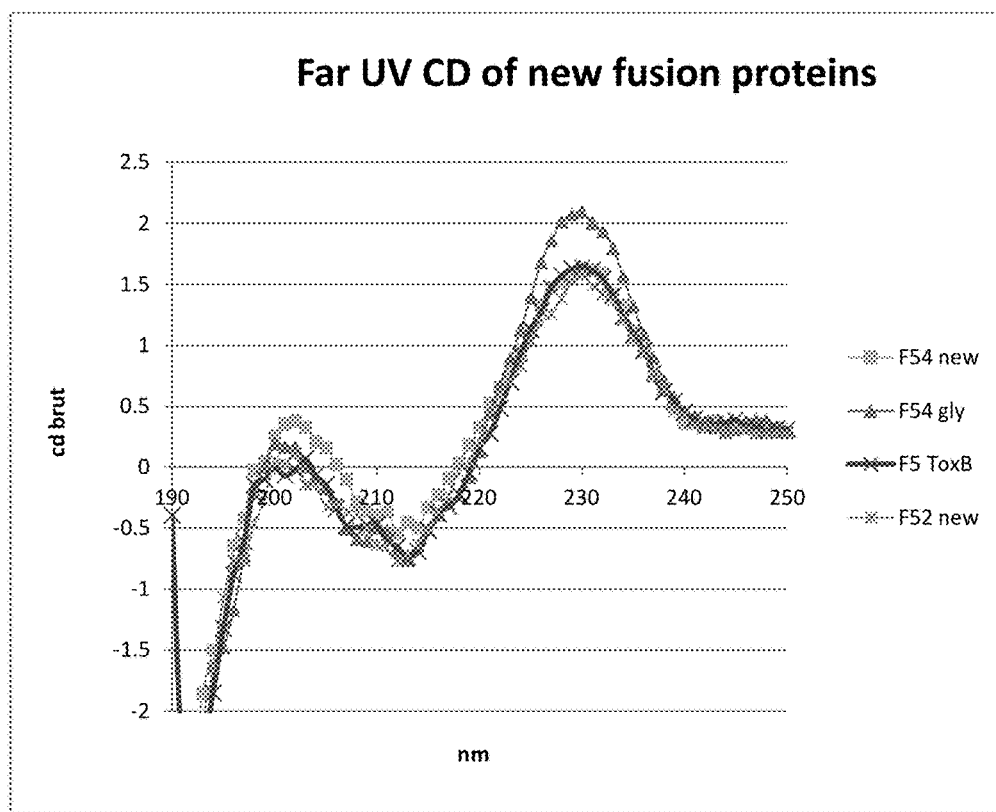
FIG. 16—Graph describing the Far-UV spectrum of fusions F52New, F54Gly, F54New and F5ToxB measured using circular dichroism. The spectrum for F52New is represented by a line with the points depicted as double crosses, the spectrum for F54Gly is represented by a line with the points depicted as triangles, F54New is represented by a line with the points depicted as squares, and F5ToxB is represented by a line with the points depicted as cross shapes.
Figure 21:
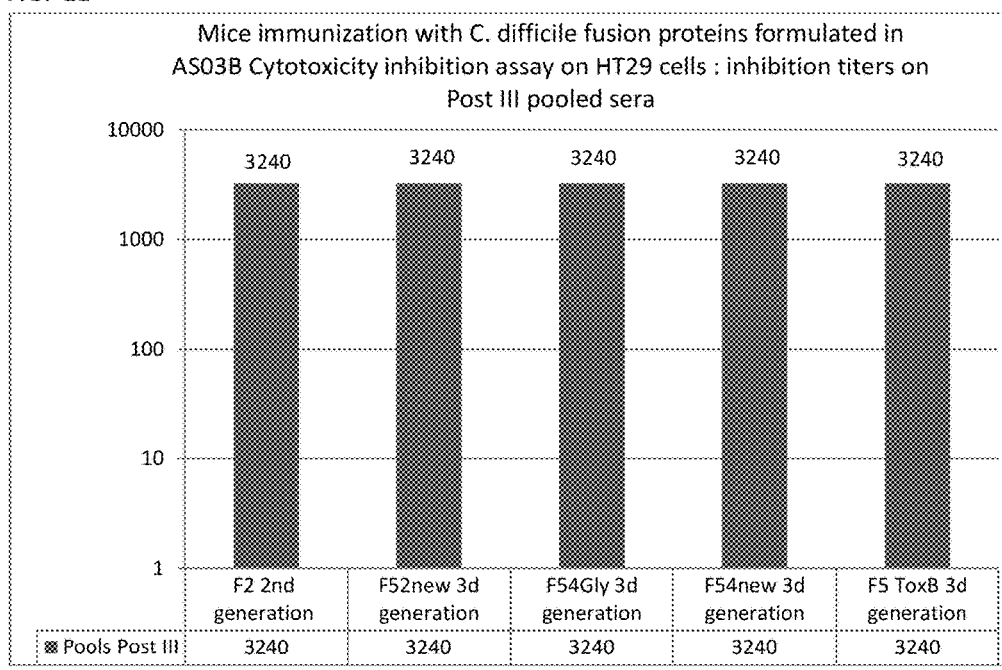
FIG. 21—Graph showing cytotoxicity titres in HT29 cells from mice immunised with the F2, F52New, F54Gly, F54New or F5ToxB fusions.
Figure 22:
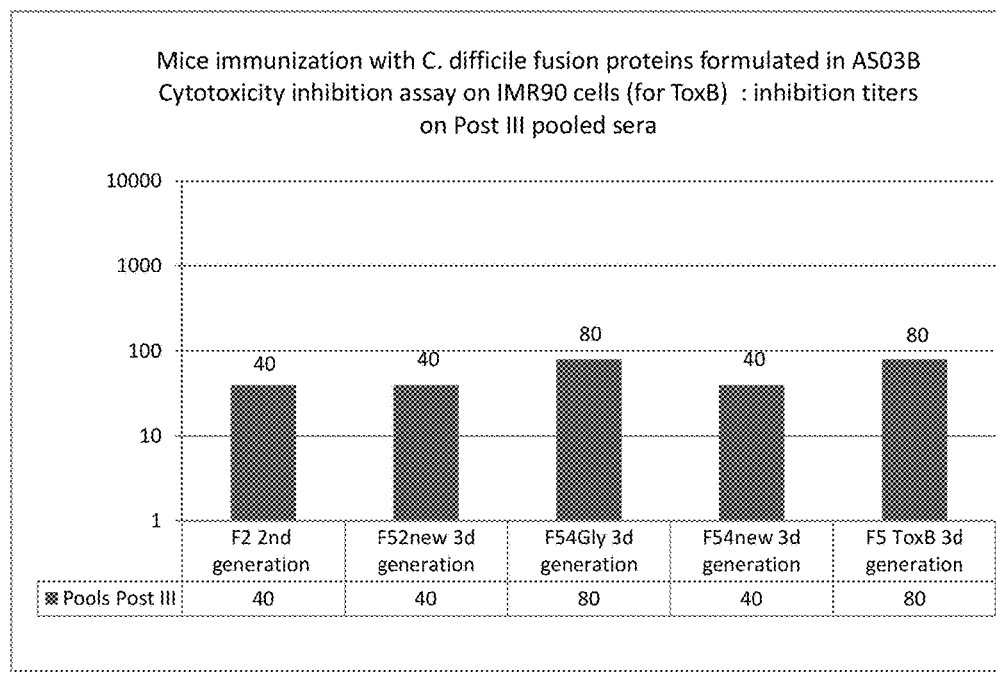
FIG. 22—Graph showing cytotoxicity titres in IMR90 cells from mice immunised with the F2, F52New, F54Gly, F54New or F5ToxB fusions.

Cytotoxicity inhibition titres are described in FIG. 14. Inhibition titers obtained using sera from mice immunised with the ToxB fragment or the ToxA-ToxB fusions were greater than that obtained using control sera.

Example 7

Design, Cloning, Expression and Purification of 4 Further Fusion Proteins

Four further fusion proteins were designed using the design principles described in example 1, these were named F54 Gly (SEQ ID NO:11), F54 New (SEQ ID NO:13), F5 ToxB (SEQ ID NO:15) and F52 New (SEQ ID NO:17).

These fusion proteins were expressed according to the procedure described in example 2.

Example 8

Molecular Weight Evaluation of the *C. Difficile* ToxA-ToxB Fusions Described in SEQ ID NO:11, SEQ ID NO:13, SEQ ID NO:15, and SEQ ID NO:17

The molecular weight of the fusions described in SEQ ID NO:11, SEQ ID NO:13, SEQ ID NO:15, and SEQ ID NO:17 were determined as described in example 4.

FIG. 15 describes the distribution of these four further fusion proteins as determined by sedimentation velocity analytical ultracentifugation.

The molecular weight of the main species determined from the C(S) distribution of all four protein fusions described in SEQ ID NO:11, SEQ ID NO:13, SEQ ID NO:15, and SEQ ID NO:17 corresponds to their monomeric form and all proteins exhibit sedimentation properties similar to F1 to F5 fusions.

Example 9

Evaluation of Secondary and Tertiary Structures of *C. Difficile* ToxA-ToxB Fusions Described in SEQ ID NO:11, SEQ ID NO:13, SEQ ID NO:15, and SEQ ID NO:17

The secondary and tertiary structures of the fusions described in SEQ ID NO:11, SEQ ID NO:13, SEQ ID NO:15, and SEQ ID NO:17 were assessed according to the method described in example 5. The far UV CD for these fusion proteins can be found in FIG. 16, and the near UV spectra for these fusions can be found in FIG. 17.

Analysis of the near and far UV CD spectra of the proteins described in SEQ ID NO:11, SEQ ID NO:13, SEQ ID NO:15, and SEQ ID NO:17 shows that all four have the same high beta sheet structure than F1 to F5 fusions. In addition, observation of the near UV spectra show no significant difference in the position of the aromatic amino acids in the tertiary structure compared to F1 to F5 fusions.

Example 10

Immunisation of Mice with Tox A-Tox B Fusions

Balb/c mice were immunised with the four fusion protein constructs F54 Gly (SEQ ID NO:11), F54 New (SEQ ID NO:13), F5 ToxB (SEQ ID NO:15) and F52 New (SEQ ID NO:17) as described in example 6.

An ELISA was carried out using the anti-ToxA and anti-ToxB ELISA response:protocol described in example 6 except here the samples of the toxA or toxB fragments were coated at 2 μg/ml in phosphate buffered saline on high-binding microtitre plates. A hemagglutination inhibition assay was performed as described in example 6. A toxB cytotoxicity assay was performed as described in example 6. A further toxA cytotoxicity assay was performed as described below.

ToxA Cytotoxicity Assay

HT29 cells were cultured at 37° C. with 5% $CO_2$ in DMEM+10% fetal bovine serum+1% glutamine+1% antibiotics (penicillin-streptomycin-amphotericin) and were seeded in 96-well tissue culture plates at a density of $5.10^4$ cells/well.

After 24 h, the cell media was removed from the wells.

Serial twofold dilutions of mice pooled antisera (50 μl) were performed in cell media.

50 μl of native Toxin B (0.15 ng/ml) is then added and the plates incubated at 37° C. with 5% CO$_2$ for 48 hours.

Cells were observed after 48 hours and the proportion of rounded cells were determined.

The results of the anti-toxA ELISA, anti-toxB Elisa, Haemagglutination inhibition and cytotoxicity assays are described in FIGS. 18, 19, 20, 21 and 22 respectively.

I claim:

1. A polynucleotide encoding a polypeptide comprising a first fragment and a second fragment, wherein
    (i) the first fragment is a fragment of *Clostridium difficile* (*C. difficile*) toxin A having the sequence of amino acids 2121-2686 of SEQ ID NO:1;

(ii) the second fragment is a fragment of *C. difficile* toxin B having the sequence of amino acids 1834-2366 of SEQ ID NO:2;

and wherein the first fragment and the second fragment are separated by five or fewer amino acids in the primary structure.

2. A vector comprising the polynucleotide of claim 1.

3. The vector of claim 2 further comprising an inducible promoter.

4. The vector of claim 3 wherein the inducible promoter is activated by addition of a sufficient quantity of IPTG.

5. A host cell comprising the vector of claim 2.

6. The host cell of claim 5 wherein the host cell is a gram negative bacterium.

7. The host cell of claim 6 wherein the host cell is *E. coli.*

8. The polynucleotide of claim 1, wherein the first fragment and the second fragment of the polypeptide are separated by a linker consisting of from one to three glycine residues.

9. A polynucleotide encoding a fusion polypeptide comprising SEQ ID NO:5.

10. A vector comprising the polynucleotide of claim 9.

11. The vector of claim 10 comprising an inducible promoter, wherein the inducible promoter is activated by addition of a sufficient quantity of IPTG.

12. A host cell comprising the vector of claim 10.

13. The host cell of claim 12 wherein the host cell is a gram negative bacterium.

14. The host cell of claim 12 wherein the host cell is *E. coli.*

* * * * *

UNITED STATES PATENT AND TRADEMARK OFFICE
CERTIFICATE OF CORRECTION

PATENT NO.        : 9,644,024 B2
APPLICATION NO.   : 15/041924
DATED             : May 9, 2017
INVENTOR(S)       : Cindy Castado Page 1 of 1

It is certified that error appears in the above-identified patent and that said Letters Patent is hereby corrected as shown below:

On the Title Page

Item (63), Line 2, under the heading Related U.S. Application Data:
PCT/EP2012/005793 should read -- PCT/EP2012/0059793 --.

Signed and Sealed this
Twenty-second Day of May, 2018

Andrei Iancu
*Director of the United States Patent and Trademark Office*